(12) United States Patent
Gaisina et al.

(10) Patent No.: US 10,934,255 B2
(45) Date of Patent: Mar. 2, 2021

(54) NRF AND HIF ACTIVATORS/HDAC INHIBITORS AND THERAPEUTIC METHODS USING THE SAME

(71) Applicant: THE BOARD OF TRUSTEES OF THE UNIVERSITY OF ILLINOIS, Urbana, IL (US)

(72) Inventors: Irina Gaisina, Berwyn, IL (US); Alan Kozikowski, Chicago, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 0 days.

(21) Appl. No.: 16/603,266

(22) PCT Filed: Apr. 25, 2018

(86) PCT No.: PCT/US2018/029258
§ 371 (c)(1),
(2) Date: Oct. 7, 2019

(87) PCT Pub. No.: WO2018/200608
PCT Pub. Date: Nov. 1, 2018

(65) Prior Publication Data
US 2020/0039933 A1    Feb. 6, 2020

Related U.S. Application Data

(60) Provisional application No. 62/490,101, filed on Apr. 26, 2017.

(51) Int. Cl.
C07D 209/30 (2006.01)
A61K 51/04 (2006.01)
A61K 45/06 (2006.01)

(52) U.S. Cl.
CPC ........ C07D 209/30 (2013.01); A61K 51/0453 (2013.01); A61K 45/06 (2013.01)

(58) Field of Classification Search
CPC ... C07D 209/30; A61K 51/0453; A61K 45/06
USPC ........................................................ 514/364
See application file for complete search history.

(56) References Cited

U.S. PATENT DOCUMENTS

| | | |
|---|---|---|
| 7,528,165 B2 | 5/2009 | Hsieh et al. |
| 2007/0142452 A1 | 6/2007 | Banner et al. |

FOREIGN PATENT DOCUMENTS

| | | |
|---|---|---|
| WO | WO-2006/088954 A1 | 8/2006 |
| WO | WO-2007/028638 A1 | 3/2007 |
| WO | WO-2008/019025 A2 | 2/2008 |
| WO | WO-2008/055068 A2 | 5/2008 |
| WO | WO-2011/011186 A2 | 1/2011 |
| WO | WO-2013/062344 A1 | 5/2013 |
| WO | WO-2013/134467 A1 | 9/2013 |
| WO | WO-2014/181137 A1 | 11/2014 |
| WO | WO-2017/053360 A1 | 3/2017 |

OTHER PUBLICATIONS

Abel et al., Epigenetic targets of HDAC inhibition in neurodegenerative and psychiatric disorders, Curr. Opin. Pharmacol., 8(1):57-64 (2008).
Andrews et al., Anti-malarial effect of histone deacetylation inhibitors and mammalian tumour cytodifferentiating agents, Int J. Parasitol., 30(6):761-8 (2000).
Barlev et al., Acetylation of p53 activates transcription through recruitment of coactivators/histone acetyltransferases, Mol. Cell, 8(6):1243-54 (Dec. 2001).
Björklund et al., Global transcription regulators of eukaryotes, Cell, 96(6):759-67 (1999).
Boyault et al., HDAC6, at the crossroads between cytoskeleton and cell signaling by acetylation and ubiquitination, Oncogene, 26(37):5468-76 (2007).
Bradley et al., Tumor targeting by covalent conjugation of a natural fatty acid to paclitaxel, Clin. Cancer Res., 7(10):3229-38 (Oct. 2001).
d'Yadewalle et al., HDAC6 inhibitors reverse axonal loss in a mouse model of mutant HSPB1-induced Charcot-Marie-Tooth disease, Nat. Med., 17(8):968-74 (2011).
Dal Maso et al., Epidemiology of non-Hodgkin lymphomas and other haemolymphopoietic neoplasms in people with AIDS, Lancet Oncol., 4(2):110-9 (2003).
de Ruijter et al., Histone deacetylases (HDACs): characterization of the classical HDAC family, Biochem. J., 370(Pt. 3):737-49 (2003).
Dompierre et al., Histone deacetylase 6 inhibition compensates for the transport deficit in Huntington's disease by increasing tubulin acetylation, J. Neurosci., 27(13):3571-83 (2007).
Dregan et al., Is sodium valproate, an HDAC inhibitor, associated with reduced risk of stroke and myocardial infarction? A nested case-control study, Pharmacoepidemiol Drug Saf., 23(7):759-67 (Jul. 2014).
El-Serag, Hepatocellular carcinoma: an epidemiologic view, J. Clin. Gastroenterol., 35(5 Suppl 2):S72-8 (2002).
Gandaglia et al., The role of chronic prostatic inflammation in the pathogenesis and progression of benign prostatic hyperplasia (BPH), BJU Int., 112(4):432-41 (Aug. 2013).
Glaser et al., Role of class I and class II histone deacetylases in carcinoma cells using siRNA, Biochem. Biophys. Res. Commun., 310(2):529-36 (Oct. 2003).

(Continued)

*Primary Examiner* — Kristin A Vajda
(74) *Attorney, Agent, or Firm* — Marshall, Gerstein & Borun LLP

(57) ABSTRACT

Compounds that inhibit histone (HDACI) and/or activate Nrf2 and HIF, and compositions containing the same are disclosed. Methods of treating diseases and conditions wherein inhibition of HDAC and/or activation of Nrf2 and HIF provide a benefit, like a cancer, a neurodegenerative disorder, a peripheral neuropathy, a neurological disease, traumatic brain injury, stroke, hypertension, malaria, an autoimmune disease, autism, autism spectrum disorders, and inflammation, also are disclosed.

18 Claims, 4 Drawing Sheets

(56) References Cited

OTHER PUBLICATIONS

Grozinger et al., Three proteins define a class of human histone deacetylases related to yeast Hda1p, Proc. Natl. Acad. Sci. USA, 96(9):4868-73 (1999).
Gu et al., Activation of p53 sequence-specific DNA binding by acetylation of the p53 C-terminal domain, Cell, 90(4):595-606 (Aug. 1997).
Haggarty et al., Domain-selective small-molecule inhibitor of histone deacetylase 6 (HDAC6)-mediated tubulin deacetylation, Proc. Natl. Acad. Sci. USA, 100(8):4389-94 (2003).
Hernández-Avila et al., Human papilloma virus 16-18 infection and cervical cancer in Mexico: a case-control study, Arch. Med. Res., 28(2):265-71 (1997).
Herrmann et al., Epstein-Barr virus-associated carcinomas: facts and fiction, J. Pathol., 199(2):140-5 (Feb. 2003).
Hillgren et al., In vitro systems for studying intestinal drug absorption, Med. Res. Rev., 15(2):83-109 (Mar. 1995).
Hockly et al., Suberoylanilide hydroxamic acid, a histone deacetylase inhibitor, ameliorates motor deficits in a mouse model of Huntington's disease, Proc. Natl. Acad. Sci. USA, 100(4):2041-6 (Feb. 2003).
International Application No. PCT/US18/29258, International Preliminary Report on Patentability, dated Oct. 29, 2019.
International Application No. PCT/US18/29258, International Search Report and Written Opinion, dated Jul. 9, 2018.
Ito et al., MDM2-HDAC1-mediated deacetylation of p53 is required for its degradation, EMBO J., 21(220:6236-45 (Nov. 2002).
Ito et al., p300/CBP-mediated p53 acetylation is commonly induced by p53-activating agents and inhibited by MDM2, EMBO J., 20(6):1331-40 (Mar. 2001).
Itoh et al., Design, synthesis, structure--selectivity relationship, and effect on human cancer cells of a novel series of histone deacetylase 6-selective inhibitors, J. Med. Chem., 50(22):5425-38 (2007).
Kadow et al., The role of viruses in human cancer development and antiviral approaches for intervention, Curr. Opin. Investig. Drugs, 3(11):1574-9 (2002).
Kazantsev et al., Therapeutic application of histone deacetylase inhibitors for central nervous system disorders, Nat. Rev. Drug Discov., 7(10):854-68 (2008).
Kozikowski et al., Functional differences in epigenetic modulators-superiority of mercaptoacetamide-based histone deacetylase inhibitors relative to hydroxamates in cortical neuron neuroprotection studies, J. Med. Chem., 50(13):3054-61 (2007).
Liu et al., p53 sites acetylated in vitro by PCAF and p300 are acetylated in vivo in response to DNA damage, Mol Cell Biol., 19(2):1202-9 (Feb. 1999).
Ma et al., Asymmetric dipolar cycloaddition reactions: a practical, convergent synthesis of chiral pyrrolidines, Tetrahedron:Asymmetry, 8(6):883-7 (1997).
Manku et al., Synthesis and evaluation of lysine derived sulfamides as histone deacetylase inhibitors, Bioorg. Med. Chem. Lett., 19(7):1866-70 (2009).
Minucci et al., Histone deacetylase inhibitors and the promise of epigenetic (and more) treatments for cancer, Nat. Rev. Cancer, 6(1):38-51 (2006).
Mortreux et al., Molecular and cellular aspects of HTLV-1 associated leukemogenesis in vivo, Leukemia, 17(1):26-38 (2003).
Oleinick et al., Nuclear structure and the microdistribution of radiation damage in DNA, Int. J. Radiat. Biol., 66(5):523-9 (1994).
Parmigiani et al., HDAC6 is a specific deacetylase of peroxiredoxins and is involved in redox regulation, Proc. Natl. Acad. Sci. USA, 105(28):9633-8 (Jul. 2008).
Rivieccio et al., HDAC6 is a target for protection and regeneration following injury in the nervous system, Proc. Natl. Acad. Sci. USA, 106(46):19599-604 (2009).
Rouaux et al., Targeting CREB-binding protein (CBP) loss of function as a therapeutic strategy in neurological disorders, Biochem. Pharmacol., 68(6):1157-64 (2004).
Sakaguchi et al., DNA damage activates p53 through a phosphorylation-acetylation cascade, Genes Dev., 12(18):2831-41 (Sep. 1998).
Schafer et al., Pyridylalanine-containing hydroxamic acids as selective HDAC6 inhibitors, ChemMedChem., 4(2):283-90 (2009).
Struhl et al., The TAFs in the HAT, Cell, 94(1):1-4 (1998).
Tan et al., Novel histone deacetylase inhibitors in clinical trials as anti-cancer agents, J. Hematol. Oncol., 3:5 (2010).
Valenzuela-Fernandez et al., HDAC6: a key regulator of cytoskeleton, cell migration and cell-cell interactions, Trends Cell Biol., 18(6):291-7 (2008).
Wang et al., Design, synthesis, and evaluation of hydroxamic acid-based molecular probes for in vivo imaging of histone deacetylase (HDAC) in brain, Am. J. Nucl. Med. Mol. Imaging, 4(1):29-38 (Dec. 2013).
Wang et al., Immunomodulatory effects of deacetylase inhibitors: therapeutic targeting of FOXP3+ regulatory T cells, Nat. Rev. Drug Discov., 8(12):969-81 (2009).
Wang et al., Using histone deacetylase inhibitors to enhance Foxp3(+) regulatory T-cell function and induce allograft tolerance, Immunol. Cell Biol., 87(3):195-202 (Mar.-Apr. 2009).
Witt et al., HDAC family: What are the cancer relevant targets?, Cancer Lett., 277(1):8-21 (2009).
Zhang et al., Enhanced radiation sensitivity in prostate cancer by gold-nanoparticles, Clin. Invest. Med., 31(3):E160-7 (2008).
Tran-Thi-Lan Huong et al: "Novel N-hydroxybenzamides incorporating 2-oxoindoline with unexpected potent histone deacetylase inhibitory effects and antitumor cytotoxicity",*Bioorganic Chemistry.*, vol. 71, Apr. 1, 2017, pp. 160-169.

NRF AND HIF ACTIVATORS/HDAC INHIBITORS AND THERAPEUTIC METHODS USING THE SAME

CROSS-REFERENCE TO RELATED APPLICATIONS

This application is the U.S. National Stacie application of International Patent Application No. PCT/US2018/029258, filed Apr. 26, 2018, which claims the benefit of U.S. Provisional Patent Application No. 62/490,101, filed Apr. 26, 2017.

STATEMENT OF GOVERNMENT INTEREST

This invention was made with government support under contract No. NS079183 awarded by the National Institutes of Health. The government has certain rights in the invention.

FIELD OF THE INVENTION

The present invention relates to indoline and benzimidazole compounds that activate Nrf2 and HIF and inhibit histone deacetylase (HDAC), to pharmaceutical compositions comprising one or more of the compounds, to methods of increasing the sensitivity of cancer cells to the cytotoxic effects of radiotherapy and/or chemotherapy comprising contacting the cell with one or more of the compounds, and to therapeutic methods of treating conditions and diseases wherein activation of Nrf2 and HIF and/or inhibition of HDAC provides a benefit, for example, a cancer, an inflammation, a neurological disease, a neurodegenerative disorder, stroke, traumatic brain injury, allograft rejection, autoimmune diseases, and malaria, comprising administering a therapeutically effective amount of a present compound to an individual in need thereof.

BACKGROUND OF THE INVENTION

Inhibitors of HDACs modulate transcription and induce cell growth arrest, differentiation, and apoptosis. HDAC inhibitors (HDACIs) also enhance the cytotoxic effects of therapeutic agents used in cancer treatment, including radiation and chemotherapeutic drugs. Moreover, recent research indicates that transcriptional dysregulation may contribute to the molecular pathogenesis of certain neurodegenerative disorders, such as Huntington's disease, Rett syndrome, Charcot-Marie-Tooth disease (CMT) and other peripheral neuropathies, spinal muscular atrophy, amyotropic lateral sclerosis, and ischemia. For example, suberoylanilide hydroxamic acid (SAHA) has been shown to penetrate into the brain to dramatically improve motor impairment in a mouse model of Huntington's disease, thereby validating research directed to HDACIs in the treatment of neurodegenerative diseases. Furthermore, selective HDAC6 inhibitors have been shown to rescue the CMT phenotype, restore proper mitochondrial motility, and correct the axonal transport defects observed in transgenic mice. Selective HDAC6 inhibitors also induce the re-innervation of muscles and increase the number of observed neuromuscular junctions in these same models (C. d'Ydewalle et al., Nature Medicine 2011).

A recent review summarized evidence that aberrant histone acetyltransferase (HAT) and HDAC activity may be a common underlying mechanism contributing to neurodegeneration. Moreover, from a mouse model of depression, the therapeutic potential of HDACs in treating depression is discussed. See WO 2008/019025, designating the United States, incorporated herein in its entirety.

Eleven isozymes in the HDAC family of enzymes, which can be grouped into classes by their evolutionary relationships, have been identified. Structure and function appear to be conserved among members of the various classes. The HDAC family is made up of class I HDACs, including HDAC1, 2, 3, and 8; class IIa, including HDAC4, 5, 7, and 9; class IIb, including HDAC6 and 10; and a class IV enzyme, HDAC11 (A. J. de Ruijter et al., The Biochemical Journal 2003, 370(Pt), 737-749).

The class I HDACs are found primarily in the nucleus and are expressed in all tissue types, except for the muscle cell-specific HDAC8. The class I HDACs interact with many key transcription factors regulating gene expression, including CoREST and NuRD. Class IIa HDACs have tissue specific expression, and are found in both the nucleus and cytoplasm. Unlike the other isozymes, the class IIb HDAC6 does not extensively associate with transcription factors, and acts as a deacetylase on non-histone proteins, including α-tubulin, HSP90, cortactin, and the peroxiredoxins (O. Witt et al., Cancer Letters 2008; R. B. Parmigiana et al., PNAS 2008).

HDACs form multiprotein complexes with many regulatory proteins inside the cell. For example, HDAC4, 5, and 7 actually lack intrinsic deacetylase ability, and gain activity only by interacting with HDAC3. Each isozyme interacts with a specific series of regulatory proteins and transcription factors and has a specific set of substrates, and thus each regulates a specific series of genes and proteins (O. Witt et al., Cancer Letters 2008). The design of selective HDAC isozyme inhibitors allows preferential inhibition of only the isozyme(s) relevant to a particular disease or condition, thereby reducing the probability of counterproductive and/or adverse effects resulting from an unwanted and undesired inhibition of other HDAC isozymes.

HDAC6 is the most abundant histone deacetylase isozyme in the human body, and along with HDAC7, is the most commonly expressed isozyme in the brain (A. J. de Ruijter et al., The Biochemical Journal 2003, 370(Pt), 737-749). Structurally significant features of HDAC6 include two deacetylase domains and a zinc finger motif. It is most commonly found in the cytoplasm, but can be shuttled into the nucleus via its nuclear export signal. A cytoplasmic retention signal, which sequesters the enzyme in the cytoplasm, also was found (A. Valenzuela-Fernandez et al., Trends in Cell Biology 2008, 18(6), 291-297). The functions of HDAC6 are unlike any of the other HDAC isozymes. Many non-histone substrates are deacetylated by HDAC6, including α-tubulin, HSP90, cortactin, and peroxiredoxins (O. Witt et al., Cancer Letters 2008; R. B. Parmigiani et al., PNAS USA 2008, 105(28), 9633-9638). A detaialed review of HDAC6 is found in Simoes-Pines et al. Molecular Neurodegregation 2013, 8:7.

Currently, at least eleven HDACIs are in clinical development. These HDACIs can be divided into at least five chemical classes, illustrated below, based on their structure, and in most cases they broadly and nonselectively inhibit class I/II HDACs with varying efficiency. These five chemical classes are hydroxamates, cyclic tetrapeptides, cyclic peptides, short-chain fatty acids, and benzamides. Typically, known HDACIs fail to show prominent HDAC isozyme selectivity, which as stated above can cause serious problems in a clinical setting, especially in the treatment of diseases and conditions wherein a prolonged drug administration of an HDACI is required. For example, it has been found that some HDACIs enhance lung and microglial inflammation (TSA and SAHA), as well as high glucose-induced inflammation. If this effect is linked to specific HDAC isozymes, the use of certain HDACIs would be contraindicated in various diseases and conditions, such as diabetes and asthma.

Additional HDACI's include

Classes of HDAC inhibitors

Aliphatic acids

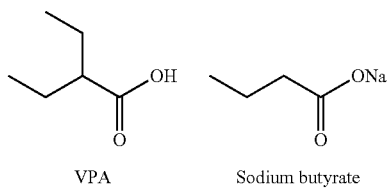

VPA  Sodium butyrate

Hydroxamates

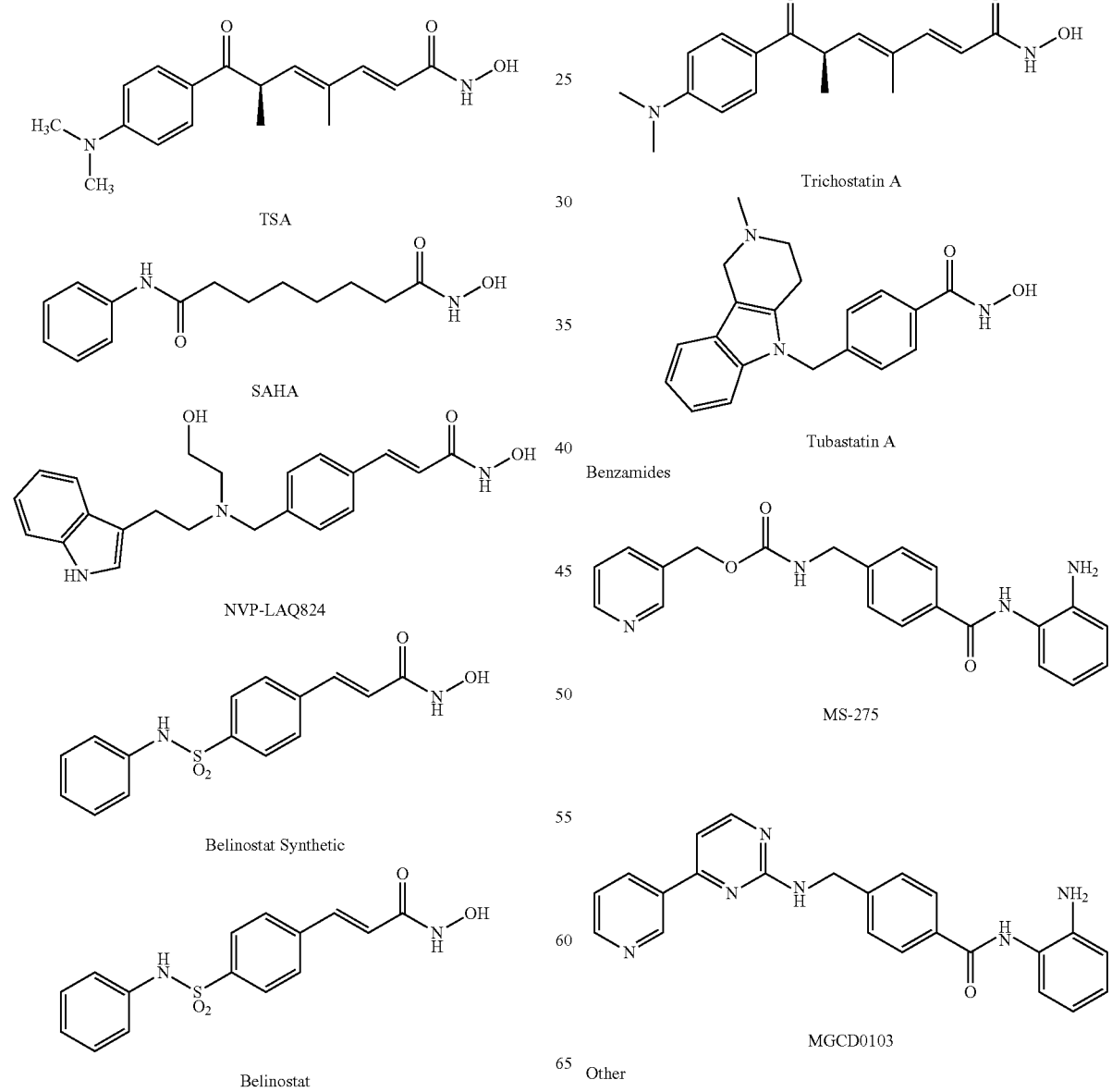

-continued

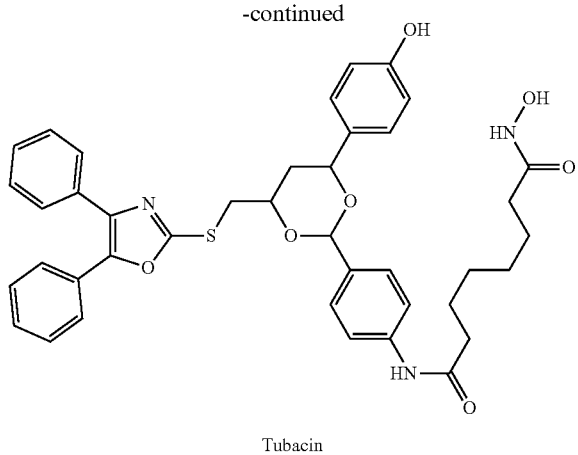
Tubacin

Cyclic peptides

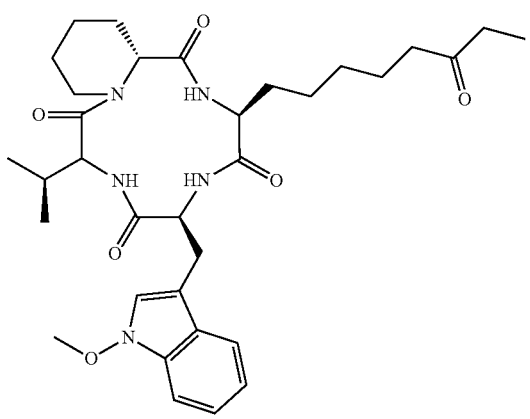
Apicidin Natural Product

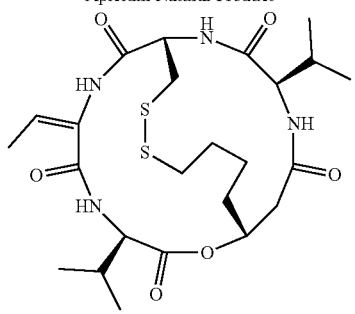
Depsipeptide

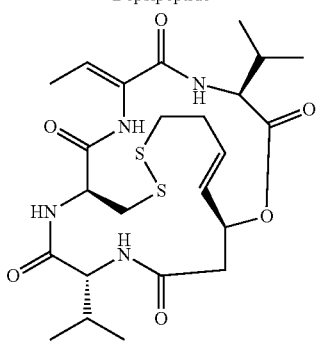
Romidepsin Natural Product

The following table summarizes some HDACIs that presently are in clinical trials.

TABLE I

| Inhibitor | Indications |
|---|---|
| SAHA | T-cell lymphoma (Approved) |
| Romidepsin | T-cell lymphoma (Approved) |
| | Multiple myeloma (Phase III) |
| | Peripheral T-cell lymphoma (Phase III) |
| | Refractory renal cell cancer (Phase II) |
| Valproic Acid | Bipolar disorder (Approved) |
| | Acute myeloid leukemia (Phase I/II with all trans-retinoic acid) |
| PCI-24781 | Leukemia (Phase I/II) |
| ITF-2357 | Hodgkins lymphoma (Phase II) |
| | Follicular lymphoma (Phase III, with yttrium-90-ibritumomab) |
| | Juvenile arthritis (Phase II) |
| | Myeloproliferative Diseases (Phase II) |
| MS-275 | Melanoma |
| | Lymphoma (halted due to dose limiting toxicities) |
| | Advanced acute leukemias (Phase 1) |
| | Combination trials with DNA methyltransferase inhibitors and 5-azacitidine in non-small cell lung cancer (Preclinical) |
| Panbinostat | T-cell lymphoma (Phase II) |
| | Prostate cancer (Phase I with docetaxel) |
| Belinostat | Solid tumors (Phase I) |
| | Mesothelioma (Abandoned) |
| MGCD0103 | Solid tumors (Phase II with gemcitabine) |
| | Diffuse large B-cell lymphoma (Phase II) |
| EVP-0334 | Parkinson's disease (Phase I) |

Clinical trial information relating to HDACIs is published in J. Tan et al., *Journal of hematology & oncology.* 3:5 (2010) and L. Wang et al., *Nat Rev Drug Discov.* 8:969-81 (2009).

HDAC-regulated factors have been implicated in the mechanisms of major central nervous system (CNS) disorders. In Parkinson's disease (PD), α-synuclein binds to histones and inhibits HAT activity, causing neurodegeneration. Application of HDACIs to PD neurons blocks α-synuclein toxicity. Dysregulation of histone acetylation, involving CBP, a neuroprotective transcription factor with histone acetyltransferase activity, has been found in Huntington's disease (HD), Alzheimer's disease (AD), and Rubinstein-Taybi syndrome (T. Abel et al., *Curr. Opin. in Pharmacol.* 2008, 8(1), 57-64). In a cellular model of AD, cell death was accompanied by loss of CBP function and histone deacetylation. The mutant HD protein, htt, interacts with CBP, inhibiting the HAT activity and causing cell death. Treatment with an HDACI helps to restore histone acetylation, protecting against neurodegeneration and improving motor performance in a mouse model of HD (C. Rouaux et al., *Biochem. Pharmacol.* 2004, 68(6), 1157-1164).

Various studies directed to the application of HDACIs in the context of CNS disorders have implicated the class II HDACs, particularly HDAC6, as potential therapeutic targets. One investigation revealed that inhibition of HDAC6 could be beneficial as a treatment for HD, a disease for which no pharmacological treatment is available. The mutant htt protein found in HD disrupts intracellular transport of the pro-survival and pro-growth nerve factor, BDNF, along the microtubule network, causing neuronal toxicity. Inhibition of HDAC6 promotes transport of BDNF by promoting tubulin hyperacetylation. TSA (trichostatin A), a nonselective HDAC inhibitor, was found to facilitate transport and release of BNDF-containing vesicles (J. P. Dompierre et al., *J Neurosci* 2007, 27(13), 3571-3583). These results provide a biological basis for the identification and development of HDACIs, and particularly HDAC6 selective inhibitors, as a treatment for HD and other neurodegenerative disorders.

HDACIs prevent or delay neuronal dysfunction and death in in vitro and in vivo models thereby indicating that HDACIs are broadly neuroprotective. For example, HDACIs have shown therapeutic efficacy in the polyglutamine-expansion disorder Huntington's disease. While the neuroprotective mechanisms of the HDACIs in rodent models are not yet understood, it is clear that HDACIs induce the expression of certain genes that confer neuroprotection. The upregulation of HSP-70 and Bcl-2 through the inhibition of HDAC has been observed in the cortex and striatum of rats after focal cerebral ischemia. HSP-70 expression has been found to result in neuroprotection in a number of disease models including Alzheimer's disease (AD), Parkinson's disease (PD), and Huntington's disease (HD). In addition, HDAC6 inhibition leads to the acetylation of peroxiredoxin and increases its antioxidant activity which may contribute to the neuroprotective effects of these compounds (R. B. Parmigiana et al., *PNAS* 2008).

Studies also provide good evidence that HDACI-induced p21cip1/waf1 expression may play a significant role in HDACI-mediated neuroprotection. It recently was reported that p21cip1/waf1 overexpression protects neurons from oxidative stress-induced death, that p21cip1/waf1 is induced in the rodent brain by HDAC inhibition, and that homozygous loss of p21cip1/waf1 exacerbates damage in a mouse MCAO/reperfusion model of ischemic stroke. In a similar study, the HDAC inhibitor TSA was shown to increase gelsolin expression in neurons, and that gelsolin expression is necessary for neuroprotection in an oxygen/glucose deprivation model of neurodegeneration and a mouse MCAO/reperfusion model of ischemic stroke.

Alternatively, unrelated to histone acetylation and gene upregulation, proteins such as α-tubulin and HSP90 are targets for acetylation and become acetylated when HDACs are inhibited. In tumor cells, the acetylation of HSP90 has been shown to decrease the ability of HSP90 to interact with certain client proteins and thereby abrogate chaperone function. With regard to stroke and traumatic brain injury (TBI), as well as several other neurodegenerative diseases, the inhibition of HSP90 is predicted to have a positive effect on neuronal survival. Indeed, the pharmacological HSP90 inhibitor, Geldanamycin, and its analogs have been shown to be neuroprotective in a number of stroke models. HSP90 inhibition and the consequent release of heat-shock factor (HSF) to the nucleus may also, in part, explain an upregulation of HSP70 in the brain during focal ischemia and HDACI treatment.

In addition, HDACIs are useful in the treatment of cancers. For example, histone acetylation and deacetylation play important roles in chromatin folding and maintenance (Kornberg et al., Bjorklund et al., *Cell,* 1999, 96:759-767; Struhl et al., *Cell,* 1998, 94:1-4). Acetylated chromatin is more open and has been implicated in the increased radiation sensitivities observed in some cell types (Oleinick et al., *Int. J. Radiat. Biol.* 1994, 66:523-529). Furthermore, certain radiation-resistant human cancer cells treated with the HDACI inhibitor TSA were sensitized to the damaging effects of ionizing radiation. Thus, HDACIs appear useful as radiation sensitizing agents.

WO 2008/055068, designating the U.S. and incorporated herein in its entirety, discloses numerous diseases and conditions treatable by HDACIs, including the underlying science and reasoning supporting such treatments.

HDAC6 therefore has emerged as an attractive target for drug development and research. (C. M. Grozinger et al., *Proc. Natl. Acad. Sci. USA* 1999, 96, 4868-73; and C. Boyault et al., *Oncogene* 2007, 26, 5468-76.) Presently, HDAC6 inhibition is believed to offer potential therapies for autoimmunity, cancer, and many neurodegenerative conditions. (S. Minucci et al., *Nat. Rev. Cancer.* 2006, 6, 38-51; L. Wang et al., *Nat. Rev. Drug Discov.* 2009, 8, 969-81; J. P. Dompierre et al., *J. Neurosci.* 2007, 27, 3571-83; and A. G. Kazantsev et al., *Nat. Rev. Drug Discov.* 2008, 7, 854-68.) Selective inhibition of HDAC6 by small molecule or genetic tools has been demonstrated to promote survival and regrowth of neurons following injury, offering the possibility for pharmacological intervention in both CNS injury and neurodegenerative conditions. (M. A. Rivieccio et al., *Proc. Natl. Acad. Sci. USA* 2009, 106, 19599-604.) Unlike other histone deacetylases, inhibition of HDAC6 does not appear to be associated with any toxicity, making it an excellent drug target. (O. Witt et al., *Cancer Lett* 2009, 277, 8-21.) Tubacin, an HDAC6 selective inhibitor, used in models of disease, has helped to validate, in part, HDAC6 as a drug target, but its non-drug-like structure, high lipophilicity (C log P=6.36 (KOWWIN)) and tedious synthesis make it more useful as a research tool than a drug. (S. Haggarty et al., *Proc. Natl. Acad. Sci. USA* 2003, 100, 4389-94.) Other compounds also have a modest preference for inhibiting HDAC6. (S. Schafer et al., *ChemMedChem* 2009, 4, 283-90; Y. Itoh et al., *J. Med. Chem.* 2007, 50, 5425-38; and S. Manku et al., *Bioorg. Med. Chem. Lett.* 2009, 19, 1866-70.)

Transcription factors Nrf2 and HIF1 are key regulators of the antioxidant response genetic program. HIF is a widespread transcription factor activating a battery of genes, including those involved in glucose uptake and metabolism, extracellular pH control, angiogenesis, erythropoiesis, and mitogenesis. HIF acts to enhance the cell survival ability. Activation of the Nrf2 pathway also is known to be beneficial in animal models of various central nervous system diseases, including chronic neurodegenerative diseases, such as Parkinson's and Alzheimer's disease, and acute insults, such as brain ischemia and brain trauma.

In summary, extensive evidence supports a therapeutic role for HDACIs and Nrf 2 and HIF1 activators in the treatment of a variety of conditions and diseases, such as cancers and CNS diseases and degenerations. However, despite exhibiting overall beneficial effects, like beneficial neuroprotective effects, for example, HDACIs known to date have little specificity with regard to HDAC inhibition, and therefore inhibit all zinc-dependent histone deacetylases. It is still unknown which is (are) the salient HDAC(s) that mediate(s) neuroprotection when inhibited. Emerging evidence suggests that at least some of the HDAC isozymes are absolutely required for the maintenance and survival of neurons, e.g., HDAC1. Additionally, adverse side effect issues have been noted with nonspecific HDAC inhibition. Thus, the clinical efficacy of present-day nonspecific HDACIs for stroke, neurodegenerative disorders, neurological diseases, and other diseases and conditions ultimately may be limited. It is important therefore to design, synthesize, and test compounds capable of serving as potent, and preferably isozyme-selective, HDACIs that are able to ameliorate the effects of neurological disease, neurodegenerative disorder, traumatic brain injury, cancer, inflammation, malaria, autoimmune diseases, immunosuppressive therapy, and other conditions and diseases mediated by HDACs.

An important advance in the art would be the discovery of HDACIs, and particularly selective HDAC6 inhibitors, that are useful in the treatment of diseases wherein HDAC inhibition provides a benefit, such as cancers, neurological diseases, traumatic brain injury, neurodegenerative disorders and other peripheral neuropathies, stroke, hypertension, malaria, allograft rejection, rheumatoid arthritis, and inflammations. A further important advance in the art would be the discovery of an HDACI, and particularly selective HDAC6 inhibitors, that also activate Nrf2 and HIF. Accordingly, a significant need exists in the art for efficacious compounds, compositions, and methods useful in the treatment of such diseases, alone or in conjunction with other therapies used to treat these diseases and conditions. The present invention is directed to meeting this need.

SUMMARY OF THE INVENTION

The present invention relates to indoline and benzimidazole compounds, pharmaceutical compositions comprising the compounds, and methods of treating diseases and conditions wherein inhibition of HDAC and/or activation of Nrf and HIF provides a benefit, such as a cancer, a neurological disease, a neurodegenerative disorder, a peripheral neuropathy, stroke, hypertension, an inflammation, traumatic brain injury, rheumatoid arthritis, allograft rejection, autoimmune diseases, and malaria, comprising administering a therapeutically effective amount of a present compound to an individual in need thereof. The present invention also relates to a method of increasing the sensitivity of a cancer cell to radiotherapy and/or chemotherapy. The present invention further allows for the use of a present compound in combination with other drugs and/or therapeutic approaches. The present compounds exhibit selectivity for particular HDAC isozymes, such as HDAC6, over other HDAC isozymes.

More particularly, the present invention relates to HDACIs having a structural formula:

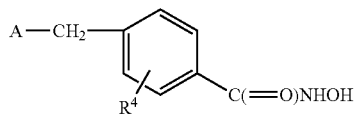

wherein A is

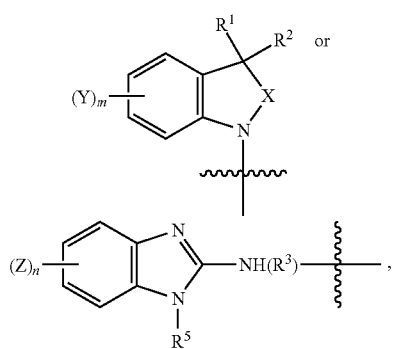

wherein X is —$CH_2$— or

Y, independently, is selected from the group consisting of halo, —OH, —CN, —$NO_2$, $C_{1-6}$alkyl, aryl, heteroaryl, —$OR^a$, —$N(R^a)_2$, —$NHR^a$, —CO—$N(R^a)_2$, —NHCO—$R^a$, —$CO_2R^a$, —$SR^a$, —$OCOR^a$, —$NHSO_2R^a$, —$SO_2N(R^a)_2$, and —$SO_2R^a$; or two Y groups, positioned ortho to one another, are taken together with the carbon atoms to which they are attached to form a five or six-membered carbocyclic ring or a five or six-membered heterocyclic ring containing one or two heteroatoms selected from O, S, and $NR^a$;

m is an integer 0, 1, 2, 3, or 4;

Z, independently, is selected from the group consisting of halo, —OH, —CN, —$NO_2$, $C_{1-6}$alkyl, aryl, heteroaryl, —$OR^a$, —$N(R^a)_2$, —$NHR^a$, —CO—$N(R^a)_2$, —NHCO—$R^a$, —$CO_2R^a$, —$SR^a$, —$OCOR^a$, —$NHSO_2R^a$, —$SO_2N(R^a)_2$, and —$SO_2R^a$; or two Z groups, positioned ortho to one another, are taken together with the carbon atoms to which they are attached to form a five or six-membered carbocyclic ring or a five or six-membered heterocyclic ring containing one or two heteroatoms selected from O, S, and $NR^a$;

n is an integer 0, 1, 2, 3, or 4;

$R^1$ and $R^2$, independently, are hydrogen, halo, or $C_{1-6}$alkyl, or $R^1$ is a five- or six-membered nitrogen-containing ring and $R^2$ is hydrogen, halo, or $C_{1-6}$alkyl, or $R^1$ and $R^2$ are taken together with the carbon atoms to which they are attached to form a three to six-membered carbocyclic ring or heterocyclic ring;

$R^a$ is hydrogen, $C_{1-6}$alkyl, aryl, or heteroaryl;

$R^3$ is hydrogen, $C_{1-6}$alkyl, —$CH_2$aryl, aryl, or heteroaryl;

$R^4$ is hydrogen or halo; and $R^5$ is $C_{1-3}$alkyl or aryl;

or a pharmaceutically acceptable salt thereof.

In another embodiment, the present invention provides a method of treating a condition or disease by administering a therapeutically effective amount of a present compound to an individual in need thereof. The disease or condition of interest is treatable by inhibition of HDAC and/or activation of Nrf2 and HIF, for example, a cancer, a neurodegenerative disorder, a traumatic brain injury, a neurological disease, peripheral neuropathy, an inflammation, stroke, hypertension, an autoimmune disease, allograft rejection, and malaria.

Another embodiment of the present invention provides a method of treating a cancer comprising administering to an individual in need thereof, such as a human, a therapeutically effective amount of a present compound. A present compound can be administered as the sole anticancer therapy, or in conjunction with a therapeutically effective amount of a second anticancer agent, such as radiation and/or chemotherapy.

Another embodiment of the present invention provides a method of increasing the sensitivity of a cancer cell to the cytotoxic effects of radiotherapy and/or chemotherapy comprising contacting the cell with an effective amount of a present compound. In certain embodiments, the cell is an in vivo cell.

In another embodiment, the present invention provides a method of treating a neurological disease comprising administering to an individual in need thereof, such as a human, a therapeutically effective amount of a present compound. The present invention also relates to a method of treating neurodegenerative disorders, peripheral neuropathies, and traumatic brain injuries comprising administering a therapeutically effective amount of an compound to an individual in need thereof. In each embodiment, a present compound can be the sole therapeutic agent or can be administered with additional therapeutic agents known to treat the disease or condition of interest.

The present invention also provides a method of treating malaria and other parasitic infections comprising administering a therapeutically effective amount of a present compound to an individual in need thereof. In certain embodiments, the individual is a human. In certain embodiments, said method further comprises optionally coadministering a second antimalarial compound (e.g., chloroquine).

In yet another embodiment, the present invention provides a method of inducing immunosuppression in an individual comprising administration of a therapeutically effective amount of a present compound to an individual in need thereof, for example, an individual receiving a transplant. This method further comprises optionally coadministering a second immunosuppressant (e.g., cyclosporin) or therapeutic agent.

In still another embodiment, the present invention provides a method of treating inflammatory diseases and conditions, e.g., arthritis and rheumatic diseases, comprising administration of a therapeutically effective amount of a present compound to an individual in need thereof. The method further contemplates optional coadministration of a second anti-inflammatory drug or therapeutic agent.

In another embodiment, the present invention also provides a pharmaceutical composition comprising a present compound and a pharmaceutically acceptable excipient.

Another embodiment of the present invention is to utilize a present compound and an optional second therapeutically active agent in a method of treating an individual for a disease or condition wherein inhibition of HDAC and/or activation of Nrf2 and HIF provides a benefit.

In a further embodiment, the invention provides for use of a composition comprising a present compound and an optional second therapeutic agent for the manufacture of a medicament for treating a disease or condition of interest, e.g., a cancer, neurodegeneration, or autoimmunity.

Still another embodiment of the present invention is to provide a kit for human pharmaceutical use comprising (a) a container, (b1) a packaged composition comprising a present compound, and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition of interest.

A present compound and the second therapeutic agent can be administered together as a single-unit dose or separately as multi-unit doses, wherein a present compound is administered before the second therapeutic agent, or vice versa. It is envisioned that one or more dose of a present compound and/or one or more dose of a second therapeutic agent can be administered.

In one embodiment, a present compound and a second therapeutic agent are administered simultaneously. In related embodiments, a present compound and second therapeutic agent are administered from a single composition or from separate compositions. In a further embodiment, a present compound and a second therapeutic agent are administered sequentially. A present compound can be administered in an amount of about 0.005 to about 500 milligrams per dose, about 0.05 to about 250 milligrams per dose, or about 0.5 to about 100 milligrams per dose.

Compounds of the invention inhibit HDAC and/or activate Nrf2 and HIF and are useful research tools for in vitro study of histone deacetylases and their role in biological processes. In preferred embodiments, the present compounds inhibit HDAC and activate Nrf2 and HIF.

These and other novel aspects of the present invention will become apparent from the following detailed description of the preferred embodiments.

DETAILED DESCRIPTION OF THE PREFERRED EMBODIMENTS

Figure 1:
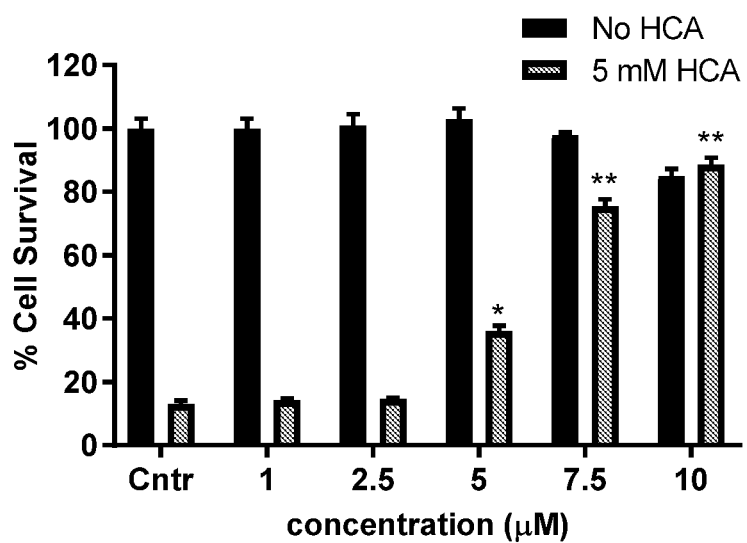
FIG. 1 contains bar graphs of % cell survival vs. concentration for HCA evaluation of II-ING-66 using the glutathione depletion neurotoxicity model of oxidative stress. Immature primary cortical neurons were treated with the test compound alone or in the presence of HCA. Cell viability was assessed at 24 h using the MTT assay. Bar plot represents percentage control mean±SEM of viable cells (n=3). *$p<0.05$ and **$p<0.01$ compared to control (DMSO) (n=3/group). HCA oxidative stress assay.

The present invention is directed to novel compounds and their use in therapeutic treatments of, for example, cancers, inflammations, traumatic brain injuries, neurodegenerative disorders, neurological diseases, peripheral neuropathies, strokes, hypertension, autoimmune diseases, inflammatory diseases, and malaria. The present compounds also increase the sensitivity of a cancer cell to the cytotoxic effects of radiotherapy and/or chemotherapy. In some embodiments, the present compounds selectively inhibit HDAC6 over other HDAC isozymes and activate Nrf2 and HIF.

Growing evidence shows that inhibition of HDAC6 promotes survival and regeneration of neurons, and enhances learning and memory in the CNS. Therefore, activation of Nrf2 and HIF in combination with inhibition of HDAC can provide to a comprehensive, safe, and durable therapeutic strategy. The present Nrf2 and HIF activators/HDAC inhibitors can cross the blood brain barrier (BBB) and normalize the redox-imbalance to reverse the progression of neurodegenerative diseases.

In most cases, HDACIs in clinical development for cancer treatment broadly and nonselectively inhibit class I/II HDACs with varying efficiency, which can cause serious problems in a clinical setting, especially in the treatment of diseases and conditions wherein a prolonged drug administration of an HDACI is required. Further, only a few reported HDACIs are able to cross the BBB. The present compounds are selective HDAC6 inhibitors with acceptable ADMET properties (ACD calculations) and exhibit a measured concentration in the brain as high as 1,700 ng/g following an iv administration of the compound at a 10 mg/kg dose.

The combined properties of the present compounds are beneficial in the treatment of a variety of diseases and conditions, for example, cancers, neurological diseases, neurodegenerative conditions, peripheral neuropathies, autoimmune diseases, inflammatory diseases and conditions, and stroke. To date, there are only three HDAC inhibitors on market, including VPA, SAHA, and Romidepsin, and only one Nrf2 activator, i.e., dimethyl fumarate BG-12, for the treatment of multiple sclerosis.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "a disease or condition wherein inhibition of HDAC and/or activation of Nrf2 and HIF provides a benefit" pertains to a condition in which HDAC or the action of HDAC is important or necessary and/or in which Nrf2 and HIF or the action of Nrf2 and HIF, e.g., for the onset, progress, expression of that disease or condition, or a disease or a condition which is known to be treated by an HDAC inhibitor (such as, e.g., TSA, pivalolyloxymethylbutane (AN-9; Pivanex), FK-228 (Depsipeptide), PXD-101, NVP-LAQ824, SAHA, MS-275, and MGCD0103) and/or an Nrf2 and HIF activation (such as dimethyl fumarate BG-12). Examples of such conditions include, but are not limited to, cancer, psoriasis, fibroproliferative disorders (e.g., liver fibrosis), smooth muscle proliferative disorders (e.g., atherosclerosis, restenosis), neurodegenerative diseases (e.g., Alzheimer's, Parkinson's, Huntington's chorea, amyotropic lateral sclerosis, spino-cerebellar degeneration, Rett syndrome), peripheral neuropathies (Charcot-Marie-Tooth disease, Giant Axonal Neuropathy (GAN)), inflammatory diseases (e.g., osteoarthritis, rheumatoid arthritis, colitis), diseases involving angiogenesis (e.g., cancer, rheumatoid arthritis, psoriasis, diabetic retinopathy), hematopoietic disorders (e.g., anemia, sickle cell anemia, thalasseimia), fungal infections, parasitic infections (e.g., malaria, trypanosomiasis, helminthiasis, protozoal infections), bacterial infections, viral infections, and conditions treatable by immune modulation (e.g., multiple sclerosis, autoimmune diabetes, lupus, atopic dermatitis, allergies, asthma, allergic rhinitis, inflammatory bowel disease; and for improving grafting of transplants). One of ordinary skill in the art is readily able to determine whether a compound treats a disease or condition mediated by HDAC and/or Nrf2 and HIF for any particular cell type, for example, by assays which conveniently can be used to assess the activity of particular compounds.

The term "second therapeutic agent" refers to a therapeutic agent different from a present compound and that is known to treat the disease or condition of interest. For example, when a cancer is the disease or condition of interest, the second therapeutic agent can be a known chemotherapeutic drug, like taxol, or radiation, for example.

The term "HDAC" refers to a family of enzymes that remove acetyl groups from a protein, for example, the ε-amino groups of lysine residues at the N-terminus of a histone. The HDAC can be a human HDAC, including, HDAC1, HDAC2, HDAC3, HDAC4, HDAC5, HDAC6, HDAC7, HDAC8, HDAC9, HDAC10, and HDAC11. The HDAC also can be derived from a protozoal or fungal source.

As used herein, the terms "treat," "treating," "treatment," and the like refer to eliminating, reducing, relieving, reversing, and/or ameliorating a disease or condition and/or symptoms associated therewith. Although not precluded, treating a disease or condition does not require that the disease, condition, or symptoms associated therewith be completely eliminated, including the treatment of acute or chronic signs, symptoms and/or malfunctions. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition, "treatment" therefore also includes relapse prophylaxis or phase prophylaxis. The term "treat" and synonyms contemplate administering a therapeutically effective amount of a compound of the invention to an individual in need of such treatment. A treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that, when administered, is (are) sufficient, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce HDAC signaling and/or increase Nrf2 and HIF signaling in the target cells; and/or relieve, to some extent, one or more of the symptoms associated with the cancer. To extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a present compound can be administered at the same time or sequentially in any order at different points in time as a second therapeutic agent. A present compound and the second therapeutic agent can be administered separately, in any appropriate form and by any suitable route. When a present compound and the second therapeutic agent are not administered concurrently, it is understood that they can be administered in any order to a subject in need thereof. For example, a present compound can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a present compound and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein merely serve as a shorthand method of referring individually to each separate value falling within the range, unless otherwise indicated herein, and each separate value and subrange is incorporated into the specification as if it were individually recited herein. The use of any and all examples, or exemplary language (e.g., "such as" and "like") provided herein, is intended to better illustrate the invention and is not a limitation on the scope of the invention unless otherwise claimed. No language in the specification should be construed as indicating any non-claimed element as essential to the practice of the invention.

In particular, the present invention is directed to compounds, compositions comprising a present compound, and therapeutic uses of the compounds of the following structural formula:

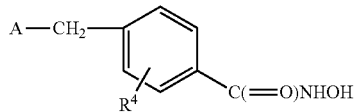

wherein A is

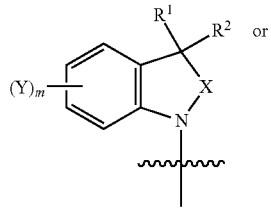

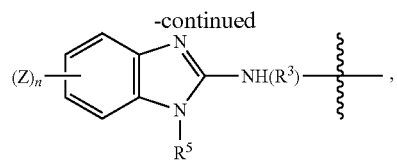

wherein X is —CH$_2$— or

Y, independently, is selected from the group consisting of halo, —OH, —CN, —NO$_2$, C$_{1-6}$alkyl, aryl, heteroaryl, —OR$^a$, —N(R$^a$)$_2$, —NHR$^a$, —CO—N(R$^a$)$_2$, —NHCO—R$^a$, —CO$_2$R$^a$, —SR$^a$, —OCOR$^a$, —NHSO$_2$R$^a$, —SO$_2$N(R$^a$)$_2$, and —SO$_2$R$^a$; or two Y groups, positioned ortho to one another, are taken together with the carbon atoms to which they are attached to form a five or six-membered carbocylic ring or a five or six-membered heterocyclic ring containing one or two heteroatoms selected from O, S, and NR$^a$;

m is an integer 0, 1, 2, 3, or 4;

Z, independently, is selected from the group consisting of halo, —OH, —CN, —NO$_2$, C$_{1-6}$alkyl, aryl, heteroaryl, —OR$^a$, —N(R$^a$)$_2$, —NHR$^a$, —CO—N(R$^a$)$_2$, —NHCO—R$^a$, —CO$_2$R$^a$, —SR$^a$, —OCOR$^a$, —NHSO$_2$R$^a$, —SO$_2$N(R$^a$)$_2$, and —SO$_2$R$^a$; or two Z groups, positioned ortho to one another, are taken together with the carbon atoms to which they are attached to form a five or six-membered carbocylic ring or a five or six-membered heterocyclic ring containing one or two heteroatoms selected from O, S, and NR$^a$;

n is an integer 0, 1, 2, 3, or 4;

R$^1$ and R$^2$, independently, are hydrogen, halo, or C$_{1-6}$alkyl, or R$^1$ is a five- or six-membered nitrogen-containing ring and R$^2$ is hydrogen, halo, or C$_{1-6}$alkyl, or R$^1$ and R$^2$ are taken together with the carbon atoms to which they are attached to form a three to six-membered carbocyclic ring or heterocyclic ring;

R$^a$ is hydrogen, C$_{1-6}$alkyl, aryl, or heteroaryl;

R$^3$ is hydrogen, C$_{1-6}$alkyl, —CH$_2$aryl, aryl, or heteroaryl;

R$^4$ is hydrogen or halo; and

R$^5$ is C$_{1-3}$methyl or aryl;

or a pharmaceutically acceptable salt thereof.

Compounds of the present invention inhibit HDAC and activate Nrf2 and HIF, and are useful in the treatment of a variety of diseases and conditions. In particular, the present compounds are used in methods of treating a disease or condition wherein inhibition of HDAC and/or activation of Nrf2 and HIF provides a benefit, for example, cancers, neurological diseases, neurodegenerative conditions, peripheral neuropathies, autoimmune diseases, inflammatory diseases and conditions, stroke, hypertension, traumatic brain injury, autism, and malaria. The methods comprise administering a therapeutically effective amount of a present compound to an individual in need thereof.

The present methods also encompass administering a second therapeutic agent to the individual in addition to a present compound. The second therapeutic agent is selected from agents, such as drugs and adjuvants, known as useful in treating the disease or condition afflicting the individual, e.g., a chemotherapeutic agent and/or radiation known as useful in treating a particular cancer.

As used herein, the term "alkyl" refers to straight chained and branched saturated hydrocarbon groups, nonlimiting examples of which include methyl, ethyl, and straight chain and branched propyl, butyl, pentyl, and hexyl groups containing the indicated number of carbon atoms. The term $C_n$ means the alkyl group has "n" carbon atoms.

As used herein, the term "halo" is defined as fluoro, chloro, bromo, and iodo.

The term "hydroxy" is defined as —OH.

The term "alkoxy" is defined as —OR, wherein R is alkyl.

The term "amino" is defined as —NR$_2$, wherein each R group, independently, is hydrogen, alkyl, cycloalkyl, heteroaryl, or aryl, or both R groups are taken together with the N to which they are attached to form a 4 to 8 membered ring.

The term "nitro" is defined as —NO$_2$.

The term "cyano" is defined as —CN.

The term "trifluoromethyl" is defined as —CF$_3$.

The term "trifluoromethoxy" is defined as —OCF$_3$.

The term "OBn" is defined as

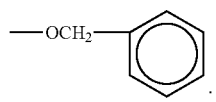

As used herein, compounds such as

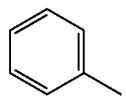

is an abbreviation for

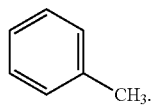

In addition, compounds such as

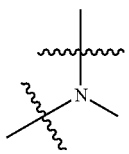

is an abbreviation for

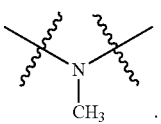

As used herein, a group such as

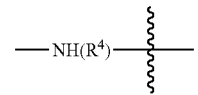

indicates the point of attachment of the group to the remainder of the molecule.

As used herein, the term "aryl" refers to a monocyclic aromatic group, e.g., phenyl. Unless otherwise indicated, an aryl group can be unsubstituted or substituted with one or more, and in particular one to five, groups independently selected from, for example, halo, alkyl, —OCF$_3$, —NO$_2$, —CN, —NC, —OH, alkoxy, amino, alkylamino, —CO$_2$H, —CO$_2$alkyl, cycloalkyl, imino, amido, trifluoromethyl, aryl, and heteroaryl. Exemplary aryl groups include, but are not limited to, phenyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic ring system containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, —OCF$_3$, —NO$_2$, —CN, —OH, alkoxy, amino, alkylamino, —CO$_2$H, —CO$_2$alkyl, cycloalkyl, trifluoromethyl, aryl, and heteroaryl. Examples of heteroaryl groups include, but are not limited to, thienyl, furyl, oxazolyl, thiophenyl, triazolyl, isothiazolyl, isoxazolyl, imidazolyl, pyrimidinyl, thiazolyl, thiadiazolyl, pyridinyl, pyridazinyl, pyrazolyl, pyrazinyl, tetrazolyl, oxazolyl, pyrrolyl, and triazinyl.

As used herein, the term "cycloalkyl" means a monocyclic aliphatic ring containing three to eight carbon atoms, either saturated or unsaturated.

As used herein, the term "heterocyclic" means a monocyclic aliphatic ring containing 3 to 6 total atoms, either saturated or partially unsaturated, of which one of the atoms is independently selected from nitrogen, oxygen, and sulfur and the remaining atoms are carbon. In a preferred embodiment, the heteroatom is nitrogen. Examples of heterocycles include, but are not limited to

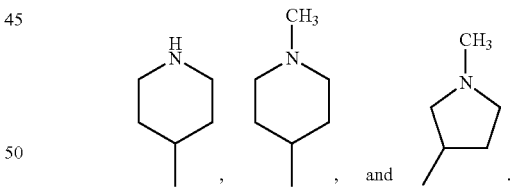

In some embodiments, Y is null (i.e., m=0), Cl, F, —OCH$_3$, —OBn, —NO$_2$, —N(CH$_3$)$_2$, —NHSO$_2$CH$_3$, —SCH$_3$, —C$_6$H$_5$,

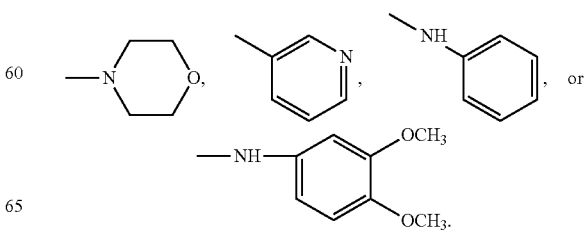

In another embodiment, two Y groups ortho to one another are taken together to form

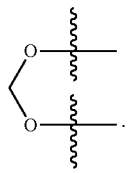 [SMILES: *OCO*]

In some embodiments, m is 0, 1, or 2. In other embodiments, m is 2 and each Y is halo, e.g., F and Cl.

In some embodiments, $R^1$ and $R^2$ each hydrogen, each are methyl, each are fluoro, or are taken together to form a cyclopropyl group.

In some embodiments, Z is null (i.e., n=0), —Cl, —OCH$_3$.

In other embodiments, $R^3$ is H, —CH$_3$, or —CH$_2$C$_6$H$_5$.

In various embodiments, $R^4$ is H or F.

In yet other embodiments, $R^5$ is —CH$_3$ or —C$_6$H$_5$

Additionally, salts, prodrugs, hydrates, isotopically labeled, fluorescently labeled and any other therapeutically or diagnostically relevant derivations of the present compounds also are included in the present invention and can be used in the methods disclosed herein. The present invention further includes all possible stereoisomers and geometric isomers of the present compounds. The present invention includes both racemic compounds and optically active isomers. When a present compound is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of a present compound is possible, the present invention is intended to include all tautomeric forms of the compounds.

Prodrugs of the present compounds also are included in the present invention. It is well established that a prodrug approach, wherein a compound is derivatized into a form suitable for formulation and/or administration, then released as a drug in vivo, has been successfully employed to transiently (e.g., bioreversibly) alter the physicochemical properties of the compound (see, H. Bundgaard, Ed., "Design of Prodrugs," Elsevier, Amsterdam, (1985); R. B. Silverman, "The Organic Chemistry of Drug Design and Drug Action," Academic Press, San Diego, chapter 8, (1992); K. M. Hillgren et al., Med. Res. Rev., 15, 83 (1995)). Specific prodrugs of HDACIs are discussed in WO 2008/055068, incorporated in its entirety herein by reference.

Compounds of the present invention can contain one or more functional groups. The functional groups, if desired or necessary, can be modified to provide a prodrug. Suitable prodrugs include, for example, acid derivatives, such as amides and esters. It also is appreciated by those skilled in the art that N-oxides can be used as a prodrug.

Compounds of the invention can exist as salts. Pharmaceutically acceptable salts of the present compounds often are preferred in the methods of the invention. As used herein, the term "pharmaceutically acceptable salts" refers to salts or zwitterionic forms of the present compounds. Salts of the present compounds can be prepared during the final isolation and purification of the compounds or separately by reacting the compound with an acid having a suitable cation. The pharmaceutically acceptable salts of the present compounds can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, tartaric, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphosphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and stearyl chlorides, bromides, and iodides; and benzyl and phenethyl bromides. In light of the foregoing, any reference to compounds of the present invention appearing herein is intended to include the present compounds as well as pharmaceutically acceptable salts, hydrates, or prodrugs thereof.

The present compounds also can be conjugated or linked to auxiliary moieties that promote a beneficial property of the compound in a method of therapeutic use. Such conjugates can enhance delivery of the compounds to a particular anatomical site or region of interest (e.g., a tumor), enable sustained therapeutic concentrations of the compounds in target cells, alter pharmacokinetic and pharmacodynamic properties of the compounds, and/or improve the therapeutic index or safety profile of the compounds. Suitable auxiliary moieties include, for example, amino acids, oligopeptides, or polypeptides, e.g., antibodies, such as monoclonal antibodies and other engineered antibodies; and natural or synthetic ligands to receptors in target cells or tissues. Other suitable auxiliaries include fatty acid or lipid moieties that promote biodistribution and/or uptake of the compound by target cells (see, e.g., Bradley et al., *Clin. Cancer Res.* (2001) 7:3229).

Specific compounds of the present invention include, but are not limited to,

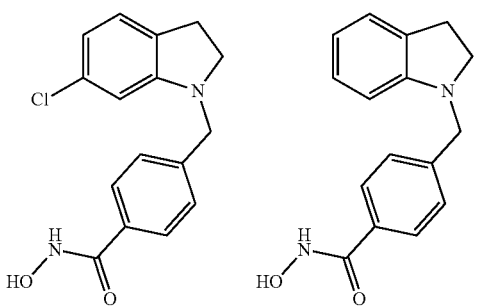

21
-continued
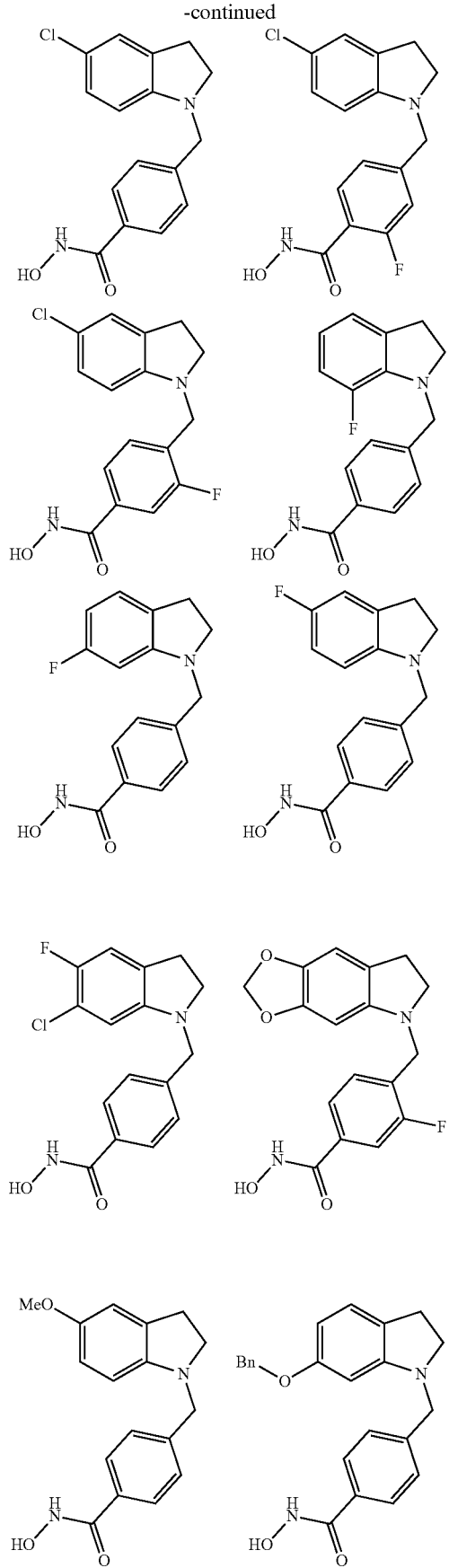
22
-continued
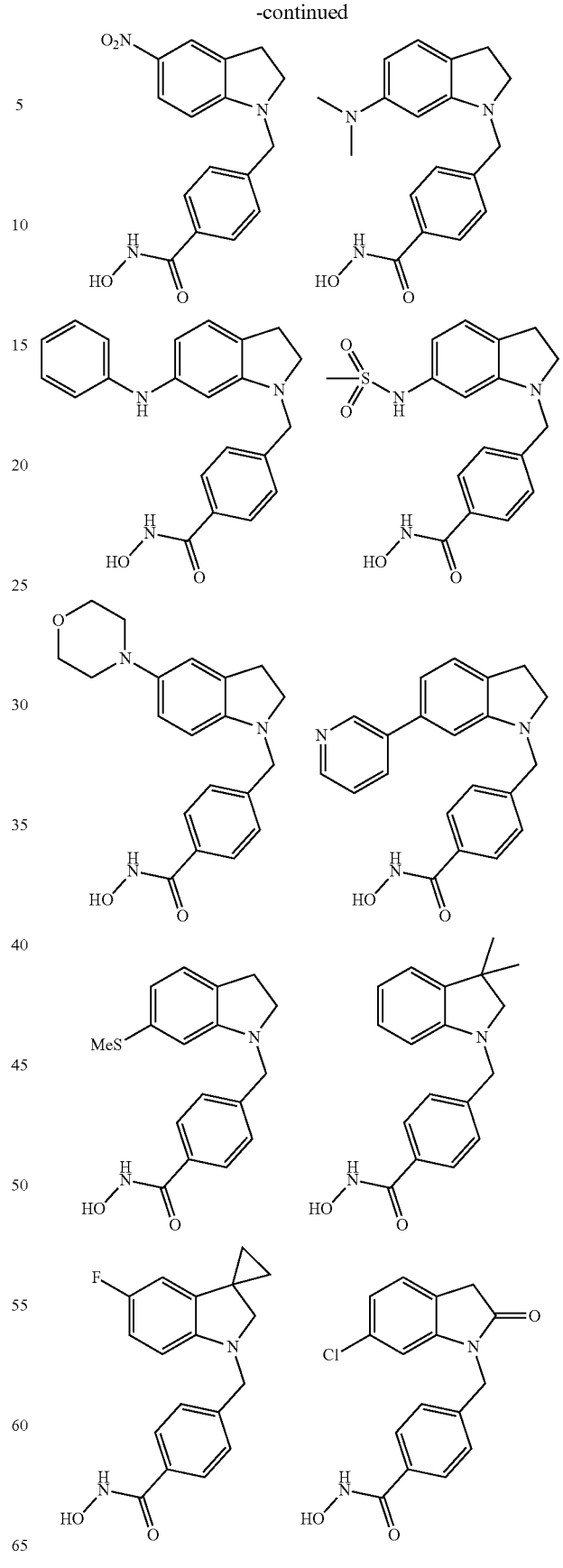

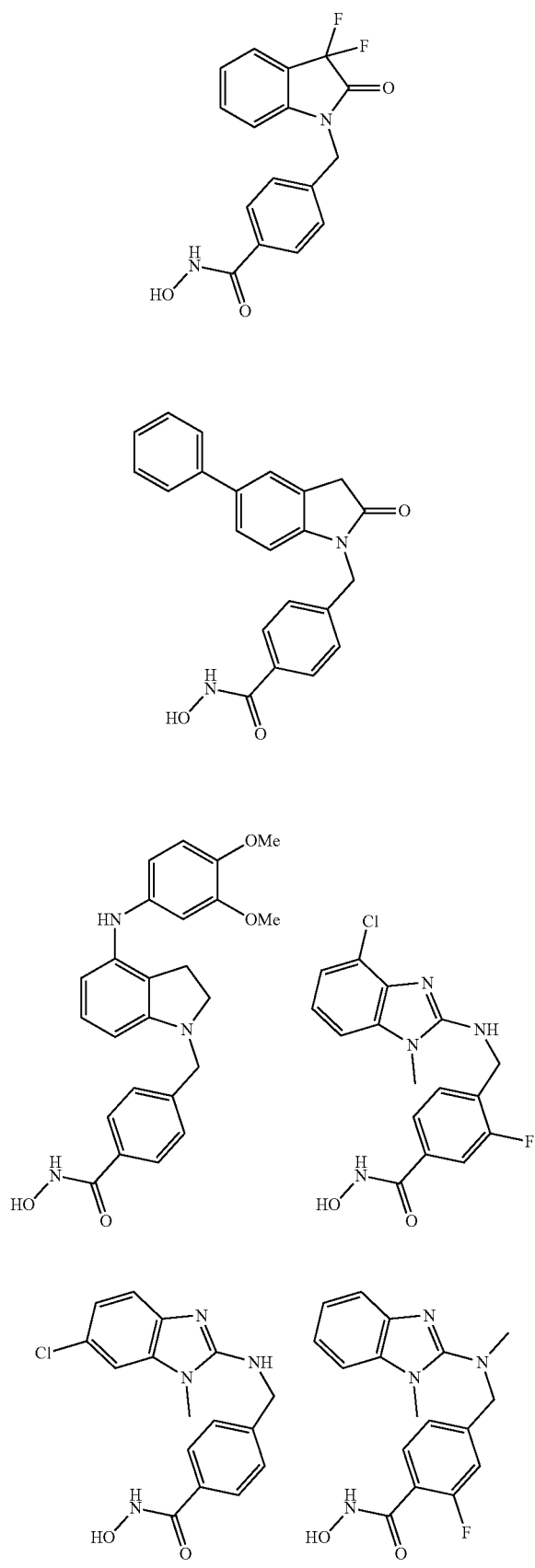
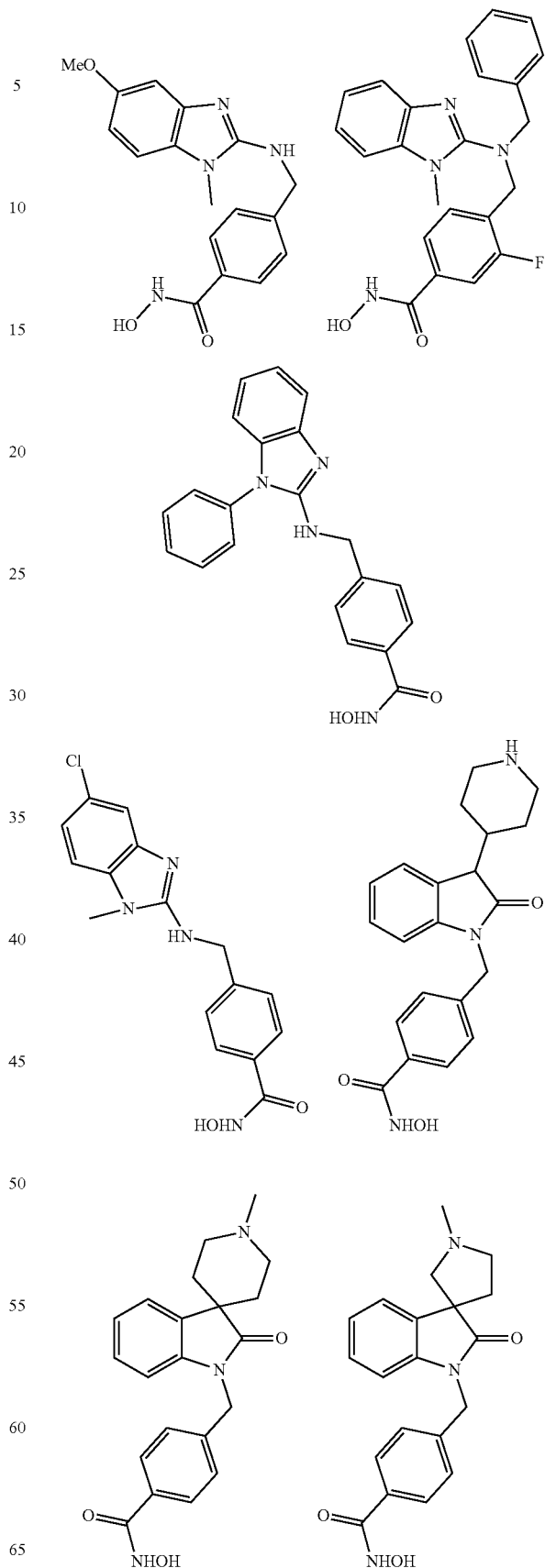

-continued

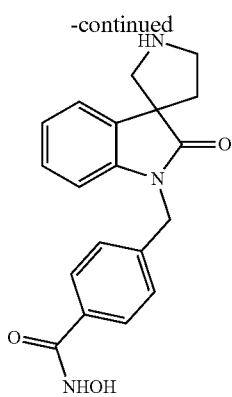

Synthetic Methods

The following synthetic schemes are representative of the reactions used to synthesize the present compounds. Modifications and alternate schemes to prepare compounds of the invention are readily within the capabilities of persons skilled in the art.

In the synthetic methods, the examples, and throughout the specification, the abbreviations have the following meanings:

| | |
|---|---|
| DMF | dimethylformamide |
| min | minutes |
| TLC | thin layer chromatography |
| CH$_2$Cl$_2$ | methylene chloride |
| MeOH | methanol |
| Na$_2$SO$_4$ | sodium sulfate |
| MS | mass spectrometry |
| Na$_2$CO$_3$ | sodium carbonate |
| HPLC | high performance liquid chromatography |
| H or hrs | hours |
| HCl | hydrochloric acid |
| g | gram |
| mol | mole |
| mmol | millimole |
| mL | milliliter |
| TMS | tetramethylsilane |
| TFA | trifluoroacetic acid |
| KOH | potassium hydroxide |
| NH$_4$Cl | ammonium chloride |
| NH$_2$OH•HCl | hydroxylamine hydrochloride |
| CD$_3$OD | deuterated methanol |
| M | molar |
| DMSO | dimethyl sulfoxide |
| NaCNBH$_3$ | sodium cyanoborohydroxide |
| N | normal |
| CD$_3$CN | deuterated acetonitrile |
| RT or rt | room temperature |
| NMR | nuclear magnetic resonance spectrometry |
| EtOAc | ethyl acetate |
| THF | tetrahydrofuran |
| NaOH | sodium hydroxide |
| CDCl$_3$ | deuterated chloroform |
| Hz | Hertz |

It should be understood that protecting groups can be utilized in accordance with general principles of synthetic organic chemistry to provide compounds of the present invention. Protecting group-forming reagents are well known to persons skilled in the art, for example, see T. W. Greene et al., "Protective Groups in Organic Synthesis, Third Edition," John Wiley and Sons, Inc., NY, N.Y. (1999). These protecting groups are removed when necessary by appropriate basic, acidic, or hydrogenolytic conditions known to persons skilled in the art. Accordingly, compounds of the present invention not specifically exemplified herein can be prepared by persons skilled in the art.

Synthetic Methods and Procedures

Procedures

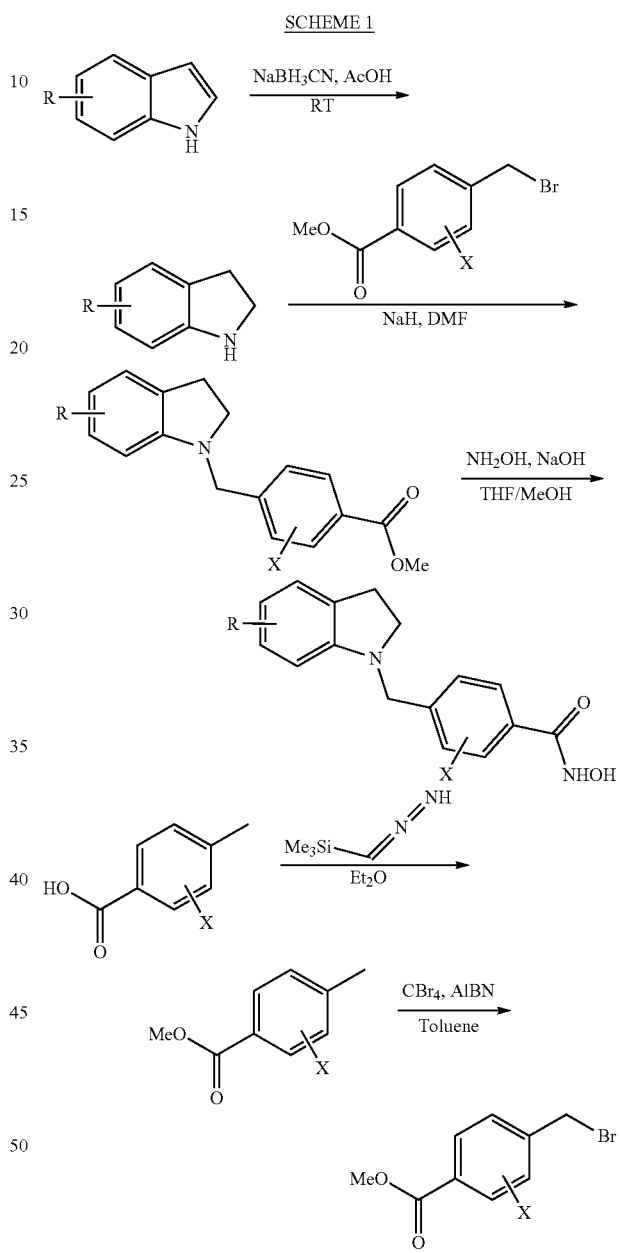

SCHEME 1

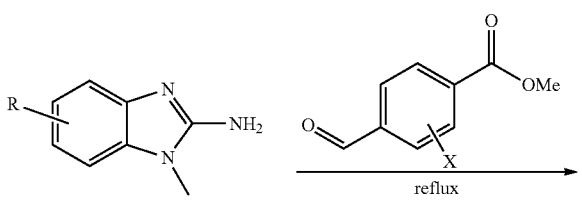

SCHEME 2

-continued

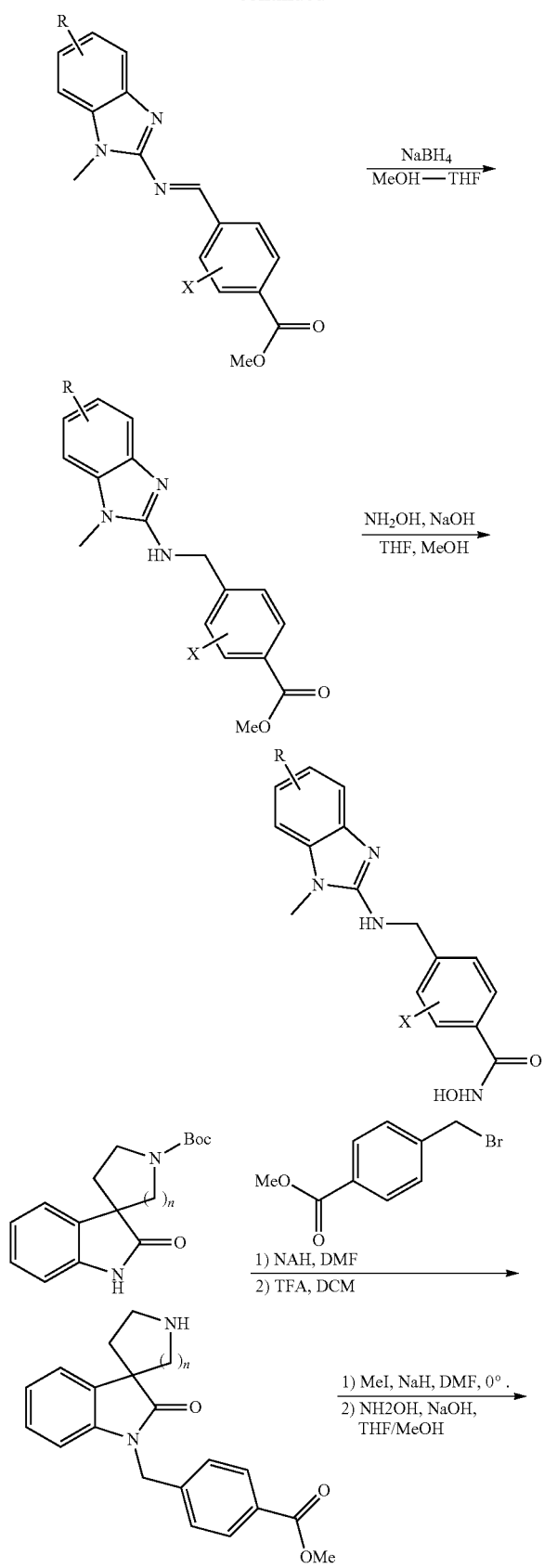

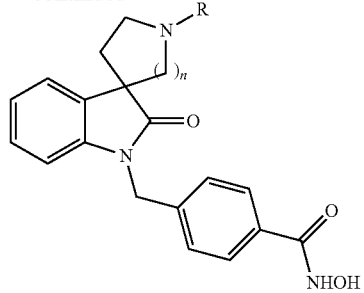

Analytical Data $^1$H NMR and $^{13}$C NMR spectra were recorded on Bruker spectrometer at 400 MHz and 100 MHz respectively with TMS as an internal standard. Standard abbreviations indicating multiplicity were used as follows: s=singlet, b.s=broad singlet, d=doublet, t=triplet, q=quadruplet, and m=multiplet. HRMS experiments were performed on LTO-FTICR or Shimadzu IT-TOF Mass Spectrometers. TLC was performed with Merck 250-mm 60F$_{254}$ silica gel plates. Preparative TLC was performed with Analtech 1000-mm silica gel GF plates. Column chromatography was performed using Merck silica gel (40-60 mesh). Analytical HPLC was carried out on an Ace 3AQ column (100×4.6 mm), with a Shimadzu 10 VP Series HPLC with a diode array detector; flow rate=2.0 mL/min; from 10% acetonitrile in water to 50% in 10 min and to 100% acetonitrile in 5 min with 0.05% TFA (Method A), or from 30% acetonitrile in water to 100% of acetonitrile in 15 min with 0.05% TFA (Method B) or from 30% acetonitrile in water to 100% of acetonitrile in 30 min with 0.05% TFA (Method C), a column Ace AQ5 (250×10 mm) was used with this last method.

General Procedure A:

To a solution of indole (1 eq) NaBH$_3$CN (3 eq) was added in one portion. The reaction mixture was stirring at RT for 0.5-1 h, then cooled at 0° C. and quenched by addition of water. The resulting mixture was extracted with ethyl acetate, the combined organic phases were washed with NaOH (1N), Na$_2$CO$_3$, and brine, and dried over Na$_2$SO$_4$. After evaporation, the residue was purified by column chromatography to provide indolines.

General Procedure B:

To a solution of indoline (1 eq) in DMF (2 ml per 1 mmol) 55% NaH (2 eq) was added at 0° C. The reaction mixture was stirred for 20 min, and methyl 4-(bromomethyl)benzoate (1 eq) was added. The reaction was quenched with 1N HCl and CH$_2$Cl$_2$ was added. The resulting solution was washed with water and brine, dried over Na$_2$SO$_4$, and evaporated. The residue was purified by column chromatography to provide ester.

General Procedure C:

To a stirred solution of NaOH (4 eq) in MeOH (3 ml per 2 mmol of NaOH) a solution of NH$_2$OH (50% sol. In water) was added at 0° C. After 10 min, a solution of ester (1 eq) in THF (3 ml) was added at 0° C. After 1-2 h, the reaction mixture was acidified with 1N HCl (pH~4). Ice and water were added and and a precipitate was formed. The precipitate was filtered and washed with H$_2$O and hexane. The sample was further purified by HPLC for biological test.

4-((6-Chloroindolin-1-yl)methyl)-N-hydroxybenzamide (II-ING-6)

$^1$H NMR (DMSO-d$_6$, 400 MHz) δ 2.88 (t, J=8.6 Hz, 2H), 3.34 (t, J=8.6 Hz, 2H), 4.32 (s, 2H), 6.53 (m, 3H), 6.98 (d,

J=7.5 Hz, 1H), 7.37 (d, J=8.0 Hz, 2H), 7.70 (d, J=8.0 Hz, 2H); $^{13}$C NMR (DMSO-d$_6$, 100 MHz)

δ 27.7, 53.9, 54.8, 110.5, 121.2, 125.6, 127.5, 128.7, 129.9, 130.2, 133.3, 139.8, 149.9, 160.9, 161.3, 166.3; FAB-HRMS calcd for C$_{16}$H$_{15}$C$_1$N$_2$O$_2$ [M+H]$^+$: 303.0895; found: 303.0889. HPLC (method 1) 97%.

4-((5-Chloroindolin-1-yl)methyl)-N-hydroxybenzamide (II-ING-39)

$^1$H NMR (DMSO-d$_6$, 400 MHz) δ 2.91 (t, J=8.3 Hz, 2H), 3.31 (t, J=8.3 Hz, 2H), 4.30 (s, 2H), 6.51 (d, J=8.3 Hz, 1H), 6.99 (dd, J=1.6, and 8.3 Hz, 1H), 7.06 (s, 1H), 7.38 (d, J=8.0 Hz, 2H), 7.71 (d, J=8.0 Hz, 2H); $^{13}$C NMR (DMSO-d$_6$, 100 MHz)

δ 28.1, 52.3, 53.3, 108.1, 120.9, 124.7, 127.0, 127.4, 128.2, 132.0, 132.4, 141.7, 151.4, 164.4; FAB-HRMS calcd for C$_{16}$H$_{15}$ClN$_2$O$_2$ [M+H]$^+$: 303.0895; found: 303.0903. HPLC (method 1) 98%.

4-((6-Fluoroindolin-1-yl)methyl)-N-hydroxybenzamide (II-ING-41)

$^1$H NMR (DMSO-d$_6$, 400 MHz) δ 2.91 (t, J=8.2 Hz, 2H), 3.43 (t, J=8.2 Hz, 2H), 4.38 (s, 2H), 6.29 (m, 2H), 7.00 (m, 1H), 7.47 (d, J=8.3 Hz, 2H), 7.83 (d, J=8.3 Hz, 2H); $^{13}$C NMR (DMSO-d$_6$, 100 MHz)

δ 27.3, 52.2, 53.7, 94.4, 94.7, 102.5, 102.7, 124.5, 124.6, 125.3, 127.0, 127.8, 131.1, 142.0, 1 54.0, 154.1, 162.2, 164.5; FAB-HRMS calcd for C$_{16}$H$_{15}$FN$_2$O$_2$ [M+H]$^+$: 287.1190; found: 287.1197. HPLC (method 1) 97%.

4-((5-Fluoroindolin-1-yl)methyl)-N-hydroxybenzamide (II-ING-42)

$^1$H NMR (Acetone-d$_6$, 400 MHz) δ 2.95 (t, J=8.2 Hz, 2H), 3.34 (t, J=8.2 Hz, 2H), 4.31 (s, 2H), 6.49 (m, 1H), 6.75 (m, 1H), 6.89 (dd, J=1.2, and 8.5 Hz, 1H), 7.49 (d, J=8.0 Hz, 2H), 7.82 (d, J=8.0 Hz, 2H); $^{13}$C NMR (Acetone-d$_6$, 100 MHz)

δ 24.8, 53.3, 53.6, 106.9, 107.0, 111.3, 111.5, 112.0, 112.3, 126.6, 127.5, 130.7, 131.6, 131.7, 141.9, 148.4, 154.9, 157.3, 164.3; FAB-HRMS calcd for C$_{16}$H$_{15}$FN$_2$O$_2$ [M+H]$^+$: 287.1190; found: 287.1200. HPLC (method 1) 98%.

N-Hydroxy-4-(indolin-1-ylmethyl)benzamide (II-ING-44)

$^1$H NMR (Acetone-d$_6$, 400 MHz) δ 2.96 (t, J=8.2 Hz, 2H), 3.38 (t, J=8.2 Hz, 2H), 4.38 (s, 2H), 6.60 (d, J=7.8 Hz, 1H), 6.68 (t, J=7.7 Hz, 1H), 7.03 (t, J=7.7 Hz, 1H), 7.08 (d, J=7.8 Hz, 1H), 7.49 (d, J=8.1 Hz, 2H), 7.83 (d, J=8.1 Hz, 2H); $^{13}$C NMR (Acetone-d$_6$, 100 MHz)

δ 28.1, 53.3, 107.9, 118.6, 124.4, 126.7, 127.10, 127.14, 128.1, 128.6, 130.2, 131.0, 142.1, 1 51.5, 164.9; FAB-HRMS calcd for C$_{16}$H$_{16}$N$_2$O$_2$ [M+H]$^+$: 269.1285; found: 269.1295. HPLC (method 1) 98%.

N-Hydroxy-4-((5-methoxyindolin-1-yl)methyl)benzamide (II-ING-49)

$^1$H NMR (DMSO-d$_6$, 400 MHz) δ 2.84 (t, J=8.0 Hz, 2H), 3.17 (t, J=8.0 Hz, 2H), 3.64 (s, 3H), 4.19 (s, 2H), 6.45 (d, J=8.2 Hz, 1H), 6.55 (d, J=8.2 Hz, 1H), 6.73 (s, 1H), 7.41 (d, J=7.8 Hz, 2H), 7.70 (d, J=7.8 Hz, 2H), 9.02 (s, 1H), 11.18 (s, 1H); $^{13}$C NMR (DMSO-d$_6$, 100 MHz)

δ 28.7, 54.0, 54.2, 55.9, 108.1, 112.0, 112.08, 127.3, 128.3, 131.6, 131.8, 142.3, 146.9, 152.8, 164.6; FAB-HRMS calcd for C$_{17}$H$_{18}$N$_2$O$_3$ [M+H]$^+$: 299.1390; found: 299.1398. HPLC (method 1) 98%.

4-((5-Chloroindolin-1-yl)methyl)-2-fluoro-N-hydroxybenzamide (II-ING-51)

$^1$H NMR (acetone-d$_6$, 400 MHz) δ 2.28 (t, J=8.3 Hz, 2H), 3.30 (t, J=8.3 Hz, 2H), 4.24 (s, 2H), 6.35 (d, J=8.4 Hz, 1H), 6.85 (dd, J=2.0, 8.2 Hz, 1H), 6.93 (s, 1H), 7.10 (d, J=12.1 Hz, 1H), 7.19 (d, J=7.6 Hz, 1H), 7.68 (t, J=7.2 Hz, 1H), 10.28 (s, 1H); $^{13}$C NMR (DMSO-d$_6$, 100 MHz)

δ 27.9, 52.3, 53.4, 107.8, 107.9, 115.0, 115.2, 121.9, 123.9, 124.5, 126.7, 130.7, 132.5, 150.8, 161.2, 161.4; FAB-HRMS calcd for C$_{16}$H$_{14}$ClFN$_2$O$_2$ [M+H]$^+$: 321.0801; found: 321.0811. HPLC (method 1) 98%.

4-((6-Chloro-5-fluoroindolin-1-yl)methyl)-N-hydroxybenzamide (II-ING-56)

$^1$H NMR (DMSO-d$_6$, 400 MHz) δ 2.50 (t, J=8.3 Hz, 2H), 3.28 (t, J=8.3 Hz, 2H), 4.30 (s, 2H), 6.64 (d, J=6.1 Hz, 1H), 7.10 (d, J=8.9 Hz, 1H), 7.38 (d, J=8.1 Hz, 2H), 7.71 (d, J=8.1 Hz, 2H), 11.20 (bs, 1H); $^{13}$C NMR (DMSO-d$_6$, 100 MHz)

δ 28.1, 52.5, 53.6, 107.3, 113.5, 113.7, 117.3, 117.5, 127.5, 128.2, 130.9, 131.0, 132.0, 141. 5, 149.4, 149.7, 151.7, 164.5; FAB-HRMS calcd for C$_{16}$H$_{14}$ClFN$_2$O$_2$ [M+H]$^+$: 321.0801; found: 321.0813: HPLC (method 1) %.

N-Hydroxy-4-((5-nitroindolin-1-yl)methyl)benzamide (II-ING-57)

$^1$H NMR (DMSO-d$_6$, 400 MHz) δ 3.08 (t, J=8.6 Hz, 2H), 3.65 (t, J=8.6 Hz, 2H), 4.58 (s, 2H), 6.58 (d, J=8.9 Hz, 1H), 7.35 (d, J=8.1 Hz, 2H), 7.72 (d, J=8.1 Hz, 2H), 7.84 (s, 1H), 7.97 (dd, J=2.2, 8.9 Hz, 1H), 11.20 (s, 1H); $^{13}$C NMR (DMSO-d$_6$, 100 MHz)

δ 26.8, 49.9, 52.4, 104.2, 120.7, 126.9, 127.6, 127.9, 130.7, 132.3, 137.1, 140.4, 157.5; FAB-HRMS calcd for C$_{16}$H$_{15}$N$_3$O$_4$ [M+H]$^+$: 314.1135; found: 314.1143. HPLC (method 1) 98.9%.

4-((6-(Benzyloxy)indolin-1-yl)methyl)-N-hydroxybenzamide (II-ING-61)

$^1$H NMR (DMSO-d$_6$, 400 MHz) δ 2.81 (t, J=8.0 Hz, 2H), 3.27 (t, J=8.0 Hz, 2H), 4.28 (s, 2H), 4.99 (s, 2H), 6.19 (d, J=7.8 Hz, 1H), 6.23 (s, 1H), 6.88 (d, J=7.8 Hz, 1H), 7.34 (m, 7H), 7.70 (d, J=8.0 Hz, 2H), 9.0 (b.s, 1H), 11.18 (s, 1H); $^{13}$C NMR (DMSO-d$_6$, 100 MHz)

δ 27.6, 52.3, 53.7, 69.6, 95.7, 103.1, 122.3, 124.8, 127.4, 127.9, 128.0, 128.2, 128.7, 131.9, 137.8, 142.0, 153.7, 159.9, 164.6; FAB-HRMS calcd for C$_{23}$H$_{22}$N$_2$O$_3$ [M−H]$^-$: 373.1558; found: 373.1562. HPLC (method 1) 98.2%.

4-((3,3-Dimethylindolin-1-yl)methyl)-N-hydroxybenzamide (II-ING-65)

$^1$H NMR (DMSO-d$_6$, 400 MHz) δ 1.22 (s, 6H), 3.04 (s, 2H), 4.30 (s, 2H), 6.51 (d, J=7.8 Hz, 1H), 6.62 (t, J=7.3 Hz, 1H), 6.97 (m, 2H), 7.39 (d, J=7.9 Hz, 2H), 7.71 (d, J=7.9 Hz, 2H), 11.15 (s, 1H); $^{13}$C NMR (DMSO-d$_6$, 100 MHz) 27.8, 52.2, 67.5, 107.4, 117.9, 122.0, 127.4, 127.6, 128.1, 131.9, 138.9, 142.2, 150.9, 164.5; FAB-HRMS calcd for C$_{18}$H$_{20}$N$_2$O$_2$ [M+H]$^+$: 297.1598; found: 297.1606. HPLC (method 1) 98.2%.

4-((3,3-Difluoro-2-oxoindolin-1-yl)methyl)-N-hydroxybenzamide (II-ING-66)

$^1$H NMR (DMSO-d$_6$, 400 MHz) δ 5.00 (s, 2H), 7.16 (d, J=7.7 Hz, 1H), 7.23 (t, J=7.6 Hz, 1H), 7.39 (d, J=7.9 Hz, 2H), 7.55 (t, J=7.6 Hz, 1H), 7.72 (d, J=7.9 Hz, 2H), 11.18 (s, 1H); $^{13}$C NMR (DMSO-d$_6$, 100 MHz) 43.3, 111.5, 111.6, 113.9, 118.9, 119.2, 119.4, 124.6, 125.2, 127.6, 127.9, 132.8, 134.7, 138.6, 143.2, 143.3, 143.4, 164.2, 164.7, 165.0, 165.3; FAB-HRMS calcd for C$_{16}$H$_{12}$N$_2$O$_3$F$_2$ [M+H]$^+$: 319.0889; found: 319.0904. HPLC (method 2) 97.6%.

4-((5'-Fluorospiro[cyclopropane-1,3'-indolin]-1'-yl)methyl)-N-hydroxybenzamide (II-ING-68)

$^1$H NMR (DMSO-d$_6$, 400 MHz) δ 0.94 (d, J=6.0 Hz, 4H), 4.32 (s, 2H), 6.51 (m, 2H), 6.73 (dt, J=2.5, and 9.0 Hz, 1H), 7.39 (d, J=8.0 Hz, 2H), 7.74 (d, J=8.0 Hz, 2H), 11.18 (s, 1H); $^{13}$C NMR (DMSO-d$_6$, 100 MHz) 16.6, 23.5, 23.6, 53.0, 61.5, 106.6, 106.9, 107.0, 107.1, 112.4, 112.6, 127.4, 128.3, 132.0, 137.2, 137.2, 141.9, 149.2, 155.4, 157.7, 158.8, 164.4; FAB-HRMS calcd for C$_{18}$H$_{17}$N$_2$O$_2$F [M+H]$^+$: 313.1347; found: 313.1359. HPLC (method 2) 97.4%.

N-Hydroxy-4-(((1-methyl-1H-benzo[d]imidazol-2-yl)amino)methyl)benzamide (II-ING-13)

(E)-methyl 4-(((1-methyl-1H-benzo[d]imidazol-2-yl)imino)methyl)benzoate: A mixture of 1-methyl-1H-benzo[d]imidazol-2-amine (0.20 g, 1.22 mmol) and methyl 4-formylbenzoate (0.17 g, 1.22 mmol) in 7 ml of toluene was refluxed for 6 h. The solvent was evaporated, and the product was dried in vacuo and used in next step. Methyl 4-(((1-methyl-1I-benzo[d]imidazol-2-yl)amino)methyl)benzoate: to a solution of the imine (0.36 g, 1.22 mmol) in 10 ml of a mixture of MeOH-THF (1:1) sodium borohydride (0.07 g, 1.82 mmol) was added at 0° C. The reaction mixture was stirred for 30 min, quenched with ice water, and extracted with ethyl acetate. Combined organic layer was washed with brine, dried over Na$_2$SO$_4$, and evaporated. The product was used in next step without additional purification.

The title compound was synthesized from ester and purified by prep HPLC (method 2) affording an off-white solid after lyophilization (47 mg, 31%). $^1$H NMR (DMSO-d$_6$, 400 MHz) δ 11.12 (s, 1H), 8.97 (s, 1H), 7.70 (d, J=8.3 Hz, 2H), 7.45 (d, J=8.3 Hz, 2H), 7.29 (t, J=6.0 Hz, 1H), 7.15 (m, 2H), 6.92 (m, 2H), 4.63 (d, J=5.9 Hz, 2H). $^{13}$C NMR (DMSO-d$_6$, 100 MHz) δ 166.2, 154.5, 143.2, 140.8, 134.3, 130.4, 126.6, 126.4, 120.3, 118.9, 114.2, 106.5, 45.2, 26.8. FAB-HRMS calcd for C$_{16}$H$_{16}$N$_4$O$_3$ [M+H]$^+$: 297.1346, found: 297.1352. HPLC (method 2): 99.9%.

4-(((5-chloro-1-methyl-1H-benzo[d]imidazol-2-yl)amino)methyl)-N-hydroxybenzamide (II-ING-85)

$^1$H NMR (MeOD, 400 MHz) δ 7.78 (d, J=8.2 Hz, 2H), 7.54 (d, J=8.2 Hz, 2H), 7.47 (d, J=8.6 Hz, 1H), 7.49 (d, J=1.8 Hz, 1H), 7.34 (dd, J=1.8, 8.6 Hz, 1H), 4.81 (s, 2H). $^{13}$C NMR (MeOD, 100 MHz) δ 166.1, 150.6, 139.5, 131.8, 130.3, 129.7, 129.1, 127.3, 126.9, 123.7, 111.3, 110.7, 46.0, 28.4. FAB-HRMS calcd for C$_{16}$H$_{15}$N$_4$O$_2$ Cl [M+H]$^-$: 329.0811, found: 329.0799. HPLC (method 2): 98.7%.

N-hydroxy-4-(((1-phenyl-1H-benzo[d]imidazol-2-yl)amino)methyl)benzamide (II-ING-87)

$^1$H NMR (MeOD, 400 MHz) δ 7.75 (m, 5H), 7.67 (m, 2H), 7.50 (m, 3H), 7.31 (m, 2H), 7.02 (d, J=8.1 Hz, 1H), 4.78 (s, 2H). $^{13}$C NMR (MeOD, 100 MHz) δ 166.1, 149.9, 139.8, 132.2, 131.2, 130.9, 130.8, 130.6, 130.5, 127.6, 127.3, 127.2, 126.6, 124.2, 124.0, 123.5, 111.5, 111.3, 109.8, 45.8. FAB-HRMS calcd for C$_{21}$H$_{18}$N$_4$O$_2$ [M+H]$^+$: 359.1503, found: 359.1518. HPLC (method 2): 99.8%.

3-((3,3-Difluoro-2-oxoindolin-1-yl)methyl)-N-hydroxybenzamide (II-ING-100)

$^1$H NMR (DMSO-d$_6$, 400 MHz) δ 4.99 (s, 2H), 7.15 (d, J=7.6 Hz, 1H), 7.23 (t, J=7.6 Hz, 1H), 7.46 (m, 2H), 7.55 (t, J=7.4 Hz, 1H), 7.64 (d, J=6.8 Hz, 1H), 7.72 (m, 2H), 9.04 (s, 1H), 11.24 (s, 1H); $^{13}$C NMR (DMSO-d$_6$, 100 MHz) δ 43.4, 111.5, 111.6, 119.0, 119.2, 119.4, 124.6, 125.2, 126.4, 126.6, 129.4, 1130.3, 133.9, 134.7, 135.9, 143.2, 143.3, 164.3, 164.7, 165.0, 165.3; FAB-HRMS calcd for C$_{16}$H$_{12}$N$_2$O$_3$F$_2$ [M+H]$^+$: 319.0889; found: 319.0875. HPLC (method 2) 99.2%.

4-((3,3-Dimethyl-2-oxoindolin-1-yl)methyl)-N-hydroxybenzamide (II-ING-101)

$^1$H NMR (DMSO-d$_6$, 400 MHz) δ 1.33 (s, 6H), 4.94 (s, 2H), 6.97 (d, J=7.5 Hz, 1H), 7.00 (t, J=7.5 Hz, 1H), 7.16 (t, J=7.5 Hz, 1H), 7.36 (m, 3H), 7.69 (d, J=8.1 Hz, 1H), 9.01 (s, 1H), 11.15 (s, 1H); $^{13}$C NMR (DMSO-d$_6$, 100 MHz) δ 26.6, 40.6, 43.9, 109.4, 122.8, 123.0, 127.4, 127.7, 128.0, 132.4, 135.7, 140.2, 141.6, 164.4, 180.9; FAB-HRMS calcd for C$_{18}$H$_{18}$N$_2$O$_3$ [M+H]$^+$: 311.1390; found: 311.1377. HPLC (method 1) 99.7%.

1-(4-(Hydroxycarbamoyl)benzyl)-1',1'-dimethyl-2-oxospiro[indoline-3,4'-piperidin]-1'-ium 1r (II-ING-109)

$^1$H NMR (DMSO-d$_6$, 400 MHz) δ 2.03 (d, J=15.2 Hz, 2H), 2.38 (t, J=2.2 Hz, 2H), 3.25 (s, 3H), 3.35 (s, 3H), 3.55 (d, J=13.0 Hz, 2H), 3.93 (t, J=11.3 Hz, 2H), 4.95 (s, 2H), 6.92 (d, J=7.5 Hz, 1H), 7.10 (t, J=7.5 Hz, 1H), 7.25 (t, J=7.5 Hz, 1H), 7.37 (d, J=8.2 Hz, 2H), 7.69 (d, J=8.2 Hz, 2H), 7.75 (d, J=7.5 Hz, 1H), 9.04 (s, 1H), 11.17 (s, 1H); $^{13}$C NMR (DMSO-d$_6$, 100 MHz) δ 27.3, 41.6, 42.4, 54.9, 57.7, 109.3, 122.7, 123.1, 127.0, 127.2, 128.5, 131.4, 131.6, 139.7, 141.4, 166.2, 178.4; FAB-HRMS calcd for C$_{22}$H$_{25}$N$_3$O$_3$ [M+H]$^+$: 380.1975; found: 380.1969. HPLC (method 2) 99.8%.

The effectiveness, or potency, of a present HDACI with respect to inhibiting the activity of an HDAC is measured by an IC$_{50}$ value. The quantitative IC$_{50}$ value indicates the concentration of a particular compound that is needed to inhibit the activity of an enzyme by 50% in vitro. Stated alternatively, the IC$_{50}$ value is the half maximal (50%) inhibitory concentration of a compound tested using a specific enzyme, e.g., HDAC, of interest. The smaller the IC$_{50}$ value, the more potent the inhibiting action of the compound because a lower concentration of the compound is needed to inhibit enzyme activity by 50%.

In preferred embodiments, a present HDACI inhibits HDAC enzymatic activity by about at least 50%, preferably at least about 75%, at least 90%, at least 95%, or at least 99%.

Compounds of the present invention were tested for IC$_{50}$ values against both HDAC6 and HDAC1. The tested compounds showed a range of IC$_{50}$ values vs. HDAC6 of about 5 nM to greater than 100 nM, and a range of IC$_{50}$ values vs. HDAC1 of about 2000 nM to about 20,000 nM. Therefore, in some embodiments, a present compound is a selective HDAC6 inhibitor which, because of a low affinity for other HDAC isozymes, e.g., HDAC1, give rise to fewer side effects than compounds that are non-selective HDAC inhibitors.

In some embodiments, the present compounds interact with and reduce the activity of all histone deacetylases in a cell. In some preferred embodiments, the present compounds interact with and reduce the activity of fewer than all histone deacetylases in the cell. In certain preferred embodiments, the present compounds interact with and reduce the activity of one histone deacetylase (e.g., HDAC-6), but do not substantially interact with or reduce the activities of other histone deacetylases (e.g., HDAC-1, HDAC-2, HDAC-3, HDAC-4, HDAC-5, HDAC-7, HDAC-8, HDAC-9, HDAC-10, and HDAC-11).

The present invention therefore provides compounds for the treatment of a variety of diseases and conditions wherein inhibition of HDAC has a beneficial effect. In preferred embodiments, a present compound inhibits HDAC and activates Nrf2 and HIF. Preferably, a present compound is selective for HDAC6 over the other HDAC isozymes by a factor of at least 2, at least 5, at least 10, at least 20, at least 50, at least 100, at least 500, at least 1000, at least 2000, at least 3000, and preferably up to about 4000. For example, in various embodiments, a present compound exhibits an $IC_{50}$ value versus HDAC6 that is about 350 or about 1000 times less than the $IC_{50}$ value vs. HDAC1, i.e., a selectivity ratio (HDAC1 $IC_{50}$/HDAC6 $IC_{50}$) of about 350 or about 1000. A present compound also shows a selectivity for HDAC6 over HDAC1, 2, 3, 4, 5, 8, 10, and 11.

The $IC_{50}$ values for compounds of structural formula (I) vs. HDAC1 and HDAC6 were determined as follows:

The HDAC1, 2, 4, 5, 6, 7, 8, 9, 10, and 11 assays used isolated recombinant human protein; HDAC3/NcoR2 complex was used for the HDAC3 assay. Substrate for HDAC1, 2, 3, 6, 10, and 11 assays is a fluorogenic peptide from p53 residues 379-382 (RHKKAc); substrate for HDAC8 is fluorogenic diacyl peptide based on residues 379-382 of p53 ($RHK_{Ac}K_{Ac}$). Acetyl-Lys(trifluoroacetyl)-AMC substrate was used for HDAC4, 5, 7, and 9 assays. Compounds were dissolved in DMSO and tested in 10-dose $IC_{50}$ mode with 3-fold serial dilution starting at 30 µM. Control Compound Trichostatin A (TSA) was tested in a 10-dose $IC_{50}$ with 3-fold serial dilution starting at 5 µM. $IC_{50}$ values were extracted by curve-fitting the dose/response slopes. Assays were performed in duplicate and $IC_{50}$ values are an average of data from both experiments.

Materials

Human HDAC1 (GenBank Accession No. NM_004964): Full length with C-terminal GST tag, MW=79.9 kDa, expressed by baculovirus expression system in Sf9 cells. Enzyme is in 50 mM Tris-HCl, pH 8.0, 138 mM NaCl, 20 mM glutathione, and 10% glycerol, and stable for >6 months at −80° C. Purity is >10% by SDS-PAGE. Specific Activity is 20 U/µg, where one U=1 pmol/min under assay condition of 25 mM Tris/Cl, pH8.0, 137 mM NaCl, 2.7 mM KCl, 1 mM $MgCl_2$, 0.1 mg/ml BSA, 100 µM HDAC substrate, and 13.2 ng/µl HDAC1, incubation for 30 min at 30° C.

Human HDAC6 (GenBank Accession No. BC069243): Full length with N-terminal GST tag, MW=159 kDa, expressed by baculovirus expression system in Sf9 cells. Enzyme is in 50 mM Tris-HCl, pH 8.0, 138 mM NaCl, 20 mM glutathione, and 10% glycerol, and stable for >6 months at −80° C. Purity is >90% by SDS-PAGE. Specific Activity is 50 U/µg, where one U=1 pmol/min under assay condition of 25 mM Tris/Cl, pH8.0, 137 mM NaCl, 2.7 mM KCl, 1 mM $MgCl_2$, and 0.1 mg/ml BSA, 30 µM HDAC substrate, and 5 ng/µl HDAC6, incubation for 60 min at 30° C.

Substrate for HDAC1 and HDAC6: Acetylated peptide substrate for HDAC, based on residues 379-382 of p53 (Arg-His-Lys-Lys(Ac)), a site of regulatory acetylation by the p300 and CBP acetyltransferases (lysines 381, 382)1-6, is the best for HDAC from among a panel of substrates patterned on p53, histone H3 and histone H4 acetylation sites7.

References: W. Gu et al., Cell (1997) 90 595; K. Sakaguchi et al., Genes Dev., (1998) 12 2831; L. Liu et al., Mol. Cell. Biol., (1999) 19 1202; A. Ito et al., EMBO J., (2001) 20 1331; N. A. Barlev et al., Mol. Cell, (2001) 8 1243; and A. Ito et al., EMBO J., (2002) 21 6236.

Reaction Buffer: 50 mM Tris-HCl, pH 8.0, 137 mM NaCl, 2.7 mM KCl, 1 mM $MgCl_2$, 1 mg/ml BSA.

Assay Conditions

HDAC1: 75 nM HDAC1 and 50 µM HDAC substrate are in the reaction buffer and 1% DMSO final. Incubate for 2 hours at 30° C.

HDAC6: 12.6 nM HDAC6 and 50 µM HDAC substrate are in the reaction buffer and 1% DMSO final. Incubate for 2 hours at 30° C.

$IC_{50}$ Calculations

All $IC_{50}$ values are automatically calculated using the GraphPad Prism version 5 and Equation of Sigmoidal dose-response (variable slope):

$$Y=\text{Bottom}+(\text{Top}-\text{Bottom})/(1+10^{((\text{Log EC50}-X)*\text{HillSlope})}),$$

where X is the logarithm of concentration, Y is the response, Y starts at Bottom and goes to Top with a sigmoid shape. In most cases, "Bottom" is set 0, and "Top" is set "less than 120%". This is identical to the "four parameter logistic equation". $IC_{50}$ curves also are drawn using the GraphPad Prism, and $IC_{50}$ values and Hill slopes are provided.

HDAC Activity Assays: HDAC assay is performed using fluorescently-labeled acetylated substrate, which comprises an acetylated lysine side chain. After incubation with HDAC, deacetylation of the substrate sensitizes the substrate such that, in a second step, treatment with the detection enzyme produces a fluorophore. HDACs 1 and 6 were expressed as full length fusion proteins. Purified proteins were incubated with 50 µM fluorescently-labeled acetylated peptide substrate and test compound for 2 hours at RT in HDAC assay buffer containing 50 mM Tris-HCl (pH 8.0), 137 mM NaCl, 2.7 mM KCl, 1 mM $MgCl_2$, 1% DMSO, and 1% BSA.

Reactions were terminated by the addition of the Developer after 2 hours, and the development of fluorescence signal, which was relative to the amount of deacetylated peptide, was monitored by time-course measurement of EnVision (PerkinElmer). The HDAC activity was estimated from the slope of time-course measurement of the fluorescence intensity. The slope of no-enzyme control (substrate alone) was served as background, and % Enzyme activity was calculated using background-subtracted slope of no inhibitor control (DMSO) as 100% activity.

To date, HDACIs have demonstrated a relatively non-specific inhibition of various HDAC isozymes. Most HDACI identified to date primarily inhibit HDAC 1, 2, 3, and 8, producing an antiproliferative phenotype which is useful for oncology applications, but not for the many non-oncology applications of HDACIs. (K. B. Glaser et al, Biochemical and biophysical research communications 2003, 310, 529-36.) The potential toxicities associated with the inhibition of certain HDAC isozymes can lead to additional difficulties for the clinical development of pan-HDAC, i.e., nonselective HDAC, inhibitors. Because the network of cellular effects mediated by acetylation is so vast and because inhibition of some HDAC isozymes may lead to undesirable side effects, selective HDAC isozyme inhibitors hold a greater therapeutic promise than their nonselective counterparts.

As illustrated below, the present compounds exhibit selective inhibition of HDAC6 compared to HDAC1.

HDAC Inhibition

All compounds have been tested against both HDAC 1 and 6 isoforms, and their $IC_{50}$ values are shown in Table 1. Selected HDAC is have been profiled against all isoforms.

TABLE 1

In vitro HDAC inhibition assay results.

| ID | Structure | HDAC isoform $IC_{50}$ (nM)[a] 1 | 6 | Ratio acetyl tub/tub fold increase[b] | Nrf2 fold activation[c] | HIF-1α fold activation[c] |
|---|---|---|---|---|---|---|
| II-ING-6 | 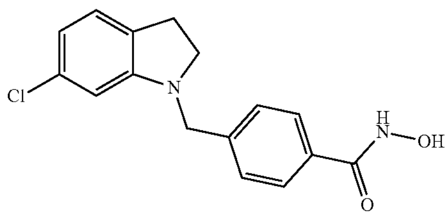 [SMILES: O=C(NO)c1ccc(CN2CCc3ccc(Cl)cc32)cc1] | 5580 | 11.5 | 15.5 (1.0 uM) | 5.6 | 7.5 |
| II-ING-39 | 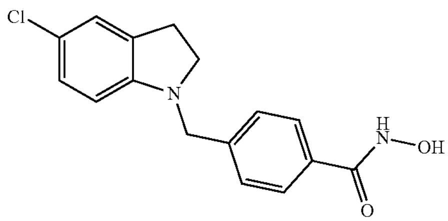 [SMILES: O=C(NO)c1ccc(CN2CCc3cc(Cl)ccc32)cc1] | 12700 | 21.5 | 1.69 (0.1 uM) | 6.5 | 7.0 |
| II-ING-41 | 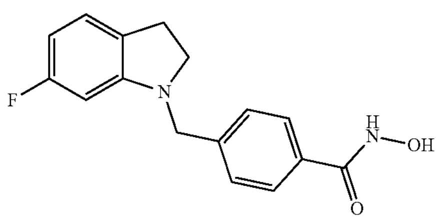 [SMILES: O=C(NO)c1ccc(CN2CCc3ccc(F)cc32)cc1] | 11780 | 16.7 | 3.47 (0.1 uM) | 7.8 | 3.6 |
| II-ING-42 | 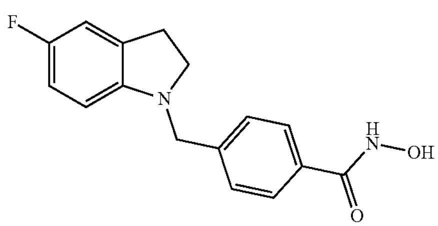 [SMILES: O=C(NO)c1ccc(CN2CCc3cc(F)ccc32)cc1] | 19980 | 13.1 | 2.46 (0.1 uM) | 7.7 | 1.4 |
| II-ING-44 | 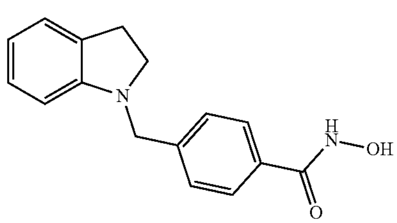 [SMILES: O=C(NO)c1ccc(CN2CCc3ccccc32)cc1] | 17600 | 26.8 | 2.68 (0.1 uM) | 2.3 | 1.4 |

TABLE 1-continued

In vitro HDAC inhibition assay results.

| ID | Structure | HDAC isoform IC$_{50}$ (nM)$^a$ 1 | 6 | Ratio acetyl tub/tub fold increase$^b$ | Nrf2 fold activation$^c$ | HIF-1α fold activation$^c$ |
|---|---|---|---|---|---|---|
| II-ING-49 | MeO-indoline-CH$_2$-C$_6$H$_4$-C(O)NHOH | 4950 | 11.5 | 2.61 (0.1 uM) | 2.4 | 1.0 |
| II-ING-51 | Cl-indoline-CH$_2$-(2-F-C$_6$H$_3$)-C(O)NHOH | 44700 | 40.2 | | 1.6 | 7.2 |
| II-ING-56 | F,Cl-indoline-CH$_2$-C$_6$H$_4$-C(O)NHOH | 7820 | 4.6 | | 5.5 | 7.8 |
| II-ING-57 | O$_2$N-indoline-CH$_2$-C$_6$H$_4$-C(O)NHOH | 1970 | 1.4 | | 6.6 | 3.9 |
| II-ING-13 | N-methylbenzimidazol-2-yl-NH-CH$_2$-C$_6$H$_4$-C(O)NHOH | 2630 | 11.0 | 2.0 (0.01 uM) | 1.8 | 2.6 |
| II-ING-61 | BnO-indoline-CH$_2$-C$_6$H$_4$-C(O)NHOH | 1850 | 25.2 | | 2.2 | 7.0 |

TABLE 1-continued

In vitro HDAC inhibition assay results.

| ID | Structure | HDAC isoform IC$_{50}$ (nM)$^a$ 1 | 6 | Ratio acetyl tub/tub fold increase$^b$ | Nrf2 fold activation$^c$ | HIF-1α fold activation$^c$ |
|---|---|---|---|---|---|---|
| II-ING-65 | 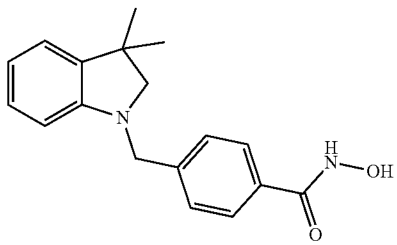 [SMILES: CC1(C)CN(Cc2ccc(C(=O)NO)cc2)c2ccccc21] | 18700 | 24.5 | | 1.8 | 2.8 |
| II-ING-66 | 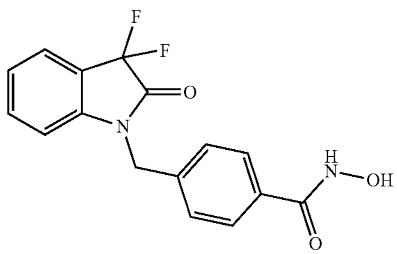 [SMILES: O=C(NO)c1ccc(CN2C(=O)C(F)(F)c3ccccc32)cc1] | 3550 | 4.1 | | 9.9 | 5.6 |
| II-ING-68 | 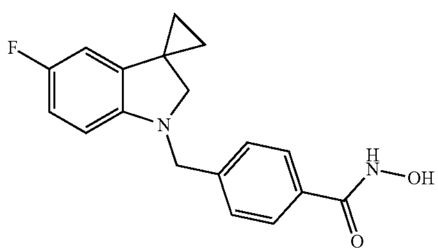 [SMILES: O=C(NO)c1ccc(CN2CC3(CC3)c3cc(F)ccc32)cc1] | 4700 | 8.2 | | 6.2 | 5.8 |
| II-ING-85 | 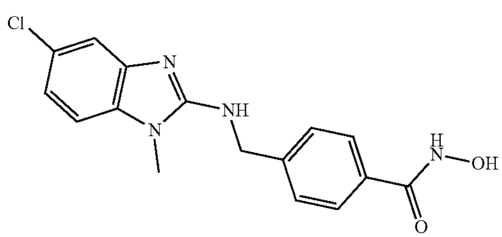 [SMILES: Cn1c(NCc2ccc(C(=O)NO)cc2)nc2cc(Cl)ccc21] | 1500 | 2.7 | | 1.3 | 1.1 |
| II-ING-87 | 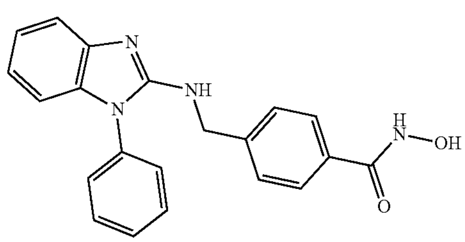 [SMILES: O=C(NO)c1ccc(CNc2nc3ccccc3n2-c2ccccc2)cc1] | 3230 | 13.0 | | 1.2 | 1.0 |
| II-ING-100 | 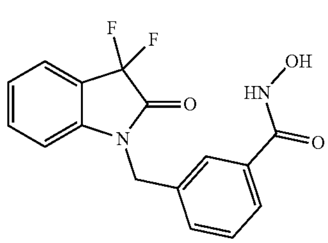 [SMILES: O=C(NO)c1cccc(CN2C(=O)C(F)(F)c3ccccc32)c1] | 30000 | 5560 | | 1.5 | 1.0 |

TABLE 1-continued

In vitro HDAC inhibition assay results.

| ID | Structure | HDAC isoform IC$_{50}$ (nM)[a] 1 | HDAC isoform IC$_{50}$ (nM)[a] 6 | Ratio acetyl tub/tub fold increase[b] | Nrf2 fold activation[c] | HIF-1α fold activation[c] |
|---|---|---|---|---|---|---|
| II-ING-101 | | 7880 | 5.1 | | 3.4 | 1.0 |
| II-ING-109 | | 19700 | 18.0 | | 1.5 | 1.0 |
| II-ING-118 | | 7880 | 5.8 | | 2.0 | 1.3 |

[a] Performed by Reaction Biology Corporation (http://www.reactionbiology.com)
[b] Normalized to the values of DMSO
[c] Measured at 10 μM.

TABLE 2

In vitro isoform selectivity assay with selected HDACis

| Compound | HDAC Inhibition (IC$_{50}$ uM) isoforms | | | | | | | | | | |
|---|---|---|---|---|---|---|---|---|---|---|---|
| | 1 | 2 | 3 | 4 | 5 | 6 | 7 | 8 | 9 | 10 | 11 |
| II-ING-6 | 3.77 | 6.24 | 4.34 | 3.48 | 2.70 | 0.009 | 0.98 | 0.53 | 2.06 | 6.39 | 4.52 |
| II-ING-13 | 2.55 | 5.20 | 3.51 | 2.42 | 1.96 | 0.009 | 0.55 | 0.17 | 1.10 | 5.95 | 2.11 |
| II-ING-41 | 3.67 | 7.15 | 5.43 | 2.41 | 1.39 | 0.004 | 0.46 | 0.19 | 1.00 | 6.03 | 5.37 |

[a] Performed by Reaction Biology Corporation (http://www.reactionbiology.com)

Tubulin Acetylation

N2a cells were treated ON with 100 nM of the various test compounds and compared to DMSO-treated cells. Cells were collected using RIPA buffer. WB was analyzed using Image QuantTL and the ratio between the intensity of the acetylated tubulin and the tubulin bands was calculated. These ratios were subsequently normalized to the values of DMSO (fold increase). For each sample 50 μg protein was loaded on a 12% SDS-PAGE gel and blotted on a PVDF membrane. The integrated density of acetylated α-tubulin and α-tubulin was measured on WB using Image J software. Furthermore the ratio between the integrated density of acetylated α-tubulin and α-tubulin was calculated. Table 1 summarizes the results of the tubulin acetylation tests.

The present compounds were evaluated for an ability to activate Nrf2 and HIF-1α. Table 1 summarizes Nrf2 activation data obtained in Neh2-luc reporter assay; and HIF1 activation measured in ODD reporter assay.

Neuroprotection

Compound II-ING-66 was examined in a model of oxidative stress induced by homocysteic acid (HCA), where neurons were treated with the test compound alone or in the presence of HCA. Cell viability was assessed using the MTT assay, and the results are summarized in FIG. 1.

Figure 2A:
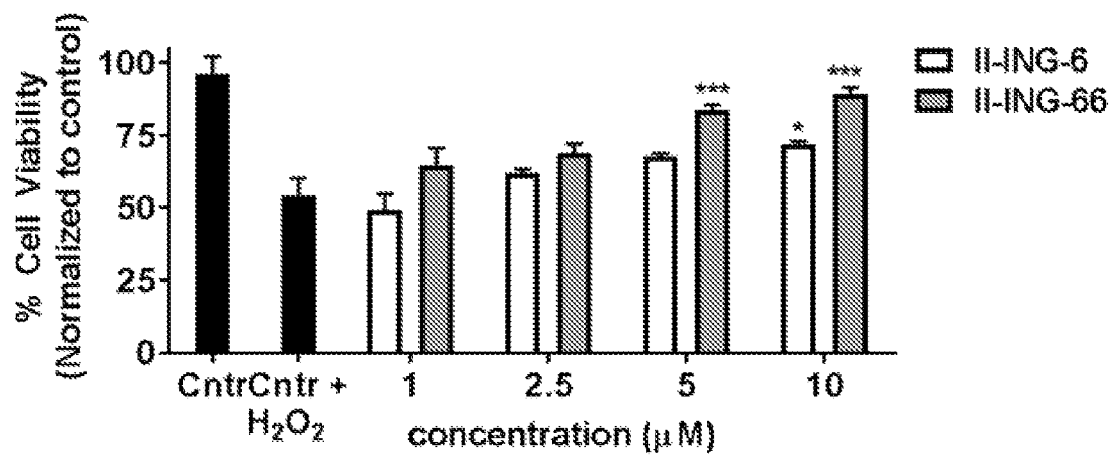
FIG. 2A contains bar graphs showing the concentration-dependent neuroprotection of SH-SY5Y cells from $H_2O_2$-induced toxicity. Cell viability was measured using the MTT assay at 24 h. Data show mean and SEM normalized to control (n=6): *$p<0.05$, ***$p<0.001$ versus control insult (n=6/group), by 1-way ANOVA Dunnett's test. (B) Test compounds at 5 µM protected N2a cells against MPP+ (100 µM) insult. Cell viability was measured at 24 h using Presto-Blue assay. Data show mean and SEM (n=3): *$p<0.05$ versus control insult.
Figure 2B:
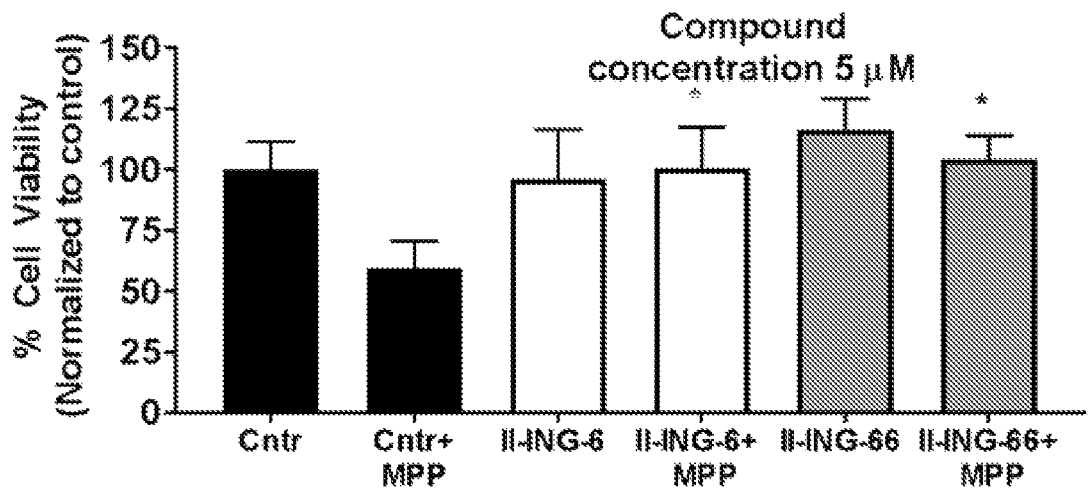
FIG. 2B contains bar graphs showing test compounds at 5 µM protected N2a cells against MPP+(100 µM) insult. Cell viability was measured at 24 h using Presto-Blue assay. Data show mean and SEM (n=3): *$p<0.05$ versus control insult.
Figure 3A:
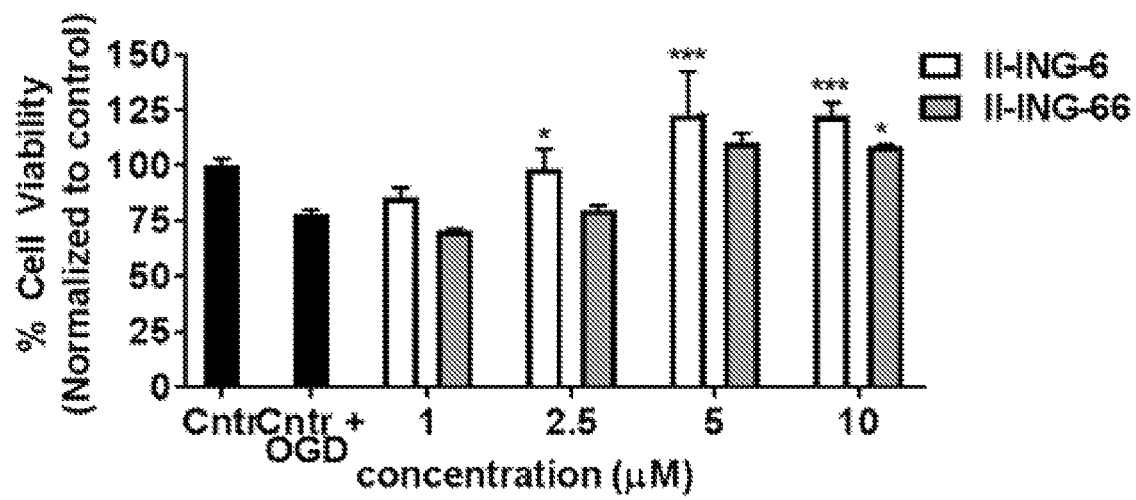
FIG. 3A contains bar graphs showing a concentration dependence of II-ING-6 and II-ING-66 neuroprotection in SH-SY5Y cells subject to OGD: 24 h pretreatment.
Figure 3B:
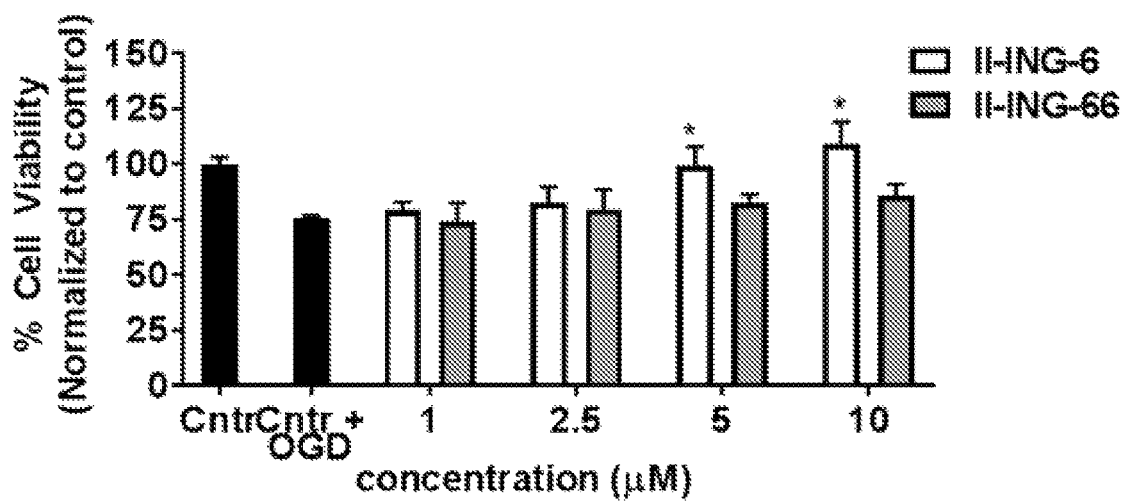
FIG. 3B contains bar graphs showing concentration dependencies of II-ING-6 and II-ING-66 neuroprotection in SH-SY5Y cells subject to OGD: treatment post OGD. Cell viability was measured using the MTT assay 24 h post insult. Data show mean and SEM normalized to control (n=6): *$p<0.05$, ***$p<0.001$ versus insult by 1-way ANOVA with Dunnett's test.

II-ING-6 and II-ING-66, were tested in neuronal cell lines subjected to $H_2O_2$ and MPP+-induced toxicity (Parkinson's disease model), and in a composite model of ischemia-reperfusion injury: oxygen glucose deprivation (OGD). In $H_2O_2$-induced neurotoxicity in human neuronal SH-SY5Y cells, neuroprotective properties of compounds II-ING-6 and II-ING-66 were assessed using 24 h pretreatment regimen (FIG. 2A). Significant neuroprotection was observed with both compounds. Both II-ING-6 and II-ING-66 at 5 µM produced significant protection against MPP+ neurotoxicity in mouse neuronal N2a cells (FIG. 2B). Neuroprotection against OGD is expected to be mediated by HIF-1α and Nrf2. In this assay, after pretreatment of cells 24 h prior to OGD insult, both compounds were neuroprotective (FIG. 3A). Post-treatment of cells after OGD yielded significant neuroprotection only for compound II-ING-6 (FIG. 3B).

Both activation of Nrf2 and inhibition of PHD (via HIF-1α and other mechanisms) have been reported to provide neuroprotection. In a selective HDAC6 inhibitor, these additional mechanisms would be expected to yield a multifunctional neuroprotective agent. Novel phenyl-hydroxamates with specific cap groups selectively inhibit HDAC6 and stabilize two master regulators of cellular stress response.

Compounds II-ING-6 and II-ING-66 showed no toxicity at ≤200 µM, with $LC_{50}$>500 µM in the "liver-on-a-chip" assay, testing viability of HepaRG "hepatocytes" after 48 h by MTT, indicating a wide therapeutic index.

In Vitro Metabolic stability in human liver microsomes data are summarized in Table 3.

TABLE 3

| Compound | Microsomes stability* (% remaining vs$T_0$) |
| --- | --- |
| II-ING-6 | 88.6 |
| II-ING-39 | 81.7 |
| II-ING-41 | 88.1 |

*measured in human liver microsomes after 60 min at 10 uM

Blood Brain Barrier

Tests were conducted to determine the ability of a present compound to cross the blood brain barrier (BBB). In particular, Mouse 1 was injected iv with about 7.5 mg/kg of compound II-ING-6 in DMSO. Mouse 2—about 10 mg/kg. Blood, brain, and liver were collected after 20 minutes (Table 4).

TABLE 4

| Sample # | Dose mg/kg | Tissue | Concentration ng/g |
| --- | --- | --- | --- |
| 1 | 7.5 | Plasma | 256 |
|   |   | Brain | 1064 |
|   |   | Liver | 501 |

TABLE 4-continued

| Sample # | Dose mg/kg | Tissue | Concentration ng/g |
| --- | --- | --- | --- |
| 2 | 10 | Plasma | 387 |
|   |   | Brain | 1758 |
|   |   | Liver | 1034 |

Behavioral Screening in the SmartCube (SC)® Platform

Figure 4:
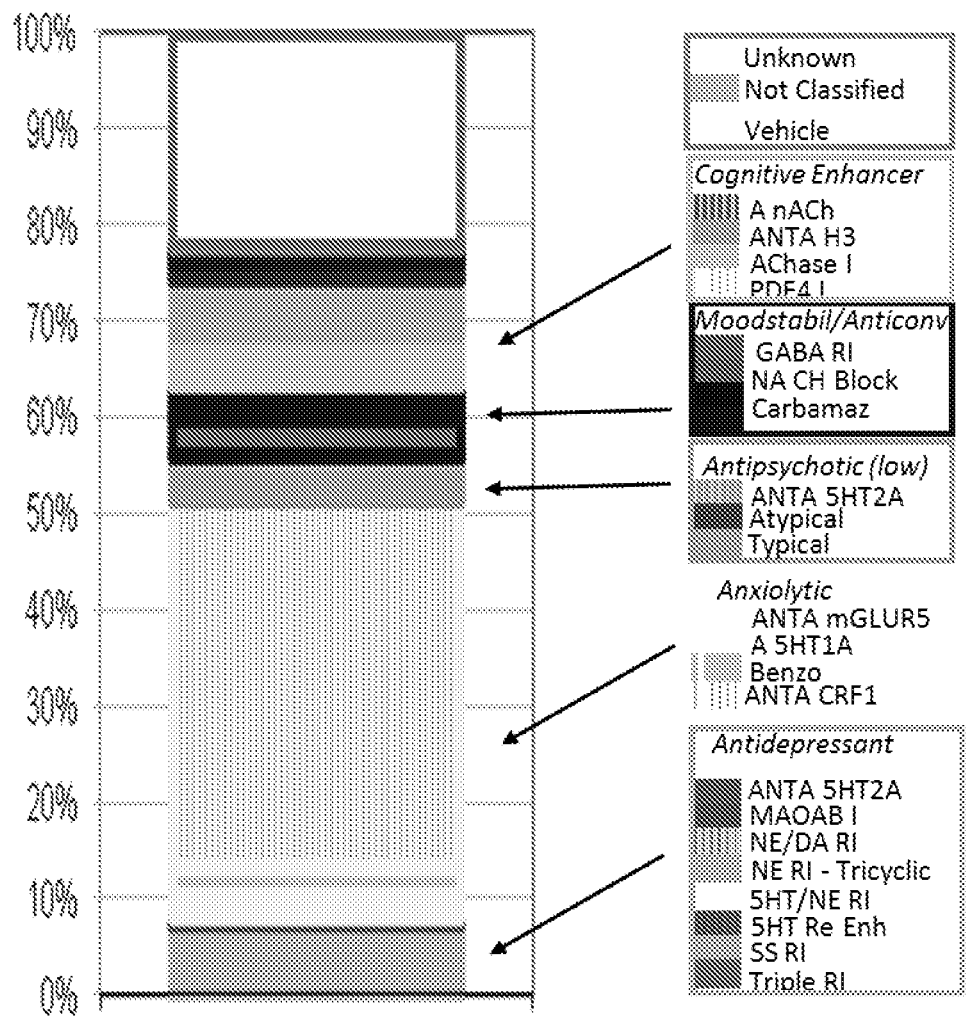
FIG. 4 contains the SC signature of II-ING-6 (50 mg/kg, ip) showing anxiolytic activity.

Another evidence that II-ING-6 is can cross the BBB was obtained from SC (Frontiers in Neuroscience 2011, 5 (103), p. 1-4) experiment. SC provides a sequence of challenges to mice and captures more than 2,000 features during a 1 hour testing session. These features are analyzed with computer algorithms and data mining approaches to automate the study of mice behavior and compared to a database of behavioral signatures obtained using a set of diverse reference compounds, including antidepressants, cognitive enhancers, antipsychotics, and anxiolytics. In this assay, C57BL/6 mice were injected with compound II-ING-6 at 50 mg/kg (ip). A robust SC signature was obtained, indicating that this compound has anxiolytic effect. The results are summarized in FIG. 4.

Genetic Toxicity

Compound II-ING-6 was tested in genetic toxicity assays to assess the mutagenic potential of the compound. The Ames test was done with several strains of bacterium, such as: TA98-S9, TA100-S9, TA1535-59, and TA1537-59. In each experiment and if applicable, the respective reference compounds were tested concurrently with II-ING-6, and the data were compared with historical values determined at Eurofin Inc. Negative test results with this compound tested at concentrations of 0.6-100 µM prove that compound II-ING-6 is not mutagenic.

Selectivity:

Compound II-ING-6 also was tested in a panel of 43 cloned human and rodent CNS receptors, channels and transporters using the NIMH sponsored Psychoactive Drug Screening Program (PDSP). No significant activity was found in these assays.

In Vivo Activation of Nrf2 Pathway

The expression of Nrf2 target genes was assessed in 3 month old male C57BL/6 mice administered with II-ING-66 (25 mg/kg i.p.). Analysis by RT-PCR showed significant increases in Hmox-1 and NQO1 in the ventral midbrain and striatum. Hmox-1 expression was also significantly upregulated in the liver. These in vivo data support the in vitro observations of HIF-1α and Nrf2 activation by phenylhydroxamate HDAC inhibitors (Gaisina et al, ACS Chem. Neurosci. 2017).

In one embodiment, the present invention relates to a method of treating an individual suffering from a disease or condition wherein inhibition of HDACs and/or activation of Nrf2 and HIF provide a benefit comprising administering a therapeutically effective amount of a present compound to an individual in need thereof. In preferred embodiments, a present compound inhibits HDACs and activates Nrf2 and HIF.

The methods described herein relate to the use of a present compounds and an optional second therapeutic agent useful in the treatment of diseases and conditions wherein inhibition of HDAC provides a benefit and/or activation of Nrf2 and HIF. The methods of the present invention can be accomplished by administering a present compounds as the neat compound or as a pharmaceutical composition. Administration of a pharmaceutical composition, or a neat compound of the present invention, can be performed during or after the onset of the disease or condition of interest. Typically, the pharmaceutical compositions are sterile, and contain no toxic, carcinogenic, or mutagenic compounds that would cause an adverse reaction when administered.

In many embodiments, a present compound is administered in conjunction with a second therapeutic agent useful in the treatment of a disease or condition wherein inhibition of HDAC and/or activation of Nrf2 and HIF provides a benefit. The second therapeutic agent is different from a present compound. A present compound and the second therapeutic agent can be administered simultaneously or sequentially. In addition, a present compound and second therapeutic agent can be administered from a single composition or two separate compositions. A present compound and the second therapeutic agent can be administered simultaneously or sequentially to achieve the desired effect.

The second therapeutic agent is administered in an amount to provide its desired therapeutic effect. The effective dosage range for each second therapeutic agent is known in the art, and the second therapeutic agent is administered to an individual in need thereof within such established ranges.

The present invention therefore is directed to compositions and methods of treating diseases or conditions wherein inhibition of HDAC and/or activation of Nrf2 and HIF provides a benefit. The present invention also is directed to pharmaceutical compositions comprising a present compound and an optional second therapeutic agent useful in the treatment of diseases and conditions wherein inhibition of HDAC and/or activation of Nrf2 and HIF provides a benefit. Further provided are kits comprising a present compound and, optionally, a second therapeutic agent useful in the treatment of diseases and conditions wherein inhibition of HDAC and/or activation of Nrf2 and HIF provides a benefit, packaged separately or together, and an insert having instructions for using these active agents.

A present compound and the second therapeutic agent can be administered together as a single-unit dose or separately as multi-unit doses, wherein the present compound is administered before the second therapeutic agent or vice versa. One or more dose of a present compound and/or one or more dose of the second therapeutic agent can be administered. The present compound therefore can be used in conjunction with one or more second therapeutic agents, for example, but not limited to, anticancer agents.

Within the meaning of the present invention, the term "disease" or "condition" denotes disturbances and/or anomalies that as a rule are regarded as being pathological conditions or functions, and that can manifest themselves in the form of particular signs, symptoms, and/or malfunctions. As demonstrated below, a present compound is a potent inhibitor of HDAC and/or activation of Nrf2 and HIF and can be used in treating diseases and conditions wherein inhibition of HDAC and/or activation of Nrf2 and HIF provides a benefit, for example, cancer, a neurological disease, a neurodegenerative condition, traumatic brain injury, stroke, an inflammation, an autoimmune disease, autism, and malaria.

In one preferred embodiment, the present invention provides methods for treating cancer, including but not limited to killing a cancer cell or neoplastic cell; inhibiting the growth of a cancer cell or neoplastic cell; inhibiting the replication of a cancer cell or neoplastic cell; or ameliorating a symptom thereof, said methods comprising administering to a subject in need thereof a therapeutically effective amount of a present compound.

In one embodiment, the invention provides a method for treating cancer comprising administering to a subject in need thereof an amount of a present compound or a pharmaceutically acceptable salt thereof sufficient to treat the cancer. A present compound can be used as the sole anticancer agent, or in combination with another anticancer treatment, e.g., radiation, chemotherapy, and surgery.

In another embodiment, the invention provides a method for increasing the sensitivity of a cancer cell to the cytotoxic effects of radiotherapy and/or chemotherapy comprising contacting the cell with a present compound or a pharmaceutically acceptable salt thereof in an amount sufficient to increase the sensitivity of the cell to the cytotoxic effects of radiotherapy and/or chemotherapy.

In a further embodiment, the present invention provides a method for treating cancer comprising: (a) administering to an individual in need thereof an amount of a present compound; and (b) administering to the individual an amount of radiotherapy, chemotherapy, or both. The amounts administered are each effective to treat cancer. In another embodiment, the amounts are together effective to treat cancer.

In another embodiment, the invention provides a method for treating cancer, said method comprising administering to a subject in need thereof a pharmaceutical composition comprising an amount of a present compound effective to treat cancer.

This combination therapy of the invention can be used accordingly in a variety of settings for the treatment of various cancers. In a specific embodiment, the individual in need of treatment has previously undergone treatment for cancer. Such previous treatments include, but are not limited to, prior chemotherapy, radiotherapy, surgery, or immunotherapy, such as cancer vaccines.

In another embodiment, the cancer being treated is a cancer which has demonstrated sensitivity to radiotherapy and/or chemotherapy or is known to be responsive to radiotherapy and/or chemotherapy. Such cancers include, but are not limited to, non-Hodgkin's lymphoma, Hodgkin's disease, Ewing's sarcoma, testicular cancer, prostate cancer, ovarian cancer, bladder cancer, larynx cancer, cervical cancer, nasopharynx cancer, breast cancer, colon cancer, pancreatic cancer, head and neck cancer, esophageal cancer, rectal cancer, small-cell lung cancer, non-small cell lung cancer, brain tumors, or other CNS neoplasms.

In still another embodiment, the cancer being treated has demonstrated resistance to radiotherapy and/or chemotherapy or is known to be refractory to radiotherapy and/or chemotherapy. A cancer is refractory to a therapy when at least some significant portion of the cancer cells are not killed or their cell division is not arrested in response to therapy. Such a determination can be made either in vivo or in vitro by any method known in the art for assaying the effectiveness of treatment on cancer cells, using the art-accepted meanings of "refractory" in such a context. In a specific embodiment, a cancer is refractory where the number of cancer cells has not been significantly reduced or has increased.

Other cancers that can be treated with the compounds and methods of the invention include, but are not limited to, cancers and metastases selected from the group consisting of solid tumors, including but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiornyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforma, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; blood-borne cancers, including but not limited to: acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myclomonocytic leukemia, acute nonlymphocytic leukemia, acute undifferentiated leukemia, chronic myclocytic leukemia, chronic lymphocytic leukemia, hairy cell leukemia, and multiple myeloma; acute and chronic leukemias: lymphoblastic, myelogenous lymphocytic, and myelocytic leukemias; lymphomas: Hodgkin's disease and non-Hodgkin's lymphoma; multiple myeloma; Waldenstrom's macroglobulinemia; heavy chain disease; and polycythemia vera.

The present compounds can also be administered to prevent progression to a neoplastic or malignant state, including but not limited to the cancers listed above. Such prophylactic use is indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, *Basic Pathology*, 2d Ed., W.B. Saunders Co., Philadelphia, pp. 68-79). Hyperplasia is a form of controlled cell proliferation involving an increase in cell number in a tissue or organ, without significant alteration in structure or function. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where chronic irritation or inflammation exists, and often is found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype, or of a malignant phenotype, displayed in vivo or displayed in vitro by a cell sample from a subject, can indicate the desirability of prophylactic/therapeutic administration of the composition of the invention. Such characteristics of a transformed phenotype include, for example, morphology changes, looser substratum attachment, loss of contact inhibition, loss of anchorage dependence, protease release, increased sugar transport, decreased serum requirement, expression of fetal antigens, disappearance of the 250,000 dalton cell surface protein.

In a specific embodiment, leukoplakia, a benign-appearing hyperplastic or dysplastic lesion of the epithelium, or Bowen's disease, a carcinoma in situ, are pre-neoplastic lesions indicative of the desirability of prophylactic intervention.

In another embodiment, fibrocystic disease (cystic hyperplasia, mammary dysplasia, particularly adenosis (benign epithelial hyperplasia)) is indicative of the desirability of prophylactic intervention.

The prophylactic use of the compounds and methods of the present invention are also indicated in some viral infections that may lead to cancer. For example, human papilloma virus can lead to cervical cancer (see, e.g., Hernandez-Avila et al., *Archives of Medical Research* (1997) 28:265-271), Epstein-Barr virus (EBV) can lead to lymphoma (see, e.g., Herrmann et al., *J Pathol* (2003) 199(2):140-5), hepatitis B or C virus can lead to liver carcinoma (see, e.g., El-Serag, *J Clin Gastroenterol* (2002) 35(5 Suppl 2):S72-8), human T cell leukemia virus (HTLV)-I can lead to T-cell leukemia (see e.g., Mortreux et al., *Leukemia* (2003) 17(1):26-38), human herpesvirus-8 infection can lead to Kaposi's sarcoma (see, e.g., Kadow et al., *Curr Opin Investig Drugs* (2002) 3(11):1574-9), and Human Immune deficiency Virus (HIV) infection contribute to cancer development as a consequence of immunodeficiency (see, e.g., Dal Maso et al., *Lancet Oncol* (2003) 4(2):110-9).

In other embodiments, a subject exhibiting one or more of the following predisposing factors for malignancy can be treated by administration of the present compounds and methods of the invention: a chromosomal translocation associated with a malignancy (e.g., the Philadelphia chromosome for chronic myelogenous leukemia, t(14;18) for follicular lymphoma, etc.), familial polyposis or Gardner's syndrome (possible forerunners of colon cancer), benign monoclonal gammopathy (a possible forerunner of multiple myeloma), a first degree kinship with persons having a cancer or procancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia, and Bloom's syndrome; see Robbins and Angell, 1976, *Basic Pathology*, 2d Ed., W.B. Saunders Co., Philadelphia, pp. 112-113) etc.), and exposure to carcinogens (e.g., smoking, and inhalation of or contacting with certain chemicals).

In another specific embodiment, the present compounds and methods of the invention are administered to a human subject to prevent progression of breast, colon, ovarian, or cervical cancer.

In one embodiment, the invention provides methods for treating cancer comprising (a) administering to an individual in need thereof an amount of a present compound; and (b) administering to the individual one or more additional anticancer treatment modality including, but not limited to, radiotherapy, chemotherapy, surgery or immunotherapy, such as a cancer vaccine. In one embodiment, the administering of step (a) is prior to the administering of step (b). In another embodiment, the administering of step (a) is subsequent to the administering of step (b). In still another embodiment, the administering of step (a) is concurrent with the administering of step (b).

In one embodiment, the additional anticancer treatment modality is radiotherapy and/or chemotherapy. In another embodiment, the additional anticancer treatment modality is surgery.

In still another embodiment, the additional anticancer treatment modality is immunotherapy, such as cancer vaccines.

In one embodiment, a present compound or a pharmaceutically acceptable salt thereof is administered adjunctively with the additional anticancer treatment modality.

In a preferred embodiment, the additional anticancer treatment modality is radiotherapy. In the methods of the present invention, any radiotherapy protocol can be used depending upon the type of cancer to be treated. Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

For example, but not by way of limitation, X-ray radiation can be administered; in particular, high-energy megavoltage (radiation of greater that 1 MeV energy) can be used for deep tumors, and electron beam and orthovoltage X-ray radiation can be used for skin cancers. Gamma-ray emitting radioisotopes, such as radioactive isotopes of radium, cobalt and other elements, can also be administered. Illustrative radiotherapy protocols useful in the present invention include, but are not limited to, stereotactic methods where multiple sources of low dose radiation are simultaneously focused into a tissue volume from multiple angles; "internal radiotherapy," such as brachytherapy, interstitial irradiation, and intracavitary irradiation, which involves the placement of radioactive implants directly in a tumor or other target tissue; intraoperative irradiation, in which a large dose of external radiation is directed at the target tissue which is exposed during surgery; and particle beam radiotherapy, which involves the use of fast-moving subatomic particles to treat localized cancers.

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present compound, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

In a preferred embodiment, a present compound or a pharmaceutically acceptable salt thereof is administered prior to the administration of radiotherapy and/or chemotherapy.

In another preferred embodiment, a present compound or a pharmaceutically acceptable salt thereof is administered adjunctively with radiotherapy and/or chemotherapy.

A present compound and additional treatment modalities can act additively or synergistically (i.e., the combination of a present compound or a pharmaceutically acceptable salt thereof, and an additional anticancer treatment modality is more effective than their additive effects when each are administered alone). A synergistic combination permits the use of lower dosages of a present compound and/or the additional treatment modality and/or less frequent administration of a present compound and/or additional treatment modality to a subject with cancer. The ability to utilize lower dosages of a present compound and/or an additional treatment modality and/or to administer a compound of the invention and the additional treatment modality less frequently can reduce the toxicity associated with the administration without reducing the efficacy of a present compound and/or the additional treatment modality in the treatment of cancer. In addition, a synergistic effect can result in the improved efficacy of the treatment of cancer and/or the reduction of adverse or unwanted side effects associated with the administration of a present compound and/or an additional anticancer treatment modality as monotherapy.

In one embodiment, the present compounds may act synergistically with radiotherapy when administered in doses typically employed when such compounds are used alone for the treatment of cancer. In another embodiment, the present compounds may act synergistically with radiotherapy when administered in doses that are less than doses typically employed when such compounds are used as monotherapy for the treatment of cancer.

In one embodiment, radiotherapy may act synergistically with a present compound when administered in doses typically employed when radiotherapy is used as monotherapy for the treatment of cancer. In another embodiment, radiotherapy may act synergistically with a compound of the invention when administered in doses that are less than doses typically employed when radiotherapy is used as monotherapy for the treatment of cancer.

The effectiveness of the present compounds as HDAC inhibitors for sensitizing cancer cells to the effect of radiotherapy can be determined by the in vitro and/or in vivo determination of post-treatment survival using techniques known in the art. In one embodiment, for in vitro determinations, exponentially growing cells can be exposed to known doses of radiation, and the survival of the cells monitored. Irradiated cells are plated and cultured for about 14-about 21 days, and the colonies are stained. The surviving fraction is the number of colonies divided by the plating efficiency of unirradiated cells. Graphing the surviving fraction on a log scale versus the absorbed dose on a linear scale generates a survival curve. Survival curves generally show an exponential decrease in the fraction of surviving cells at higher radiation doses after an initial shoulder region in which the dose is sublethal. A similar protocol can be used for chemical agents when used in the combination therapies of the invention.

Inherent radiosensitivity of tumor cells and environmental influences, such as hypoxia and host immunity, can be further assessed by in vivo studies. The growth delay assay is commonly used. This assay measures the time interval required for a tumor exposed to radiation to regrow to a specified volume. The dose required to control about 50% of tumors is determined by the $TCD_{50}$ assay.

In vivo assay systems typically use transplantable solid tumor systems in experimental subjects. Radiation survival parameters for normal tissues as well as for tumors can be assayed using in vivo methods known in the art.

The present invention provides methods of treating cancers comprising the administration of an effective amount of a present compound in conjunction with recognized methods of surgery, radiotherapy, and chemotherapies, including, for example, chemical-based mimics of radiotherapy whereby a synergistic enhancement of the effectiveness of the recognized therapy is achieved. The effectiveness of a treatment can be measured in clinical studies or in model systems, such as a tumor model in mice, or cell culture sensitivity assays.

The present invention provides combination therapies that result in improved effectiveness and/or reduced toxicity. Accordingly, in one aspect, the invention relates to the use of the present compounds as radiosensitizers in conjunction with radiotherapy.

When the combination therapy of the invention comprises administering a present HDACI with one or more additional anticancer agents, a present compound and the additional anticancer agents can be administered concurrently or sequentially to an individual. The agents can also be cyclically administered. Cycling therapy involves the administration of one or more anticancer agents for a period of time, followed by the administration of one or more different anticancer agents for a period of time and repeating this sequential administration, i.e., the cycle, in order to reduce the development of resistance to one or more of the anticancer agents of being administered, to avoid or reduce the side effects of one or more of the anticancer agents being administered, and/or to improve the efficacy of the treatment.

An additional anticancer agent may be administered over a series of sessions; anyone or a combination of the additional anticancer agents listed below may be administered.

The present invention includes methods for treating cancer comprising administering to an individual in need thereof a present compound and one or more additional anticancer agents or pharmaceutically acceptable salts thereof. A present compound and the additional anticancer agent can act additively or synergistically. Suitable anticancer agents include, but are not limited to, gemcitabine, capecitabine, methotrexate, taxol, taxotere, mereaptopurine, thioguanine, hydroxyurea, cyclophosphamide, ifosfamide, nitrosoureas, mitomycin, dacarbazine, procarbizine, etoposide, teniposide, campatheeins, bleomycin, doxorubicin, idarubicin, daunorubicin, dactinomycin, plicamycin, mitoxantrone, L-asparaginase, doxorubicin, epirubicin, 5-fluorouracil (5-FU), taxanes (such as docetaxel and paclitaxel), leucovorin, levamisole, irinotecan, estramustine, etoposide, nitrogen mustards, BCNU, nitrosoureas (such as carmustine and lomustine), platinum complexes (such as cisplatin, carboplatin and oxaliplatin), imatinib mesylate, hexamethylmelamine, topotecan, tyrosine kinase inhibitors, tyrphostins herbimycin A, genistein, erbstatin, and lavendustin A.

In one embodiment, the anti-cancer agent can be, but is not limited to, a drug selected from the group consisting of alkylating agents, nitrogen mustards, cyclophosphamide, trofosfamide, chlorambucil, nitrosoureas, carmustine (BCNU), lomustine (CCNU), alkylsulphonates, busulfan, treosulfan, triazenes, plant alkaloids, vinca alkaloids (vineristine, vinblastine, vindesine, vinorelbine), taxoids, DNA topoisomcrase inhibitors, epipodophyllins, 9-aminocamptothecin, camptothecin, crisnatol, mitomycins, mitomycin C, anti-metabolites, anti-folates, DHFR inhibitors, trimetrexate, IMP dehydrogenase inhibitors, mycophenolic acid, tiazofurin, ribavirin, EICAR, ribonucleotide reductase inhibitors, hydroxyurea, deferoxamine, pyrimidine analogs, uracil analogs, floxuridine, doxifluridine, ratitrexed, cytosine analogs, cytarabine (ara C), cytosine arabinoside, fludarabine, purine analogs, mercaptopurine, thioguanine, DNA antimetabolites, 3-HP, 2'-deoxy-5-fluorouridine, 5-HP, alpha-TGDR, aphidicolin glycinate, ara-C, 5-aza-2'-deoxycytidine, beta-TGDR, cyclocytidine, guanazole (inosine glycodialdehyde), macebecin II, pyrazoloimidazole, hormonal therapies, receptor antagonists, anti-estrogen, tamoxifen, raloxifene, megestrol, LHRH agonists, goserelin, leuprolide acetate, anti-androgens, flutamide, bicalutamide, retinoids/deltoids, cis-retinoic acid, vitamin A derivative, all-trans retinoic acid (ATRA-IV), vitamin D3 analogs, E1) 1089, CB 1093, ICH 1060, photodynamic therapies, vertoporfin, BPD-MA, phthalocyanine, photosensitizer Pc4, demethoxy-hypocrellin A (2BA-2-DMHA), cytokines, interferon-a, interferon-I3, interferon-y, tumor necrosis factor, angiogenesis inhibitors, angiostatin (plasminogen fragment), antiangiogenic antithrombin UI, angiozyme, ABT-627, Bay 12-9566, benefin, bevacizumab, BMS-275291, cartilage-derived inhibitor (CDI), CAI, CD59 complement fragment, CEP-7055, Col 3, combretastatin A-4, endostatin (collagen XVIII fragment), fibronectin fragment, Gro-beta, halofuginone, heparinases, heparin hexasaccharide fragment, HMV833, human chorionic gonadotropin (hCG), IM-862, interferon inducible protein (IP-10), interleukin-12, kringle 5 (plasminogen fragment), marimastat, metalloproteinase inhibitors (UMPs), 2-methoxyestradiol, MMI 270 (CGS 27023A), MoAb IMC-I C11, neovastat, NM-3, panzem, P1-88, placental ribonuclease inhibitor, plasminogen activator inhibitor, platelet factor-4 (PF4), prinomastat, prolactin 161(D fragment, proliferin-related protein (PRP), PTK 787/ZK 222594, retinoids, solimastat, squalamine, SS 3304, SU 5416, SU 6668, SU 11248, tetrahydrocortisol-S, tetrathiomolybdate, thalidomide, thrombospondin-1 (TSP-1), TNP-470, transforming growth factor-beta (TGF-11), vasculostatin, vasostatin (calreticulin fragment), ZD 6126, ZD 6474, famesyl transferase inhibitors (FTI), bisphosphonates, antimitotic agents, allocolchicine, halichondrin B, colchicine, colchicine derivative, dolstatin 10, maytansine, rhizoxin, thiocolchicine, trityl cysteine, isoprenylation inhibitors, dopaminergic neurotoxins, 1-methyl-4-phenylpyridinium ion, cell cycle inhibitors, staurosporine, actinomycins, actinomycin D, dactinomycin, bleomycins, bleomycin A2, bleomycin B2, peplomycin, anthracycline, adriamycin, epirubicin, pirarnbicin, zorubicin, mitoxantrone, MDR inhibitors, verapamil, $Ca^{2+}$ATPase inhibitors, and thapsigargin.

Other anti-cancer agents that may be used in the present invention include, but are not limited to, acivicin; aclarubicin; acodazole hydrochloride; acronine; adozelesin;

aldesleukin; altretamine; arnbomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelcsin; bleomycin sulfate; brequinar sodium; bropirimine; busul fan; cactinomycin; calusterone; caracemide; carbetimer; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexorrnaplatin; dezaguanine; dezaguanine mesylate; diaziquone; docetaxel; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-Ia; interferon gamma-Ib; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mecchlorethamine hydrochloride; megestrol acetate; melengestrol acetate; melphalan; menogaril; mercaptopurine; methotrexate sodium; metoprine; meturedepa; mitindomide; mitocarcin; mitocromin; mitogillin; mitomalcin; mitomycin; mitusper; mitotane; mitoxantrone hydrochloride; mycophenolic acid; nocodazole; nogalamycin; ormaplatin; oxisuran; pegaspargase; peliomycin; pentamustine; peplomycin sulfate; perfosfarnide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsornycin; spirogermanium hydrochloride; spiromustine; spiroplatin; streptonigrin; streptozocin; sulofenur; talisomycin; tecogalan sodium; tegafur; teloxantrone hydrochloride; temoporfin; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracit mustard; uredepa; vapreotide; verteporfln; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozolc; zeniplatin; zinostatin; zorubicin hydrochloride.

Further anti-cancer drugs that can be used in the present invention include, but are not limited to: 17-AAG; 20-epi-1,25-dihydroxyvitamin D3; 5-ethynyluracil; abiraterone; aclarubicin; acylfulvene; adecypenol; adozelesin; aldesleukin; ALL TK antagonists; altretamine; ambamustine; amidox; arnifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein 1; antiandrogen, prostatic carcinoma; antiestrogen; antineoplaston; antisense oligonucleotides; aphidicolin glycinate; apoptosis gene modulators; apoptosis regulators; apurinic acid; ara CDP DL PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR-ABL antagonists; benzochlorins; benzoylstaurosporine; beta lactam derivatives; beta alethine; beta-clarnycin B; betulinic acid; bFGF inhibitor; bicalutamide; bisantrene; bisaziridinylsperrnine; bisnafide; bistratene A; bizelesin; bortezomib; breflate; bropirimine; budotitane; buthionine sulfoximine; calcipotriol; calphostin C; camptothecin derivatives; canarypox IL-2; carboxamide amino triazole; carboxyarnidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexveraparnil; diaziquone; didemnin B; didox; diethylnorspermine; dihydro 5 azacytidine; dihydrotaxol, 9; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fltidarabine; fluorodaunoruniein hydrochloride; forfenimex; formestane; fostriecin; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin like growth factor 1 receptor inhibitor; interferon agonists; interferons; interleukins; iobenguane; iododoxorubiein; ipomeanol, 4; iroplact; irsogladine; isobengazole; isohomohalicondrin B; itasetron; jasplakinolide; kahalalide F; larnellarin N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum complexes; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1 based therapy; mustard anti-cancer agent; mycaperoxide B; mycobacterial cell wall extract; myriaporone; N acetyldinaline; N substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06 benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum complexes; platinum triamine complex; porfimer sodium; porfiromycin; prednisone; acridones; prostaglandin J2; proteasome inhibitors; protein A based immune modulator; protein kinase C inhibitor; protein kinase C inhibitors, microalgal; protein tyrosine phosphatase inhibitors; purine nucleoside phosphorylase inhibitors; purpurins; pyrazoloaeridine; pyridoxylated hemoglobin polyoxyethylene conjugate; raf antagonists; raltitrexed; ramosetron; ras farnesyl protein transferase inhibitors; ras inhibitors; ras GAP inhibitor; retelliptine demethylated; rhenium Re 186 etidronate; rhizoxin; ribozymes; RH retinamide; rogletimide; rohitukine; romurtide; roquinimex; rubiginone BI; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

It is a further aspect of the invention that the present compounds can be administered in conjunction with chemical agents that are understood to mimic the effects of radiotherapy and/or that function by direct contact with DNA. Preferred agents for use in combination with the present compounds for treating cancer include, but are not limited to cis-diamminedichloro platinum (II) (cisplatin), doxorubicin, 5-fluorouracil, taxol, and topoisomerase inhibitors such as etoposide, teniposide, irinotecan and topotecan.

Additionally, the invention provides methods of treatment of cancer using the present compounds as an alternative to chemotherapy alone or radiotherapy alone where the chemotherapy or the radiotherapy has proven or can prove too toxic, e.g., results in unacceptable or unbearable side effects, for the subject being treated. The individual being treated can, optionally, be treated with another anticancer treatment modality such as chemotherapy, surgery, or immunotherapy, depending on which treatment is found to be acceptable or bearable.

The present compounds can also be used in an in vitro or ex vivo fashion, such as for the treatment of certain cancers, including, but not limited to leukemias and lymphomas, such treatment involving autologous stem cell transplants. This can involve a multi-step process in which the subject's autologous hematopoietic stem cells are harvested and purged of all cancer cells, the subject is then administered an amount of a present compound effective to eradicate the subject's remaining bone-marrow cell population, then the stem cell graft is infused back into the subject. Supportive care then is provided while bone marrow function is restored and the subject recovers.

The present methods for treating cancer can further comprise the administration of a present compound and an additional therapeutic agent or pharmaceutically acceptable salts or hydrates thereof. In one embodiment, a composition comprising a present compound is administered concurrently with the administration of one or more additional therapeutic agent(s), which may be part of the same composition or in a different composition from that comprising the present compound. In another embodiment, a present compound is administered prior to or subsequent to administration of another therapeutic agent(s).

In the present methods for treating cancer the other therapeutic agent may be an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, and tropisetron.

In a preferred embodiment, the antiemetic agent is granisetron or ondansetron. In another embodiment, the other therapeutic agent may be an hematopoietic colony stimulating factor. Suitable hematopoietic colony stimulating factors include, but are not limited to, filgrastim, sargrarnostim, molgramostim, and epoietin alfa.

In still another embodiment, the other therapeutic agent may be an opioid or non-opioid analgesic agent. Suitable opioid analgesic agents include, but are not limited to, morphine, heroin, hydromorphone, hydrocodone, oxymorphone, oxycodone, metopon, apomorphine, normorphine, etorphine, buprenorphine, meperidine, lopermide, anileridine, ethoheptazine, piminidine, betaprodine, diphenoxylate, fentanil, sufentanil, alfentanil, remifentanil, levorphanol, dextromethorphan, phenazocine, pentazocine, cyclazocine, methadone, isomethadone, and propoxyphene. Suitable non-opioid analgesic agents include, but are not limited to, aspirin, celecoxib, rofecoxib, diclofinac, diflusinal, etodolac, fenoprofen, flurbiprofen, ibuprofen, ketoprofen, indomethacin, ketorolac, meclofenamate, mefanamic acid, nabumetone, naproxen, piroxicam, and sulindac.

In still another embodiment, the other therapeutic agent may be an anxiolytic agent. Suitable anxiolytic agents include, but are not limited to, buspirene, and benzodiazepines such as diazepam, lorazepam, oxazapam, chlorazepate, clonazepam, chlordiazepoxide and alprazolam.

In addition to treating cancers and sensitizing a cancer cell to the cytotoxic effects of radiotherapy and chemotherapy, the present compounds are used in methods of treating diseases, conditions, and injuries to the central nervous system, such as neurological diseases, neurodegenerative disorders, and traumatic brain injuries (TBIs). In preferred embodiments, a present compound is capable of crossing the blood brain barrier to inhibit HDAC in the brain of the individual.

Alzheimer's Disease (AD) and Parkinson's Disease (PD) patient populations in the United States are estimated at over 5 million and 1 million, respectively. These numbers are expected to increase due to the aging United States population. Current treatments for these neurodegenerative diseases are inadequate because they fail to modify the diseases or to stop the progression of disease. The present compounds are specific HDAC6 inhibitors, and also are HIF1 and Nrf2 activators that penetrate the blood brain barrier. The present compounds are promising treatments for AD, PD, and CMT, which currently has no drug treatment. The present compounds are disease modifying and potentially disease progression arresting. The multiple mechanisms of action provide an ability for the present compounds to be excellent therapeutics for AD and PD.

It has been shown that HDAC6 inhibition protects against neuronal degeneration and stimulates neurite outgrowth in dorsal root ganglion neurons, therefore indicating methods of treating CNS diseases. Accordingly, present compounds were examined in a model of oxidative stress induced by homocysteic acid (HCA). This model leads to depletion of glutathione, the major intracellular antioxidant. HDAC6 inhibition rescues neuronal death in this model, possibly by causing hyperacetylation of peroxiredoxins. Previous work reported that nonselective, hydroxamic acid HDACIs displayed considerable toxicity to the primary cortical neurons. (A. P. Kozikowski et al., *J. Med. Chem.* 2007, 50, 3054-61.)

In HCA-induced neurodegeneration assays, TSA was found to be moderately neuroprotective at 0.5 µM, although protection declined at higher concentrations due to dose-dependant neurotoxicity. Compounds of the present invention displayed dose-dependent protection against HCA-induced neuronal cell death starting at 10 µM with near complete protection at 10 µM. This compares with published results showing that Tubacin induces α-tubulin acetylation at 5 µM and protects prostate cancer (LNCaP) cells from hydrogen peroxide-induced death at 8 µM via peroxiredoxin acetylation. (R. B. Parmigiani et al., *Proc. Natl. Acad. Sci. USA* 2008, 105, 9633-8.) Importantly, when tested at all of the concentrations shown, the present compounds exhibited no toxicity, indicating that neurotoxicity is likely a product of class I HDAC inhibition, and not a property inherent to hydroxamic acids. These results demonstrate that HDAC6 inhibition provides a method for treating neurodegenerative conditions.

The present compounds are HDAC inhibitors which also activate antioxidant mediators HIF1 and Nrf2. HDAC inhibition is selective for HDAC6, resulting in a reduced toxicity. HDAC inhibition has been shown to promote survival and regeneration of neurons, and to enhance learning and memory. HIF1 and Nrf2 activation stimulates the antioxidant gene pathway and is known to be beneficial in animal models of Parkinson's (PD) and Alzheimer's (AD) disease, as well as stroke and Charcot-Marie-Tooth (CMT). The present compounds enter the BBB resulting in the ability to affect neurological diseases. Because both epigenetic factors and oxidative stress are implicated in AD and PD, the present compounds are a triple acting medication.

The present compounds also provide a therapeutic benefit in models of peripheral neuropathies, such as CMT. HDAC6 inhibitors have been found to cross the blood nerve barrier and rescue the phenotype observed in transgenic mice exhibiting symptoms of distal hereditary motor neuropathy. Administration of HDAC6 inhibitors to symptomatic mice increased acetylated α-tubulin levels, restored proper mitochondrial motility and axonal transport, and increased muscle re-innervation. Other peripheral neuropathies include, but are not limited to, giant axonal neuropathy and various forms of mononeuropathies, polyneuropathies, autonomic neuropathies, and neuritis.

The present compounds therefore are useful for treating a neurological disease by administration of amounts of a present compound effective to treat the neurological disease or by administration of a pharmaceutical composition comprising amounts of a present compound effective to treat the neurological disease. The neurological diseases that can be treated include, but are not limited to, Huntington's disease, lupus, schizophrenia, multiple sclerosis, muscular dystrophy, dentatorubralpallidoluysian atrophy (DRRLA), spinal and bulbar muscular atrophy (SBMA), and fine spinocerebellar ataxias (SCA1, SCA2, SCA3/MJD (Machado-Joseph Disease), SCA6, and SCA7), drug-induced movement disorders, Creutzfeldt-Jakob disease, amyotrophic lateral sclerosis, Pick's disease, Alzheimer's disease, Lewy body dementia, cortico basal degeneration, dystonia, myoclonus, Tourette's syndrome, tremor, chorea, restless leg syndrome, Parkinson's disease, Parkinsonian syndromes, anxiety, depression, psychosis, manic depression, Friedreich's ataxia, Fragile X syndrome, spinal muscular dystrophy, Rett syndrome, Rubinstein-Taybi syndrome, Wilson's disease, multi-infarct state, CMT, GAN and other peripheral neuropathies.

In a preferred embodiment, the neurological disease treated is Huntington's disease, Parkinson's disease, Alzheimer's disease, spinal muscular atrophy, lupus, or schizophrenia.

A present compound also can be used with a second therapeutic agent in methods of treating conditions, diseases, and injuries to the CNS. Such second therapeutic agents are those drugs known in the art to treat a particular condition, diseases, or injury, for example, but not limited to, lithium in the treatment of mood disorders, estradiol benzoate, and nicotinamide in the treatment of Huntington's disease.

The present compounds also are useful in the treatment of TBIs. Traumatic brain injury (TBI) is a serious and complex injury that occurs in approximately 1.4 million people each year in the United States. TBI is associated with a broad spectrum of symptoms and disabilities, including a risk factor for developing neurodegenerative disorders, such as Alzheimer's disease.

TBI produces a number of pathologies including axonal injury, cell death, contusions, and inflammation. The inflammatory cascade is characterized by proinflammatory cytokines and activation of microglia which can exacerbate other pathologies. Although the role of inflammation in TBI is well established, no efficacious anti-inflammatory therapies are currently available for the treatment of TBI.

Several known HDAC inhibitors have been found to be protective in different cellular and animal models of acute and chronic neurodegenerative injury and disease, for example, Alzheimer's disease, ischemic stroke, multiple sclerosis, Huntington's disease (HD), amyotrophic lateral sclerosis (ALS), spinal muscular atrophy (SMA), and spinal and bulbar muscular atrophy (SBMA). A recent study in experimental pediatric TBI reported a decrease in hippocampal CA3 histone H3 acetylation lasting hours to days after injury. These changes were attributed to documented upstream excitotoxic and stress cascades associated with TBI. HDACIs also have been reported to have anti-inflammatory actions acting through acetylation of non-histone proteins. The HDAC6 selective inhibitor, 4-dimethylamino-N-[5-(2-mercaptoacetylamino)pentyl]benzamide (DMA-PB), was found to be able to increase histone H3 acetylation and reduce microglia inflammatory response following traumatic brain injury in rats, which demonstrates the utility of HDACIs as therapeutics for inhibiting neuroinflammation associated with TBI.

The present compounds therefore also are useful in the treatment of inflammation and strokes, and in the treatment of autism and autism spectrum disorders. The present compounds further can be used to treat parasitic infections, (e.g., malaria, toxoplasmosis, trypanosomiasis, helminthiasis, protozoal infections (see Andrews et al. *Int. J. Parasitol.* 2000, 30(6), 761-768).

In certain embodiments, the compound of the invention can be used to treat malaria. A present compound can be co-administered with an antimalarial compound selected from the group consisting of aryl amino alcohols, cinchona alkaloids, 4-aminoquinolines, type 1 or type 2 folate synthesis inhibitors, 8-aminoquinolines, antimicrobials, peroxides, naphthoquinones, and iron chelating agents. The antimalarial compound can be, but is not limited to, quinine, quinidine, mefloquine, halfantrine, chloroquine, amodiaquine, proguanil, chloroproquanil, pyrimethamine, primaquine, 8-[(4-amino-1-methylbutyl)amino]-2,6-dimethoxy-4-methyl-5-[(3-trifluoromethyl)phenoxy]quinoline succinate (WR238,605), tetracycline, doxycycline, clindamycin, azithromycin, fluoroquinolones, artemether, areether, artesunate, artelinic acid, atovaquone, and deferrioxamine. In a preferred embodiment, the antimalarial compound is chloroquine.

The present compounds also can be used as imaging agents. In particular, by providing a radiolabeled, isotopically labeled, or fluorescently-labeled HDACI, the labeled compound can image HDACs, tissues expressing HDACs, and tumors. Labeled compounds of the present invention also can image patients suffering from a cancer, or other HDAC-mediated diseases, e.g., stroke, by administration of an effective amount of the labeled compound or a composition containing the labeled compound. In preferred embodiments, the labeled compound is capable of emitting positron radiation and is suitable for use in positron emission tomography (PET). Typically, a labeled compound of the present invention is used to identify areas of tissues or targets that express high concentrations of HDACs. The extent of accumulation of labeled compound can be quantified using known methods for quantifying radioactive emissions. In addition, the labeled compound can contain a fluorophore or similar reporter capable of tracking the movement of particular HDAC isoforms or organelles in vitro.

The present compounds useful in the imaging methods contain one or more radioisotopes capable of emitting one or more forms of radiation suitable for detection by any standard radiology equipment, such as PET, SPECT, gamma cameras, MRI, and similar apparatus. Preferred isotopes including tritium ($^3$H) and carbon ($^{11}$C). Substituted compounds of the present invention also can contain isotopes of fluorine ($^{18}$F) and iodine ($^{123}$I) for imaging methods. Typically, a labeled compound of the present invention contains an alkyl group having a $^{11}$C label, i.e., a $^{11}$C-methyl group, or an alkyl group substituted with $^{18}$F, $^{123}$I, $^{125}$I, $^{131}$I, or a combination thereof.

Fluorescently-labeled compounds of the present invention also can be used in the imaging method of the present invention. Such compounds have an FITC, carbocyamine moiety or other fluorophore which will allow visualization of the HDAC proteins in vitro.

The labeled compounds and methods of use can be in vivo, and particularly on humans, and for in vitro applications, such as diagnostic and research applications, using body fluids and cell samples. Imaging methods using a labeled compound of the present invention are discussed in WO 03/060523, designating the U.S. and incorporated in its entirety herein. Typically, the method comprises contacting cells or tissues with a radiolabeled, isotopically labeled, fluorescently labeled, or tagged (such as biotin tagged) compound of the invention, and making a radiographic, fluorescent, or similar type of image depending on the visualization method employed, i.e., in regarded to radiographic images, a sufficient amount to provide about 1 to about 30 mCi of the radiolabeled compound.

Preferred imaging methods include the use of labeled compounds of the present invention which are capable of generating at least a 2:1 target to background ratio of radiation intensity, or more preferably about a 5:1, about 10:1, or about 15:1 ratio of radiation intensity between target and background.

In preferred methods, the labeled compounds of the present invention are excreted from tissues of the body quickly to prevent prolonged exposure to the radiation of the radiolabeled compound administered to the individual. Typically, labeled compounds of the present invention are eliminated from the body in less than about 24 hours. More preferably, labeled compounds are eliminated from the body in less than about 16 hours, 12 hours, 8 hours, 6 hours, 4 hours, 2 hours, 90 minutes, or 60 minutes. Typically, preferred labeled compounds are eliminated in about 60 to about 120 minutes.

In addition to isotopically labeled and fluorescently labeled derivatives, the present invention also embodies the use of derivatives containing tags (such as biotin) for the identification of biomolecules associated with the HDAC isoforms of interest for diagnostic, therapeutic or research purposes.

The present compounds also are useful in the treatment of autoimmune diseases and inflammations. Compounds of the present invention are particularly useful in overcoming graft and transplant rejections and in treating forms of arthritis.

Despite successes of modern transplant programs, the nephrotoxicity, cardiovascular disease, diabetes, and hyperlipidemia associated with current therapeutic regimens, plus the incidence of post-transplant malignancies and graft loss from chronic rejection, drive efforts to achieve long-term allograft function in association with minimal immunosuppression. Likewise, the incidence of inflammatory bowel disease (IBD), including Crohn's disease and ulcerative colitis, is increasing. Animal studies have shown that T regulatory cells (Tregs) expressing the forkhead transcription family member, Foxp3, are key to limiting autoreactive and alloreactive immunity. Moreover, after their induction by costimulation blockade, immunosuppression, or other strategies, Tregs may be adoptively transferred to naïve hosts to achieve beneficial therapeutic effects. However, attempts to develop sufficient Tregs that maintain their suppressive functions post-transfer in clinical trials have failed. Murine studies show that HDACIs limit immune responses, at least in significant part, by increasing Treg suppressive functions, (R. Tao et al., *Nat Med,* 13, 1299-1307, (2007)), and that selective targeting of HDAC6 is especially efficacious in this regard.

With organ transplantation, rejection begins to develop in the days immediately post-transplant, such that prevention rather than treatment of rejection is a paramount consideration. The reverse applies in autoimmunity, wherein a patient presents with the disease already causing problems. Accordingly, HDAC6−/− mice treated for 14 days with low-dose RPM (rapamycin) are assessed for displaying signs of tolerance induction and resistance to the development of chronic rejection, a continuing major loss of graft function long-term in the clinical transplant population. Tolerance is assessed by testing whether mice with long-surviving allografts reject a subsequent third-party cardiac graft and accept additional donor allografts without any immunosuppression, as can occur using a non-selective HDACI plus RPM. These in vivo sutides are accompanied by assessment of ELISPOT and MLR activities using recipient lymphocytes challenged with donor cells. Protection against chronic rejection is assessed by analysis of host anti-donor humoral responses and analysis of graft transplant arteriosclerosis and interstitial fibrosis in long-surviving allograft recipients.

The importance of HDAC6 targeting is assessed in additional transplant models seeking readouts of biochemical significance, as is monitored clinically. Thus, the effects of HDAC6 in targeting in renal transplant recipients (monitoring BUN, proteinuria) and islet allografts (monitoring blood glucose levels) are assessed. Renal transplants are the most common organ transplants performed, and the kidney performs multiple functions, e.g., regulating acid/base metabolism, blood pressure, red cell production, such that efficacy in this model indicates the utility of HDAC6 targeting. Likewise, islet transplantation is a major unmet need given that clinical islet allografts are typically lost after the first one or two years post-transplant. Having a safe and non-toxic means to extend islet survival without maintenance CNI therapy would be an important advance. Transplant studies also are strengthened by use of mice with floxed HDAC6. Using existing Foxp3-Cre mice, for example, the effects of deletion of HDAC6 just in Tregs is tested. This approach can be extended to targeting of HDAC6 in T cells (CD4-Cre) and dendritic cells (CD11c-Cre), for example. Using tamoxifen-regulated Cre, the importance of HDAC6 in induction vs. maintenance of transplants (with implications for short-term vs. maintenance HDAC6I therapy) is assessed by administering tamoxifen and inducing HDAC6 deletion at varying periods post-transplant.

Studies of autoimmunity also are undertaken. In this case, interruption of existing disease is especially important and HDAC6 targeting can be efficacious without any requirement for additional therapy (in contrast to a need for brief low-dose RPM in the very aggressive, fully MHC-mismatched transplant models). Studies in mice with colitis indicated that HDAC6−/− Tregs were more effective than WT Tregs in regulating disease, and tubacin was able to rescue mice if treatment was begun once colitis had developed. These studies are extended by assessing whether deletion of HDAC6 in Tregs (Foxp3/Cre) vs. T cells (CD4=Cre) vs. DC (CD11c-Cre) differentially affect the development and severity of colitis. Similarly, control of colitis is assessed by inducing HDAC6 deletion at varying intervals after the onset of colitis with tamoxifen-regulated Cre.

The present compounds are envisioned to demonstrate anti-arthritic efficacy in a collagen-induced arthritis model in DBA1/J mice. In this test, DBA1/J mice (male, 7-8 weeks) are used, with 8 animals per group. Systemic arthritis is induced with bovine collagen type II and CFA, plus an IFA booster injection on day 21. A present compound is dosed at 50 mg/kg and 100 mg/kg on day 28 for 2 consecutive weeks, and the effects determined from the Average Arthritic Score vs. Days of Treatment data.

Despite efforts to avoid graft rejection through host-donor tissue type matching, in the majority of transplantation procedures, immunosuppressive therapy is critical to the viability of the donor organ in the host. A variety of immunosuppressive agents have been employed in transplantation procedures, including azathioprine, methotrexate, cyclophosphamide, FK-506, rapamycin, and corticosteroids.

The present compounds are potent immunosuppressive agents that suppress humoral immunity and cell-mediated immune reactions, such as allograft rejection, delayed hypersensitivity, experimental allergic encephalomyelitis, Freund's adjuvant arthritis and graft versus host disease. Compounds of the present invention are useful for the prophylaxis of organ rejection subsequent to organ transplantation, for treatment of rheumatoid arthritis, for the treatment of psoriasis, and for the treatment of other autoimmune diseases, such as type I diabetes, Crohn's disease, and lupus.

A therapeutically effective amount of a present compound can be used for immunosuppression including, for example, to prevent organ rejection or graft vs. host disease, and to treat diseases and conditions, in particular, autoimmune and inflammatory diseases and conditions. Examples of autoimmune and inflammatory diseases include, but are not limited to, Hashimoto's thyroiditis, pernicious anemia, Addison's disease, psoriasis, diabetes, rheumatoid arthritis, systemic lupus erythematosus, dermatomyositis, Sjogren's syndrome, dermatomyositis, lupus erythematosus, multiple sclerosis, myasthenia gravis, Reiter's syndrome, arthritis (rheumatoid arthritis, arthritis chronic progrediente, and arthritis deformans) and rheumatic diseases, autoimmune hematological disorder (hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, psoriasis, Steven-Johnson syndrome, idiopathic sprue, autoimmune inflammatory bowel disease (ulcerative colitis and Crohn's disease) endocrine opthalmopathy, Graves disease, sarcoidosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis, and glomerulonephritis.

A present compound can be used alone, or in conjunction with a second therapeutic agent known to be useful in the treatment of autoimmune diseases, inflammations, transplants, and grafts, such as cyclosporin, rapamycin, methotrexate, cyclophosphamide, azathioprine, corticosteroids, and similar agents known to persons skilled in the art.

Additional diseases and conditions mediated by HDACs, and particularly HDAC6, include, but are not limited to asthma, cardiac hypertrophy, giant axonal neuropathy, mononeuropathy, mononeuritis, polyneuropathy, autonomic neuropathy, neuritis in general, and neuropathy in general. These disease and conditions also can be treated by a method of the present invention.

In the present method, a therapeutically effective amount of one or more compound of the present invention, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A present compound can be administered by any suitable route, for example by oral, buccal, inhalation, topical, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a present compound is present in a sufficient amount to be administered in an effective amount to achieve its intended purpose. The exact formulation, route of administration, and dosage is determined by an individual physician in view of the diagnosed condition or disease. Dosage amount and interval can be adjusted individually to provide levels of a present compound that is sufficient to maintain therapeutic effects.

Toxicity and therapeutic efficacy of the present compound compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds that exhibit high therapeutic indices are preferred. The data obtained from such procedures can be used in formulating a dosage range for use in humans. The dosage preferably lies within a range of circulating compound concentrations that include the $ED_{50}$ with little or no toxicity. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a present compound required for use in therapy varies with the nature of the condition being treated, the length of time that activity is desired, and the age and the condition of the patient, and ultimately is determined by the attendant physician. Dosage amounts and intervals can be adjusted individually to provide plasma levels of the HDACI that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present compound can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

The dosage of a composition containing a present compound, or a composition containing the same, can be from about 1 ng/kg to about 200 mg/kg, about 1 µg/kg to about 100 mg/kg, or about 1 mg/kg to about 50 mg/kg of body weight. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

A present compound used in a method of the present invention typically is administered in an amount of about 0.005 to about 500 milligrams per dose, about 0.05 to about 250 milligrams per dose, or about 0.5 to about 100 milligrams per dose. For example, a present compound can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of the present compounds.

The term "carrier" refers to a diluent, adjuvant, or excipient, with which a present compound is administered. Such pharmaceutical carriers can be liquids, such as water and oils, including those of petroleum, animal, vegetable or synthetic origin, such as peanut oil, soybean oil, mineral oil, sesame oil, and the like. The carriers can be saline, gum acacia, gelatin, starch paste, talc, keratin, colloidal silica, urea, and the like. In addition, auxiliary, stabilizing, thickening, lubricating and coloring agents can be used. The pharmaceutically acceptable carriers are sterile. Water is a preferred carrier when a present HDACI is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The present compositions, if desired, can also contain minor amounts of wetting or emulsifying agents, or pH buffering agents.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of a present compound is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a present compound. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a present compound.

When a therapeutically effective amount of a present compound is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains an isotonic vehicle. A present compound can be infused with other fluids over a 10-30 minute span or over several hours.

The present compounds can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding a present HDACI to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A present compound can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a present compound can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A present compound also can be formulated in rectal compositions, such as suppositories or retention enemas, e.g., containing conventional suppository bases. In addition to the formulations described previously, a present compound also can be formulated as a depot preparation. Such long-acting formulations can be administered by implantation (for example, subcutaneously or intramuscularly) or by intramuscular injection. Thus, for example, a present compound can be formulated with suitable polymeric or hydrophobic materials (for example, as an emulsion in an acceptable oil) or ion exchange resins.

In particular, a present compound can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The present compounds also can be injected parenterally, for example, intravenously, intramuscularly, subcutaneously, or intracoronarily. For parenteral administration, the present compounds are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a present compound and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration, for example, a syringe, drip bag, or patch. In another embodiment, the present compounds is a lyophilate. In this instance, the kit can further comprise an additional container which contains a solution useful for the reconstruction of the lyophilate.

Prior HDACIs possessed properties that hindered their development as therapeutic agents. In accordance with an important feature of the present invention, the present HDACIs were synthesized and evaluated as inhibitors for HDAC. The present compounds demonstrate an increased HDAC6 potency and selectivity against HDAC1 and HDAC8 with improvements in BEI relative to prior compounds. The improved properties of the present compounds, particularly the increase in BEI and reduced potency at HDAC8, indicate that the present compounds are useful for applications such as, but not limited to, immunosuppresssive and neuroprotective agents. For example, compounds of the present invention typically have a bonding affinity ($IC_{50}$) to HDAC6 of less than 100 nM, less than 50 nm, less than 25 nM, less than 20 nM, and less than 15 nM.

What is claimed is:

1. A compound having a structural formula

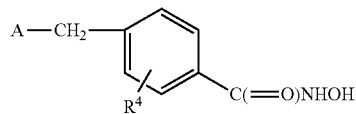

wherein A is

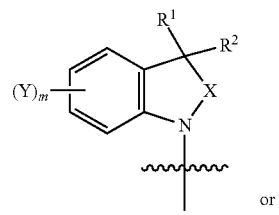

or

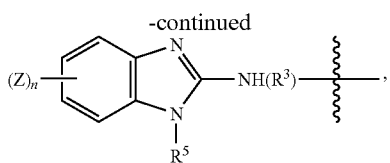

wherein X is —CH$_2$— or

Y, independently, is selected from the group consisting of halo, —OH, —CN, —NO$_2$, C$_{1-6}$alkyl, aryl, heteroaryl, —OR$^a$, —N(R$^a$)$_2$, —NHR$^a$, —CO—N(R$^a$)$_2$, —NHCO—R$^a$, —CO$_2$R$^a$, —SR$^a$, —OCOR$^a$, —NHSO$_2$R$^a$, —SO$_2$N(R$^a$)$_2$, and —SO$_2$R$^a$; or two Y groups, positioned ortho to one another, are taken together with the carbon atoms to which they are attached to form a five or six-membered carbocyclic ring or a five or six-membered heterocyclic ring containing one or two heteroatoms selected from O, S, and NR$^a$;

m is an integer 0, 1, 2, 3, or 4;

Z, independently, is selected from the group consisting of halo, —OH, —CN, —NO$_2$, C$_{1-6}$alkyl, aryl, heteroaryl, —OR$^a$, —N(R$^a$)$_2$, —NHR$^a$, —CO—N(R$^a$)$_2$, —NHCO—R$^a$, —CO$_2$R$^a$, —SR$^a$, —OCOR$^a$, —NHSO$_2$R$^a$, —SO$_2$N(R$^a$)$_2$, and —SO$_2$R$^a$; or two Z groups, positioned ortho to one another, are taken together with the carbon atoms to which they are attached to form a five or six-membered carbocyclic ring or a five or six-membered heterocyclic ring containing one or two heteroatoms selected from O, S, and NR$^a$;

n is an integer 0, 1, 2, 3, or 4;

R$^1$ and R$^2$, independently, are hydrogen, halo, or C$_{1-6}$alkyl, or R$^1$ is a five- or six-membered nitrogen-containing ring and R$^2$ is hydrogen, halo, or C$_{1-6}$alkyl, or R$^1$ and R$^2$ are taken together with the carbon atoms to which they are attached to form a three to six-membered carbocyclic or heterocyclic ring;

R$^a$ is hydrogen, C$_{1-6}$alkyl, aryl, or heteroaryl;

R$^3$ is hydrogen, C$_{1-6}$alkyl, —CH$_2$aryl, aryl, or heteroaryl;

R$^4$ is hydrogen or halo; and

R$^5$ is C$_{1-3}$alkyl or aryl;

or a pharmaceutically acceptable salt thereof.

2. The compound of claim 1 wherein Y is null, Cl, F, —OCH$_3$, —OBn, —NO$_2$, —N(CH$_3$)$_2$, —NHSO$_2$CH$_3$, —SCH$_3$, —C$_6$H$_5$,

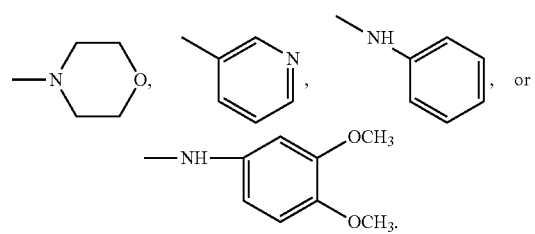

or wherein two Y groups ortho to one another are taken together to form

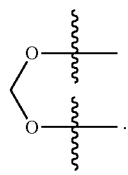 [SMILES: *OCO*]

3. The compound of claim 1 wherein m is 2 and each Y is halo.

4. The compound of claim 3 wherein a first Y is F and a second Y is Cl.

5. The compound of claim 1 wherein m is 0, 1, or 2.

6. The compound of claim 1 wherein R$^1$ and R$^2$ each are hydrogen, each are methyl, each are fluoro, or are taken together with the carbon to which they are attached to form a cyclopropyl group.

7. The compound of claim 1 wherein R$^3$ is H, —CH$_3$, or —CH$_2$C$_6$H$_5$.

8. The compound of claim 1 wherein R$^4$ is H or F.

9. The compound of claim 1 wherein R$^5$ is —CH$_3$ or —C$_6$H$_5$.

10. The compound of claim 1 wherein Z is null, Cl, or —OCH$_3$.

11. A compound selected from the group consisting of

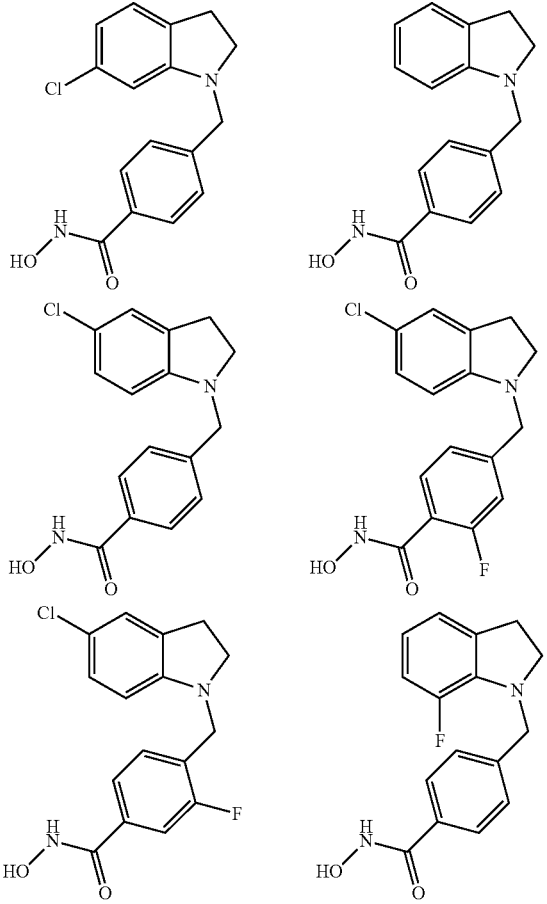

-continued
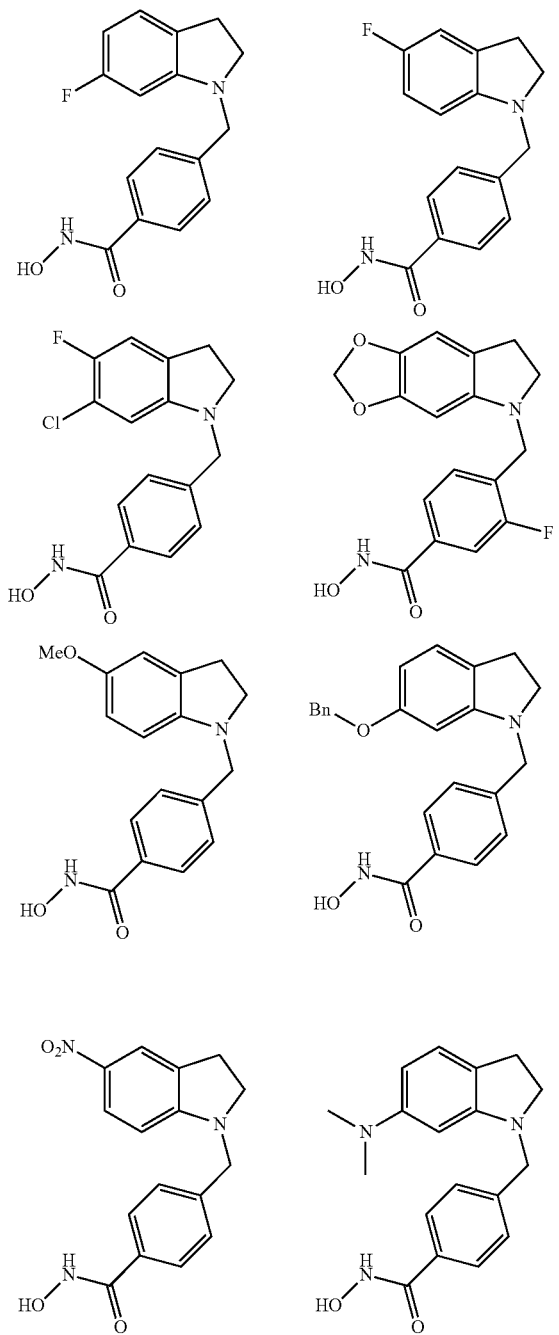
-continued
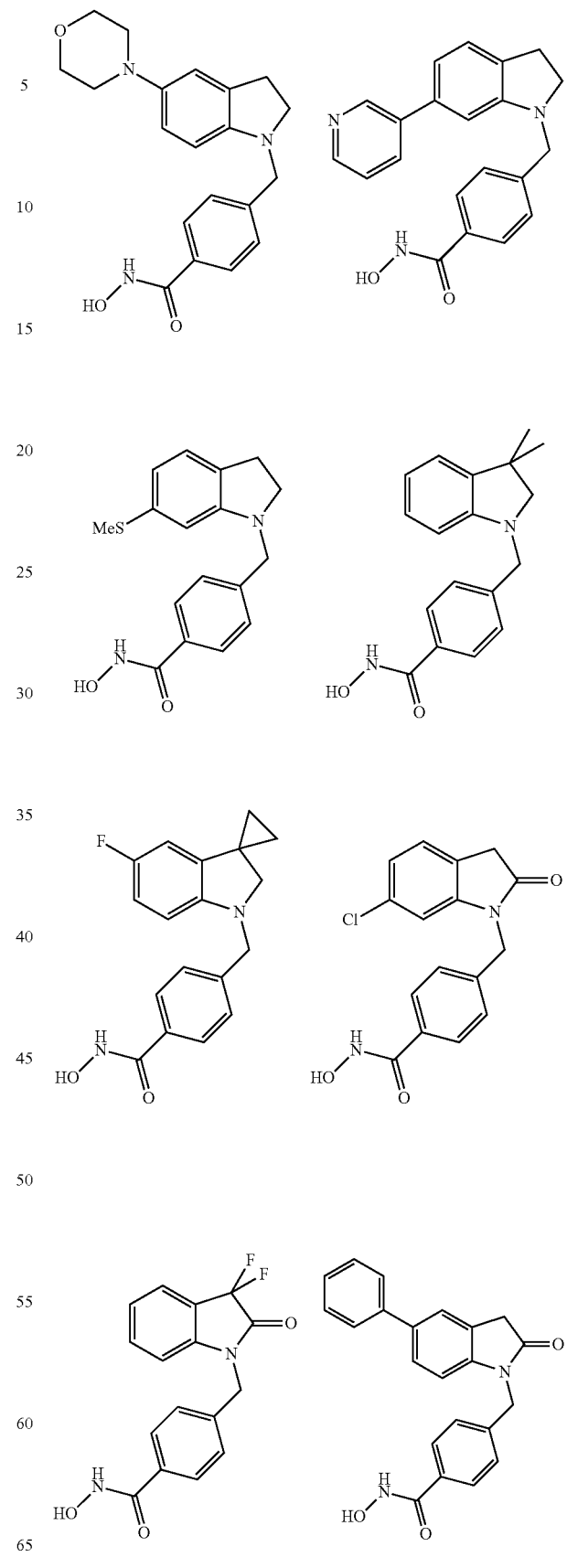

-continued
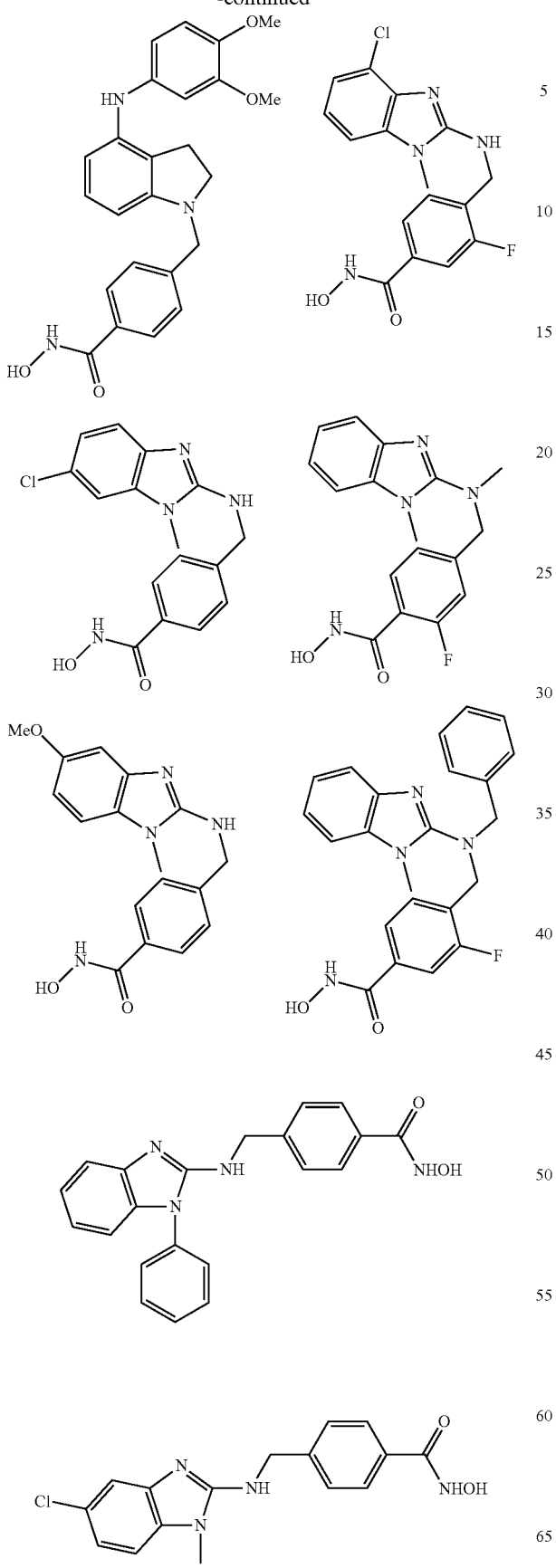
-continued
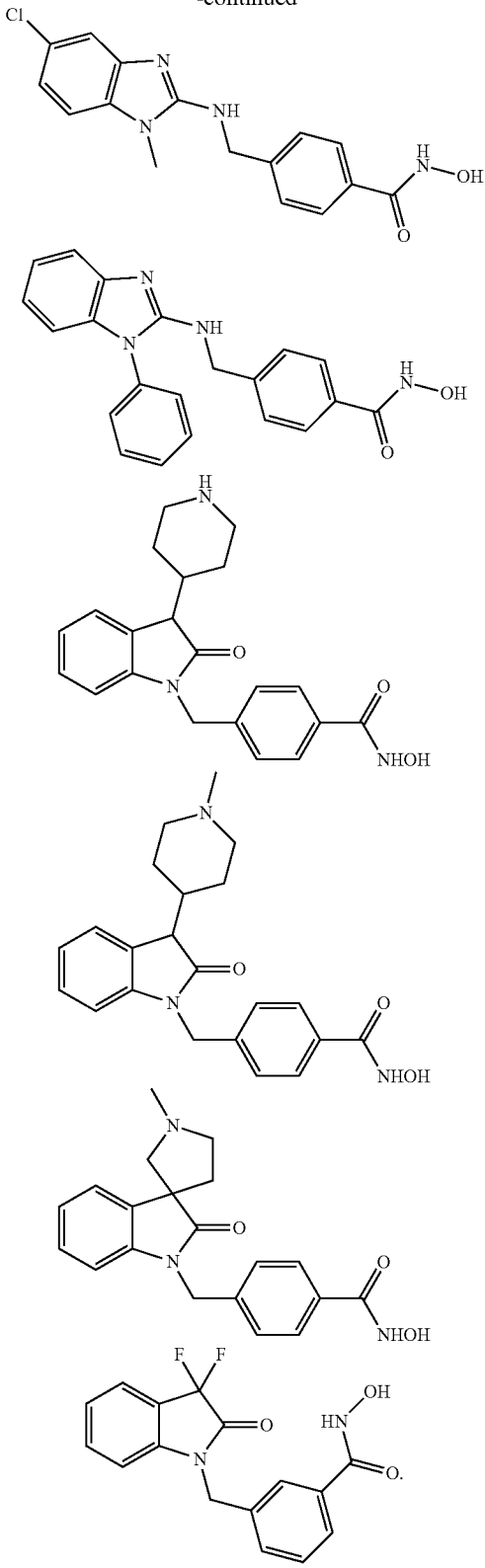
12. A pharmaceutical composition comprising a compound of claim 1 and a pharmaceutically acceptable carrier or vehicle.
13. A method of treating a disease or condition wherein inhibition of HDAC and/or activation of Nrf2 and HIF provides a benefit comprising administering a therapeutically effective amount of a compound of claim 1 to an individual in need thereof.

14. The method of claim 13 wherein the HDAC is HDAC6.

15. The method of claim 13 wherein the disease or condition is a cancer.

16. The method of claim 13 wherein the disease or condition is a neurological disease, a neurodegenerative disorder, peripheral neuropathy, a traumatic brain injury, stroke, an inflammation, or an autoimmune disease.

17. The compound of claim 1 wherein m is 1 and Y is Cl or F.

18. The compound of claim 11 selected from the group consisting of

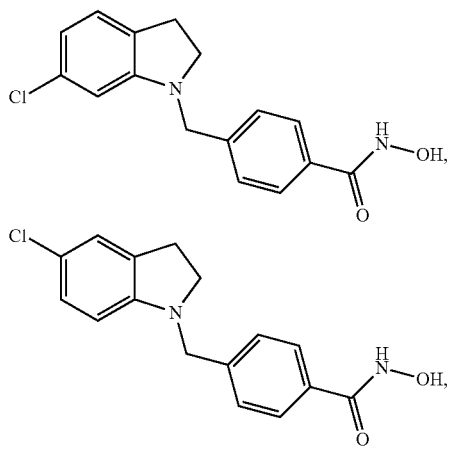

-continued

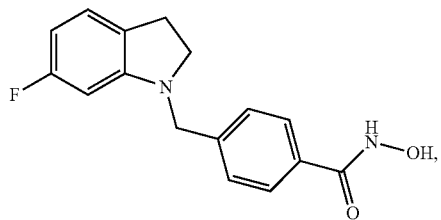

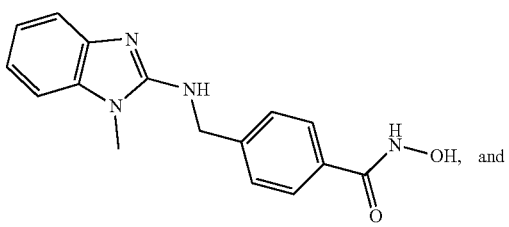

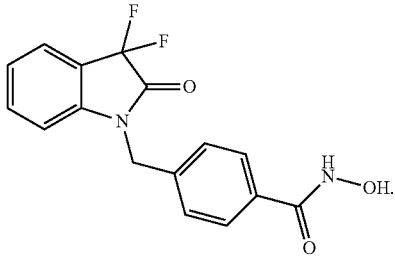

* * * * *